United States Patent
Frysz et al.

(10) Patent No.: US 9,931,514 B2
(45) Date of Patent: *Apr. 3, 2018

(54) LOW IMPEDANCE OXIDE RESISTANT GROUNDED CAPACITOR FOR AN AIMD

(71) Applicant: Greatbatch Ltd., Clarence, NY (US)

(72) Inventors: Christine A. Frysz, Orchard Park, NY (US); Robert A. Stevenson, Canyon Country, CA (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/250,210

(22) Filed: Aug. 29, 2016

(65) Prior Publication Data

US 2016/0367821 A1   Dec. 22, 2016

Related U.S. Application Data

(63) Continuation-in-part of application No. 14/826,229, filed on Aug. 14, 2015, now Pat. No. 9,427,596, (Continued)

(51) Int. Cl.
| | |
|---|---|
| *A61N 1/00* | (2006.01) |
| *A61N 1/375* | (2006.01) |
| *H02G 15/013* | (2006.01) |
| *H01G 4/40* | (2006.01) |
| *H01G 2/02* | (2006.01) |
| *H01G 4/35* | (2006.01) |
| *H01G 4/228* | (2006.01) |

(Continued)

(52) U.S. Cl.
CPC .......... *A61N 1/3754* (2013.01); *H01G 2/02* (2013.01); *H01G 4/228* (2013.01); *H01G 4/35* (2013.01);
(Continued)

(58) Field of Classification Search
CPC ........................................ A61N 1/375–1/3754
See application file for complete search history.

(56) References Cited

U.S. PATENT DOCUMENTS

| | | |
|---|---|---|
| 3,681,612 A | 8/1972 | Kinzler et al. |
| 3,745,430 A | 7/1973 | Kerr et al. |

(Continued)

FOREIGN PATENT DOCUMENTS

| | | |
|---|---|---|
| EP | 0243573 | 11/1987 |
| EP | 0145430 | 5/1991 |

(Continued)

OTHER PUBLICATIONS

Konings, et al., "Heating Around Intravascular Guidewires by Resonating RF Waves", Journal of Magnetic Resonance Imaging, 2000, 79-85.

(Continued)

*Primary Examiner* — Scott Getzow
(74) *Attorney, Agent, or Firm* — Marc G. Martino; Michael F. Scalise

(57) ABSTRACT

A hermetically sealed filtered feedthrough assembly for an active implantable medical device includes an electrically conductive ferrule hermetically sealed by a first braze to an insulator. A conductor is hermetically sealed to and disposed through the insulator. A filter capacitor has an active electrode plate and a ground electrode plate which are disposed within and supported by a capacitor dielectric in an interleaved, partially overlapping relationship. A first passageway is disposed through the capacitor dielectric having a capacitor internal metallization which is connected to the active electrode plate. A capacitor external metallization electrically connects to the ground electrode plate. An oxide-resistant metal addition includes a conductive core with a conductive cladding of a different material. A first electrical connection is between the oxide-resistant metal addition and the capacitor external metallization. A second electrical connection is between the oxide-resistant metal addition and the ferrule.

24 Claims, 47 Drawing Sheets

BODY FLUID SIDE

Related U.S. Application Data which is a continuation-in-part of application No. 14/202,653, filed on Mar. 10, 2014, now Pat. No. 9,108,066.

(60) Provisional application No. 61/841,419, filed on Jun. 30, 2013.

(51) Int. Cl.
*H03H 1/00* (2006.01)
*H01R 13/7197* (2011.01)
*H01R 13/52* (2006.01)

(52) U.S. Cl.
CPC ........... *H01G 4/40* (2013.01); *H01R 13/7197* (2013.01); *H02G 15/013* (2013.01); *H03H 1/00* (2013.01); *H01R 13/5224* (2013.01); *H03H 2001/0042* (2013.01); *H03H 2001/0085* (2013.01)

(56) References Cited

U.S. PATENT DOCUMENTS

| | | |
|---|---|---|
| 3,871,382 A | 3/1975 | Mann |
| 3,961,294 A | 6/1976 | Hollyday |
| 3,968,802 A | 7/1976 | Ballis |
| 3,980,975 A | 9/1976 | Maxon et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton et al. |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh et al. |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Segawa et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,944,298 A | 7/1990 | Sholder |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,039,965 A | 8/1991 | Higgins |
| 5,044,375 A | 9/1991 | Bach et al. |
| 5,052,404 A | 10/1991 | Hodgson et al. |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,268,810 A | 12/1993 | Dimarco et al. |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinclarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rhinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |
| 5,700,548 A | 12/1997 | Warnier et al. |
| 5,706,810 A | 1/1998 | Rubinskr et al. |
| 5,715,825 A | 2/1998 | Crowley |
| 5,716,390 A | 2/1998 | Li |
| 5,722,998 A | 3/1998 | Prutchi et al. |
| 5,735,884 A | 4/1998 | Thompson et al. |
| 5,735,887 A | 4/1998 | Barreras et al. |
| 5,741,321 A | 4/1998 | Brennen |
| 5,751,539 A | 5/1998 | Stevenson et al. |
| 5,757,252 A | 5/1998 | Cho |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |

(56) References Cited

U.S. PATENT DOCUMENTS

| | | |
|---|---|---|
| 5,782,891 A | 7/1998 | Hassler et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A | 1/1999 | Haq et al. |
| 5,864,234 A | 1/1999 | Luedeke |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A | 11/2000 | Haq et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |
| 6,949,929 B2 | 9/2005 | Gray et al. |
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,999,818 B2 | 2/2006 | Stevenson et al. |
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |

(56) References Cited

U.S. PATENT DOCUMENTS

| | | |
|---|---|---|
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,199,995 B2 | 4/2007 | Stevenson |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,561,906 B2 | 7/2009 | Atalar et al. |
| 7,586,728 B2 | 9/2009 | Anthony |
| 7,593,208 B2 | 9/2009 | Anthony et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,163,397 B2 | 4/2012 | Ok et al. |
| 8,219,208 B2 | 7/2012 | Stevenson et al. |
| 8,301,249 B2 | 10/2012 | Min |
| 8,659,870 B2 | 2/2014 | Brendel et al. |
| 8,763,245 B1 | 7/2014 | Lucisano et al. |
| 8,874,206 B2 | 10/2014 | Malinowski et al. |
| 9,108,066 B2 | 8/2015 | Woods et al. |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Lyer et al. |
| 2007/0179577 A1 | 8/2007 | Marshall et al. |

(56) References Cited

U.S. PATENT DOCUMENTS

| | | |
|---|---|---|
| 2007/0203529 A1 | 8/2007 | Iyer et al. |
| 2007/0208383 A1 | 9/2007 | Williams |
| 2007/0250143 A1 | 10/2007 | Sommer et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163974 A1* | 6/2009 | Taylor .............. A61N 1/3754 607/36 |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0149042 A1 | 6/2010 | Utsi et al. |
| 2010/0151113 A1 | 6/2010 | Shelton |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2011/0043297 A1 | 2/2011 | Stevenson et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0498996 | 3/1997 |
| EP | 1021730 | 4/2003 |
| EP | 0930509 | 3/2004 |
| EP | 1469910 | 12/2006 |
| EP | 1883449 | 1/2009 |
| EP | 2025361 | 2/2009 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 7272975 JP | 10/1995 |
| JP | 9094238 | 4/1997 |
| JP | 11239572 | 9/1999 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |
| WO | 2013/158552 | 10/2013 |

OTHER PUBLICATIONS

Luchinger, "Safety Aspects of Cardiac Pacemakers in Magnetic Resonance Imaging", A dissertation submitted to the Swiss Federal Institute of Technology Zurich, Switzerland, 2002.

Roguin, et al., "Modern Pacemaker and Implantable Cardioverter/Defibrillator systems Can Be Magnetic Resonance Imaging Safe", Journal of the American Heart Association, Aug. 4, 2004, 475-482.

Search, European Search Report, Application No. 12157697.9, dated Jul. 5, 2012.

Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.

Shellock, "MRI Issues for Neuromodulation Devices", Institute for Magnetic Resonance Safety Education, and Research (IMRSER).

Susil, et al., "Multifunctional Interventional Devices for MRI: A Combined Electrophysiology/MRI Catheter", 2002, 594-600.

(56) References Cited

OTHER PUBLICATIONS

Susil, et al., U.S. Appl. No. 60/283,725, Multifunctional Interventional Devices for Use in MRI, filed Apr. 13, 2001.
Weiner, et al., U.S. Appl. No. 60/269,817, Electromagnetic Interference immune Cardiac Assist System, filed Feb. 20, 2001.
Wilk, et al., "High-K Gate Dielectrics: Current Status and Materials Properties Considerations", Journal of Applied Physics, vol. 89, No. 10, May 15, 2001, 5243-5275.
Balanis, "Advanced Engineering Electromagnetics", 1989.
Clement et al., "Estimation of Effective Lead Loop Area for Implantable Pulse Generators and Cardioverter/Defibrillators for Determination of Susceptibility to Radiated Electromagnetic Interference", AAMI EMC Task Force, Apr. 12, 2004, 10 pages.
Ennis et al., "Cautions About the Use of Equivalent Series Resistance (ESR) in Specifying Capacitors", Mar. 8, 1993, 58-64.
EPsearch, Application 10167031.3, Sep. 19, 2012.
EPsearch, Application 10167045.3, Oct. 10, 2012.
Gabriel et al., "The Dielectric Properties of Biological Tissues: Parametric Models for the Dielectric Spectrum of Tissues", Parametric Models for the Dielectric Spectrum of Tissues, Phys. Med. Bio. 41, 1996, 2271-2293.
Johnson et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.

\* cited by examiner

BODY FLUID SIDE

BODY FLUID SIDE
PRIOR ART

BODY FLUID SIDE
PRIOR ART

BODY FLUID SIDE

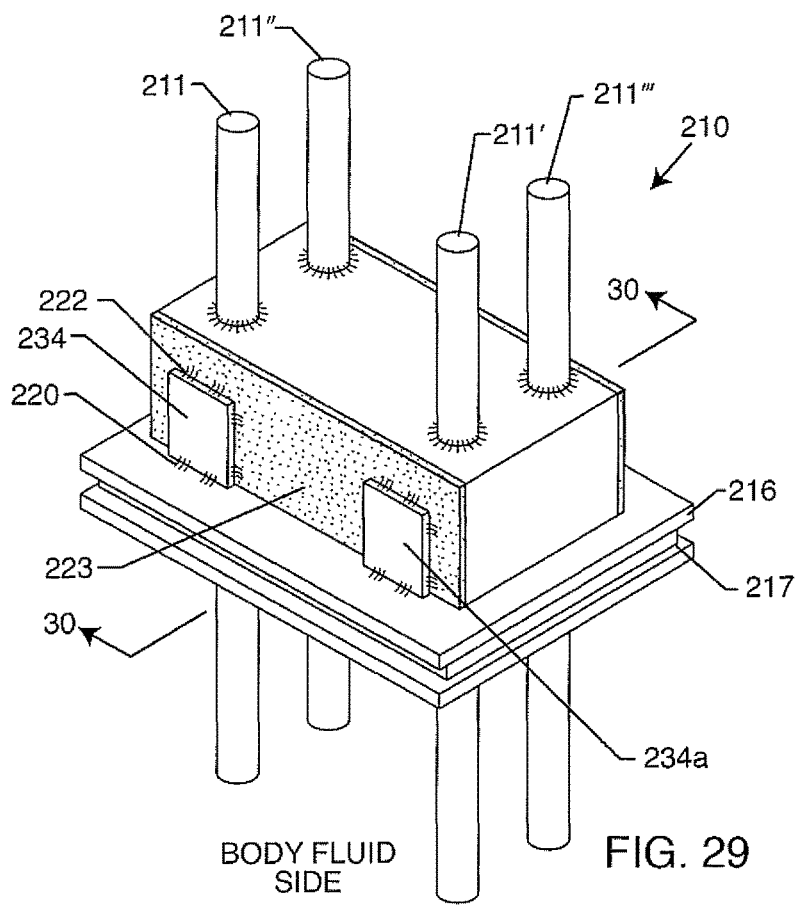
BODY FLUID SIDE    FIG. 29
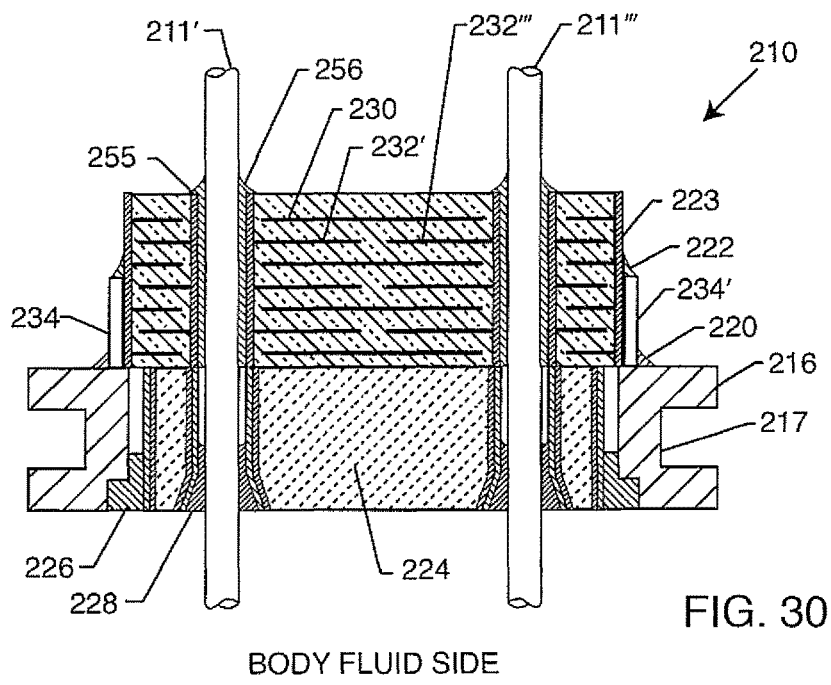
BODY FLUID SIDE    FIG. 30

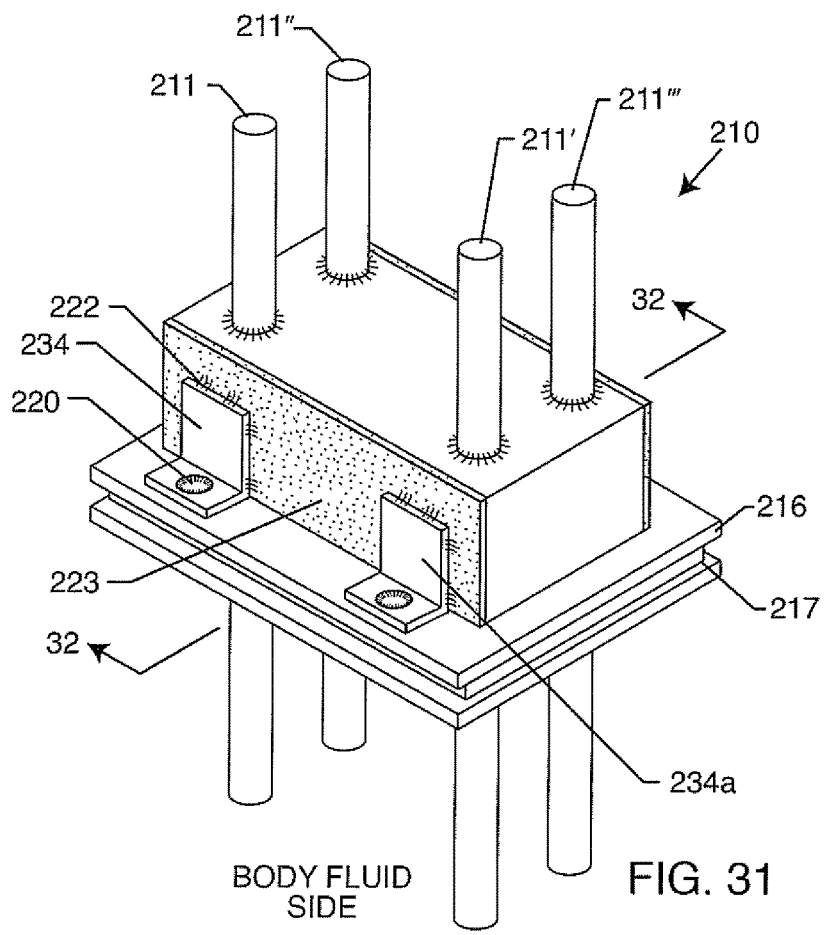
BODY FLUID SIDE    FIG. 31
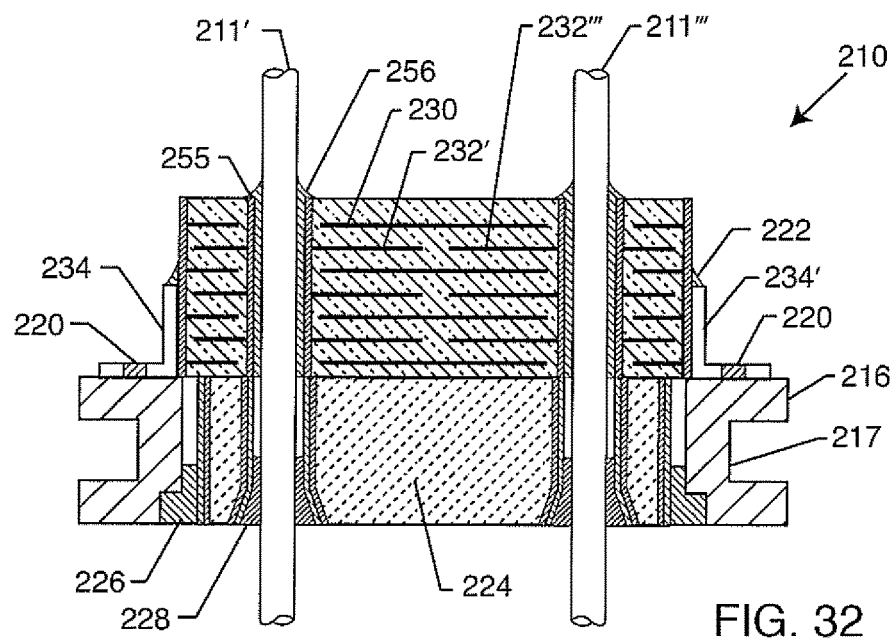
BODY FLUID SIDE    FIG. 32

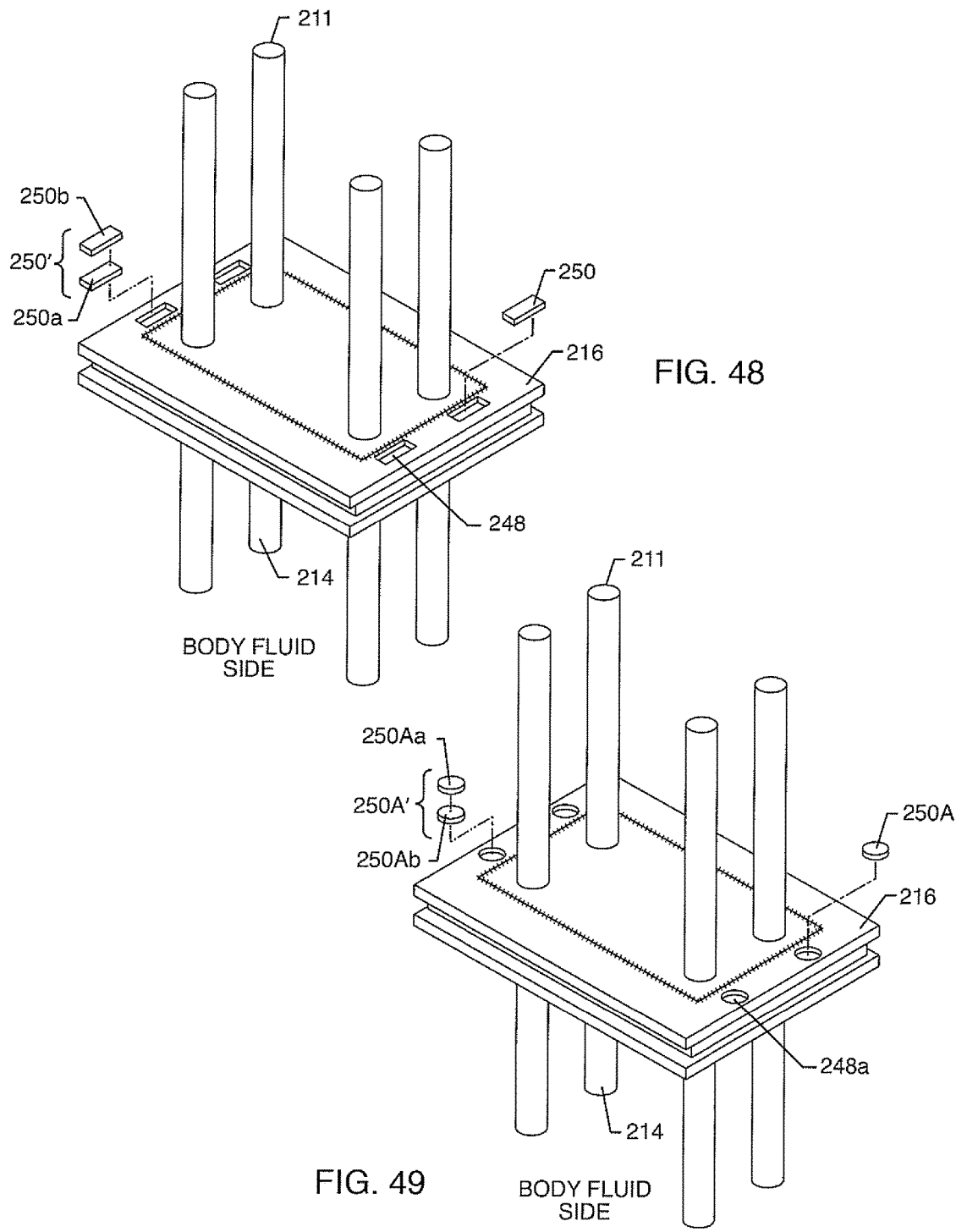

BODY FLUID SIDE

BODY FLUID SIDE

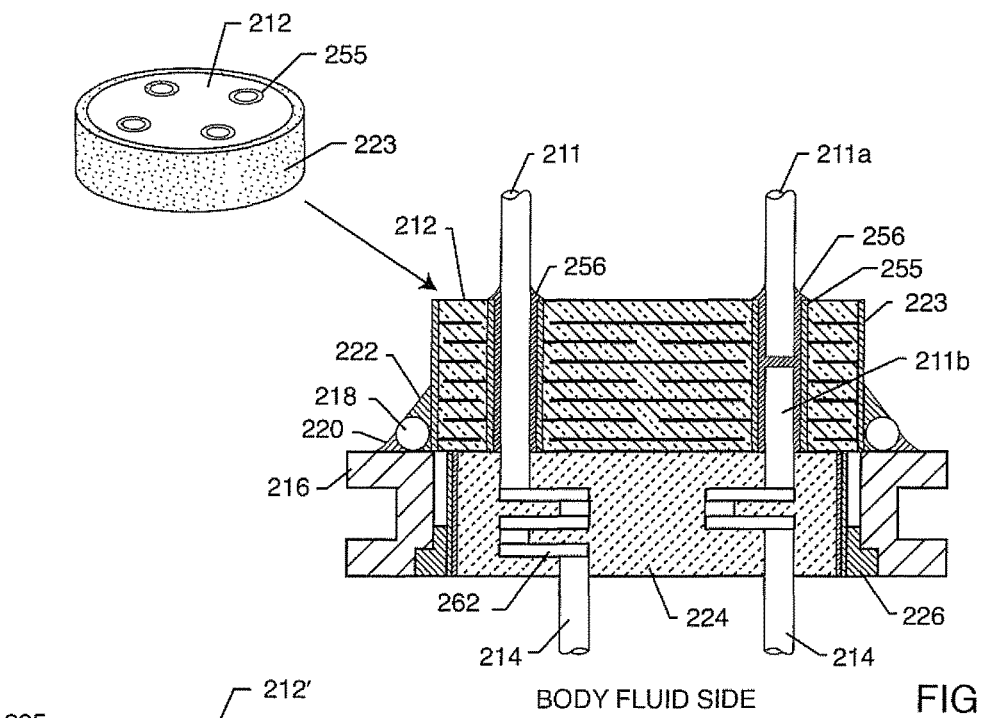
BODY FLUID SIDE  FIG. 60
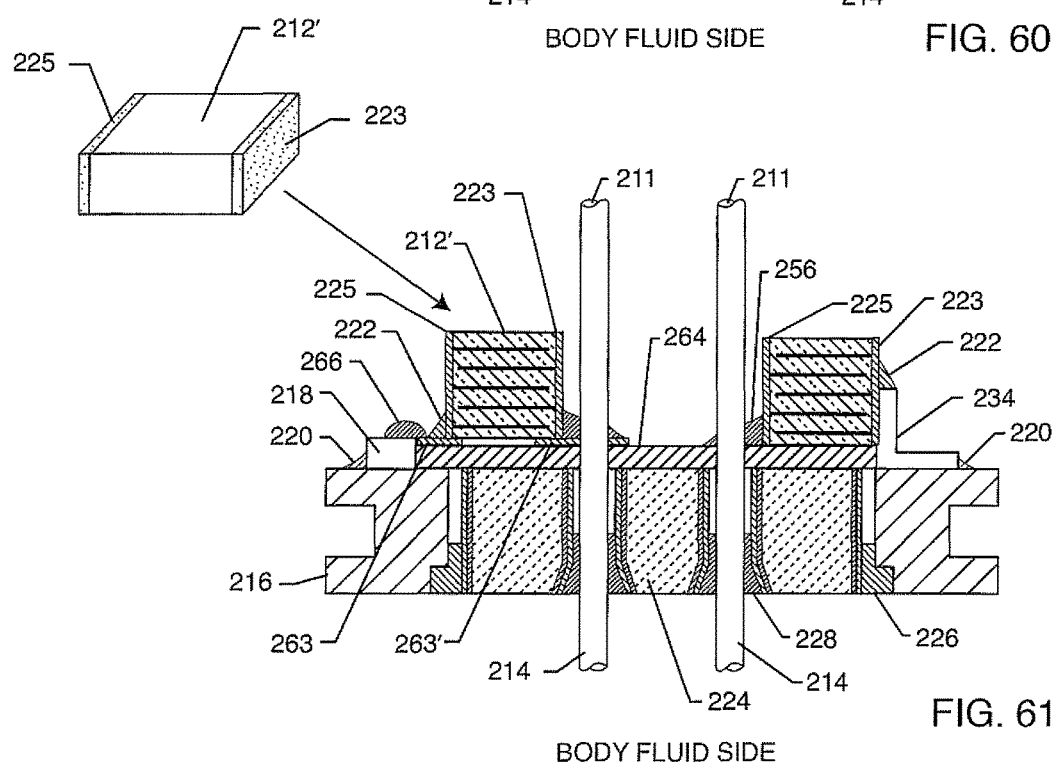
BODY FLUID SIDE  FIG. 61

BODY FLUID SIDE

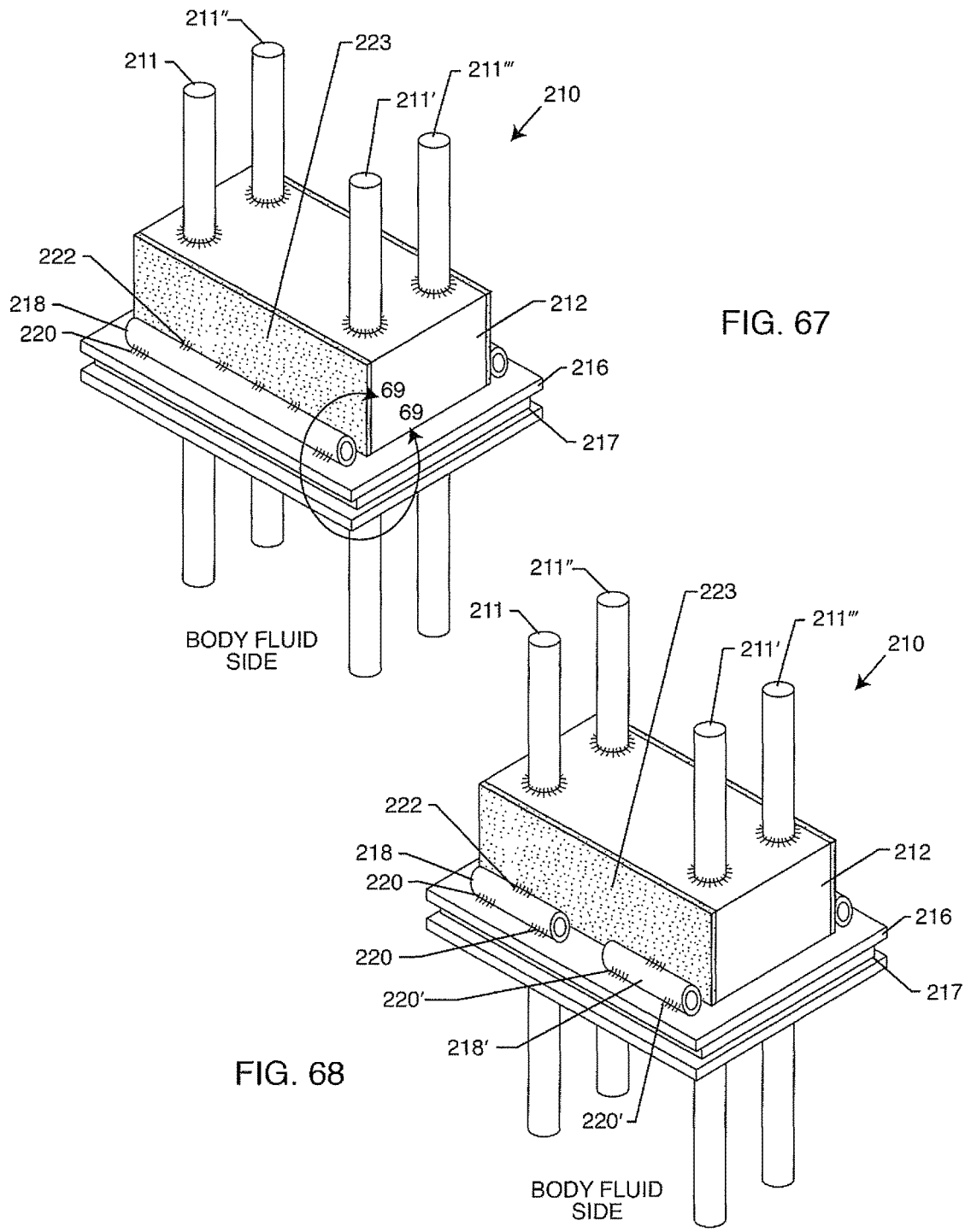

LOW IMPEDANCE OXIDE RESISTANT GROUNDED CAPACITOR FOR AN AIMD

CROSS-REFERENCE TO RELATED APPLICATIONS

This continuation-in-part application claims priority to U.S. patent application Ser. No. 14/826,229, filed on Aug. 14, 2015; now U.S. Pat. No. 9,427,596, which is a continuation-in-part application to U.S. patent application Ser. No. 14/202,653, filed on Mar. 10, 2014, now U.S. Pat. No. 9,108,066, which claims the benefit of U.S. provisional application Ser. No. 61/841,419, filed on Jun. 30, 2013; the contents of which all of these applications are fully incorporated herein with these references.

FIELD OF THE INVENTION

The present invention generally relates to feedthrough capacitors. More particularly, the present invention relates to a feedthrough capacitor located on the device side of a medical device with a low impedance and oxide-resistant electrical connection to the device housing.

BACKGROUND OF THE INVENTION

Feedthrough capacitors and MLCC chip capacitors are well known in the prior art for active implantable medical devices (AIMDs). One is directed to U.S. Pat. Nos. 5,333,095; 5,905,627; 6,275,369; 6,529,103; and 6,765,780 all of which are incorporated herein by reference. The hermetic seal feedthrough terminal assemblies generally consist of a titanium ferrule into which an alumina hermetic seal is gold brazed. One or more leadwires penetrate through the alumina in non-conductive relationship with the ferrule. Gold brazes are also used to form a hermetic terminal between the one or more leadwires and the alumina ceramic.

First, some general information concerning good engineering design practice for electromagnetic interference (EMI) filters is described. It is very important to intercept the EMI at the point of lead conductor ingress and egress to the AIMD. It would be an inferior practice to put filtering elements down in the circuit board as this would draw EMI energy inside of the AIMD housing where it could re-radiate or cross-couple to sensitive AIMD circuits. A superior approach is to mount one or more feedthrough or MLCC-type capacitors right at the point of leadwire entrance so that the capacitor can be coupled to high frequency EMI signals from the lead conductors directly to the AIMD housing, which acts as an energy dissipating surface.

There are some interesting design challenges however. The titanium ferrule, which is laser welded into the overall AIMD housing, is at ground potential. Titanium tends to form oxides which act as either insulators or semi-conductors. Accordingly, grounding the feedthrough capacitor electrode plates directly to the titanium ferrule is contra-indicated. Reference is made to U.S. Pat. No. 6,465,779 (which is incorporated with this reference) which describes gold bond pad areas where the feedthrough capacitor external metallization can be directly connected to gold. The gold to which the feedthrough capacitor is directly connected is the braze material used to form the hermetic seal between the alumina and the titanium ferrule. As noted above, the hermetic seal is formed via a brazing process. By attaching the capacitor's ground plates to the gold, one can be assured that there will be no oxide that will increase the capacitor's equivalent series resistance (ESR) which can seriously degrade the capacitor's performance at high frequency. An undesirable aspect of using the gold braze for attachment is that gold is very expensive. Accordingly, there is a need for methods that provide a reliable low impedance ground path which is oxide resistant for grounding of AIMD filter capacitors. The present invention fulfills these needs and provides other related advantages.

SUMMARY OF THE INVENTION

An exemplary embodiment of a hermetically sealed filtered feedthrough assembly for an active implantable medical device (AIMD), includes: a) a ferrule of an electrically conductive material, the ferrule comprising a ferrule opening extending from a ferrule first end to a ferrule second end; b) an insulator of an electrically non-conductive material, the insulator comprising an insulator outer surface extending from an insulator first end to an insulator second end; c) an insulator metallization disposed at least partially on the insulator outer surface; d) a first braze hermetically sealing the insulator to the ferrule, the first braze formed between the ferrule and the insulator metallization of the insulator; e) a conductor hermetically sealed to and disposed through the insulator between the insulator first end and the insulator second end, the conductor in electrically non-conductive relation to the ferrule; f) a filter capacitor disposed near and/or on the insulator second end, the filter capacitor comprising: i) a capacitor dielectric comprising an dielectric outer surface extending from a first dielectric end to a second dielectric end; ii) at least one active electrode plate and at least one ground electrode plate disposed within and supported by the capacitor dielectric in an interleaved, partially overlapping relationship; iii) a first passageway disposed through the capacitor dielectric from the first dielectric end to the second dielectric end; iv) a capacitor internal metallization disposed within the first passageway electrically connected to the at least one active electrode plate and in non-conductive relation with the at least one ground electrode plate; v) a capacitor external metallization disposed at least partially on the dielectric outer surface, the capacitor external metallization electrically connected to the at least one ground electrode plate and in non-conductive relation with the at least one active electrode plate; g) an oxide-resistant metal addition, comprising: i) a conductive core; ii) a conductive cladding disposed on the conductive core, wherein the conductive core and the conductive cladding are different materials; h) a first electrical connection between the oxide-resistant metal addition and the capacitor external metallization; and i) a second electrical connection between the oxide-resistant metal addition and the ferrule.

In other exemplary embodiments, the second electrical connection between the oxide-resistant metal addition and the capacitor external metallization may be selected from the group consisting of a solder, a solder BGA, a solder paste, an epoxy, and a polyimide.

The second electrical connection between the oxide-resistant metal addition and the capacitor external metallization may be a laser weld or a second braze. The first and second brazes may comprise two brazes configured to reflow at different temperatures, the first braze comprising a higher temperature braze and the second braze comprising a lower temperature braze. The second braze may be selected from the group consisting of a low temperature gold alloy, a nano-gold preform and a fine gold wire with small grain size. The first braze may be disposed at or near the ferrule first end or the first braze may be disposed at or near the ferrule second end. The first braze may hermetically seal the insulator to the ferrule and also form the second electrical connection between the oxide-resistant metal addition and the ferrule.

The conductive core may be selected from the group consisting of stainless steel, MP35N and niobium. The conductive core may be selected from the group consisting of a solid material, a plurality of fibers twisted, braided and/or woven and a hollow tube. The conductive cladding may be selected from the group consisting of gold, palladium and platinum. A manufacturing process of the conductive cladding may be selected from the group consisting of a plating, an electroplating, a drawn filled tubing, a vapor or chemical deposition and an overcoating.

The oxide-resistant metal addition may be a plurality of oxide-resistant metal additions. The first electrical connection may be a plurality of first electrical connections. The feedthrough filter assembly of claim 1, wherein the second electrical connection may be a plurality of second electrical connections. The first electrical connection may be disposed a distance apart from the second electrical connection in a direction along a longitudinal length of the oxide-resistant metal addition.

The capacitor external metallization may be an adhesion metallization and a wetting metallization, wherein the adhesion metallization is disposed at least partially on the outer insulator surface and wherein the wetting metallization is disposed on the adhesion metallization.

An insulative washer may be disposed between the insulator and the filter capacitor.

The ferrule may be configured to be joined to an AIMD housing by a laser weld or braze or the ferrule may be formed from and as a continuous part of an AIMD housing.

The ferrule first end and the insulator first end may be associated with a body fluid side and the ferrule second end and the insulator second end may be associated with a device side.

The insulator first end and the ferrule first end may be oriented facing a same first direction, and wherein the insulator second end and the ferrule second end may be oriented facing a same second direction, the same first direction being opposite of the same second direction.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 29 is a perspective view of another exemplary feedthrough capacitor embodying the present invention;

FIG. 30 is a sectional view taken along line 30-30 of the structure of FIG. 29 cutting through two leadwires;

FIG. 31 is a perspective view of another exemplary feedthrough capacitor embodying the present invention;

FIG. 32 is a sectional view taken along line 32-32 of the structure of FIG. 31 cutting through two leadwires;

FIG. 48 is a perspective view of another exemplary feedthrough embodying the present invention now showing novel rectangular ground attachments in the ferrule;

FIG. 49 is a perspective view of another exemplary feedthrough embodying the present invention now showing novel circular ground attachments in the ferrule;

FIG. 60 is a sectional view similar to FIG. 58 now showing no gold brazes between the alumina insulator and the corresponding leads but rather a co-fired alumina ceramic;

FIG. 61 is a sectional view similar to FIG. 59 now with a substrate or circuit board;

FIG. 67 is an isometric view similar to FIG. 25, but now showing a cladded wire 218 as a metal addition;

FIG. 68 is an isometric view similar to FIG. 67, however now the metal addition is a multitude of metal additions;

DETAILED DESCRIPTION OF THE PREFERRED EMBODIMENTS

Figure 1:
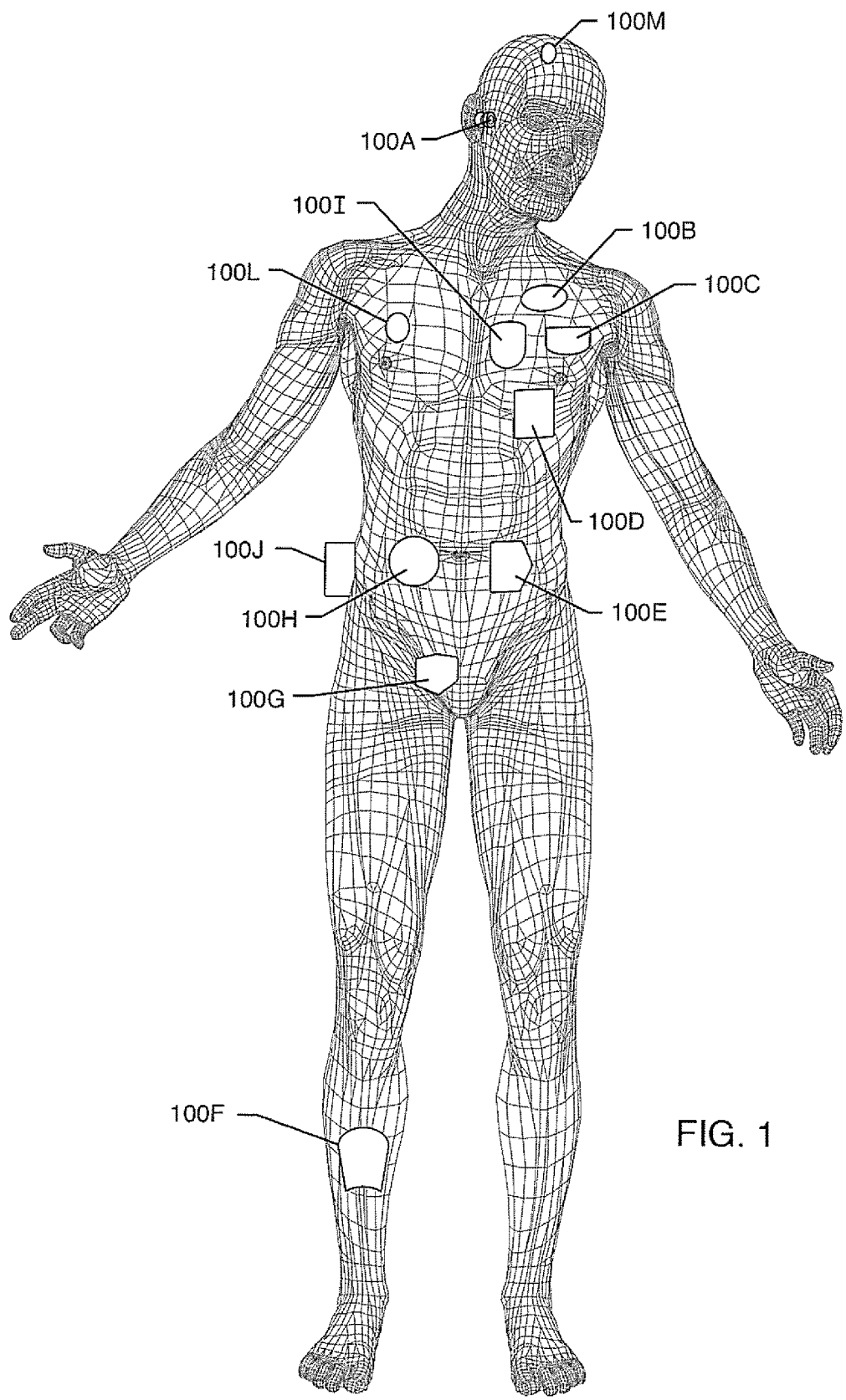
FIG. 1 illustrates a wire-formed diagram of a generic human body showing various types of active implantable and external medical devices currently in use.

FIG. 1 is a wire-formed diagram of a generic human body showing various types of active implantable and external medical devices 100 that are currently in use. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for example but not limited to sensing the onset of the seizure and also providing electrical stimulation to brain tissue to prevent the seizure from actually happening, or for treating memory loss, Alzheimer's and the like. The leadwires that come from a deep brain stimulator are often placed using real time imaging. Most commonly such leadwires are placed during real time MRI. 100C shows a cardiac pacemaker which is well-known in the art. 100D includes the family of left ventricular assist devices (LVAD's), and artificial hearts, including the recently introduced artificial heart known as the ABIOCOR. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack.

Figure 2:
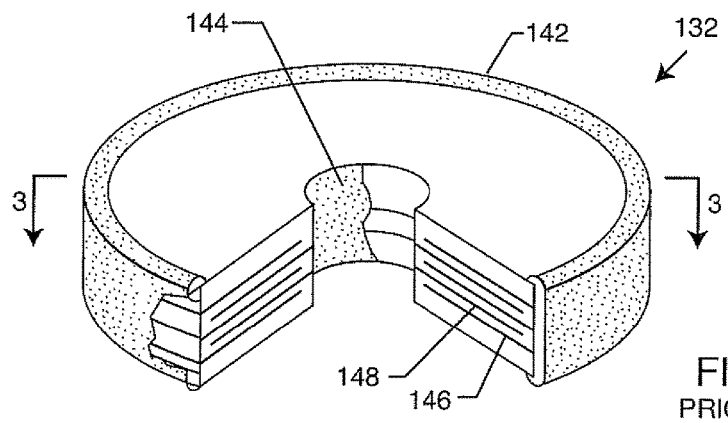
FIG. 2 is an isometric cut-away view of a unipolar feedthrough capacitor.

FIG. 2 is an isometric cut-away view of a unipolar feedthrough capacitor 132. It has an outside diameter metallization 142 and an inside diameter metallization 144. Active electrode plates 148 and ground electrode plates 146 are interleaved in the dielectric body. As can be seen, the active and ground electrode plates are generally parallel to one another. The active electrode plate set 148 is connected to the inside diameter metallization 144. The ground electrode plate set 146 is connected to the outside diameter metallization 142. Metallization surfaces 142 and 144 can be glass fritted platinum silver or various types of plating. The metallization surfaces 142 and 144 are very important as it is easy to make electrical connection of these surfaces to other circuit elements.

Figure 3:
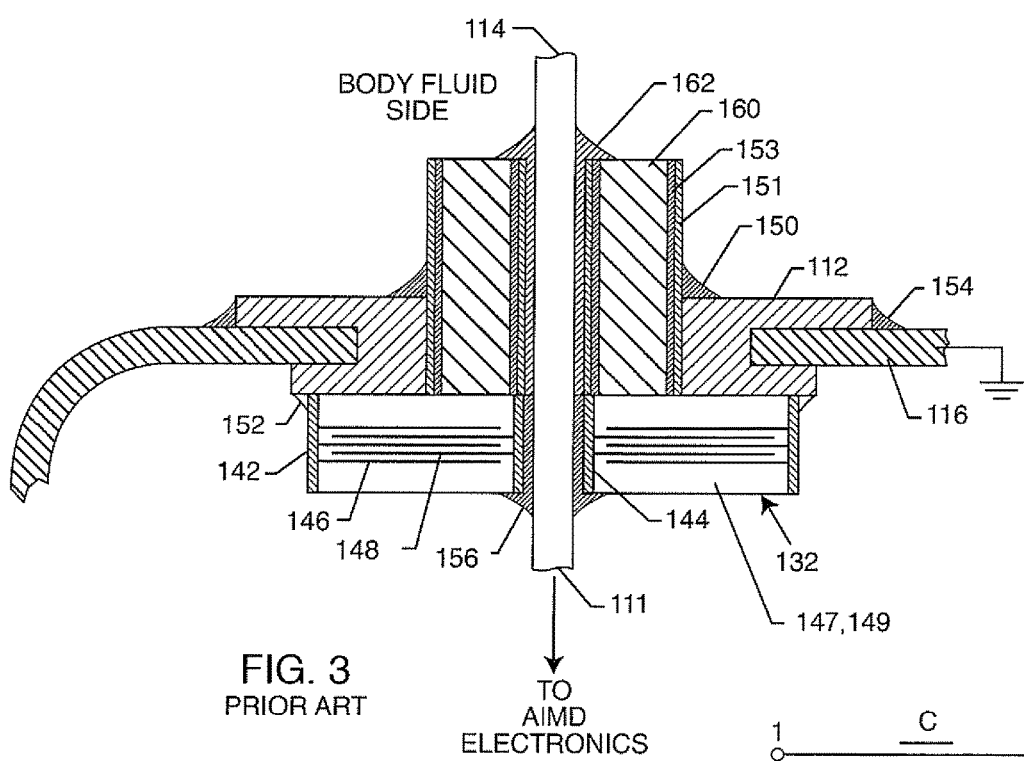
FIG. 3 is a cross-sectional view of the unipolar capacitor of FIG. 2 shown connected to the hermetic terminal of an AIMD.

FIG. 3 is a cross-sectional view of the unipolar capacitor of FIG. 2 shown connected to the hermetic terminal of an active implantable medical device, such as a cardiac pacemaker. Shown is a hermetic seal formed from an insulator 160, such as an alumina ceramic, glass or the like. A gold braze 162 forms a hermetic seal between the insulator 160 and leadwire 114, 111. The leadwire labeled 114 on the body fluid side is generally directed to an implantable lead that has an electrode contactable to biological cells (not shown). And there is a second gold braze 150 which hermetically connects the outside diameter of the insulator material 160 to a ferrule 112. To help form a hermetic seal between the insulator 160 and the leadwire 114 or ferrule 112, an adhesion layer 153 and a wetting layer 151 are used. Not shown is a typical first operation wherein the alumina ceramic 160 is first prepared by sputtering typically with a layer of molybdenum and then a layer of titanium. The first layer of molybdenum is the adhesion layer 153 and the second layer of titanium is the wetting layer 151 which provides for good wetting of the gold braze 162 or 150 to form the hermetic seal. In the prior art, the ferrule is generally of titanium. The AIMD housing 116 is also generally of titanium. The housing 116 also serves as an electrical ground represented by the ground symbol. A laser weld 154 is formed which connects the ferrule 112 to the AIMD housing 116 electrically and mechanically. The laser weld 154 also forms a hermetic seal. The unipolar feedthrough capacitor 132 of FIG. 2 is shown mounted directly to the hermetic seal insulator. An electrical connection 156 connects the capacitor inside diameter metallization 144 to leadwire 111. There is also an electrical connection material 152 connected directly to the ferrule 112 as shown. This electrical connection 152 is substantially inferior to the present invention and thus undesirable. As shown, an electrical connection is being made directly to the titanium surface 112. It is well known that titanium, particularly when brought to elevated temperatures, forms oxides. Oxides of titanium, for example, titanium dioxide is so stable, it is used as a paint pigment. It is also highly resistive and also has semi-conductive properties. For this reason, this creates an undesirable series resistance $R_{OXIDE}$ between the feedthrough capacitor and the ferrule 112 and/or AIMD housing 116.

Figure 4:
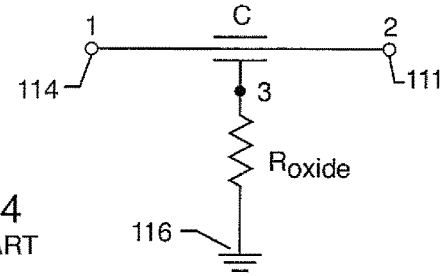
FIG. 4 is a schematic diagram of the unipolar feedthrough capacitor shown in FIGS. 2 and 3.

FIG. 4 is a schematic diagram of unipolar feedthrough capacitor shown in FIGS. 2 and 3. Shown is an ideal feedthrough capacitor C. In general, feedthrough capacitors are three-terminal devices in that there is an input side 114 (terminal one), an output side 111 (terminal two) and a ground 116 (terminal three). It is well known that an implanted lead can undesirably act as an antenna and couple to high frequency electromagnetic interference (EMI) energy. This EMI energy may be undesirably coupled along the implanted leadwire conductors to lead 111, which is directed to sensitive AIMD electronics. It is well known that EMI can disrupt the proper operation of AIMD electronic circuitry. For example, there have been a number of case reports of complete inhibition of cardiac pacemakers when EMI was falsely detected as a normal cardiac rhythm and the pacemaker inhibited. This is immediately life-threatening as its leaves a pacemaker dependent patient without a heartbeat during the entire time of the EMI exposure. The feature in the feedthrough capacitor as illustrated in FIGS. 2 and 3 is to divert incoming EMI energy in the implanted lead and dissipate it to the electromagnetically shielded housing 116 of the AIMD which said EMI energy may be dissipated as a harmless amount of thermal or RF energy. In other words, it is the job of feedthrough capacitors to protect the sensitive AIMD electronics while at the same time freely allowing pacing or therapeutic pulses to pass and also to allow the AIMD to sense biological signals that are generally in the frequency range from zero to 2000 Hz without interruption. The capacitor is also known as a frequency variable impedance element. The capacitive reactance $X_C$ in ohms is given by the equation:

$$X_C = 1/[2\pi f C]$$

wherein, f=frequency in hertz and C=the capacitance in farads. This inverse relationship with frequency means that, at very low frequencies, the capacitor looks like an open circuit (as if it were not there at all), and at very high frequencies, the capacitor acts as a short circuit where it diverts undesirable RF energy such as emissions from cellular telephones, microwave ovens or the like.

Referring once again to FIG. 4, one can see $R_{OXIDE}$. This resistive element is highly undesirable because it degrades the performance of the feedthrough capacitor all across its frequency range. There is also a great deal of variability in this oxide. During the gold brazing operation or during the formation of the hermetic seal, oxide poisoning may reach any corner or part of the brazing oven. The inventors have experienced some of the parts to be relatively oxide free where others in the lot may have a very thick or heavy oxide build-up.

Figure 5:
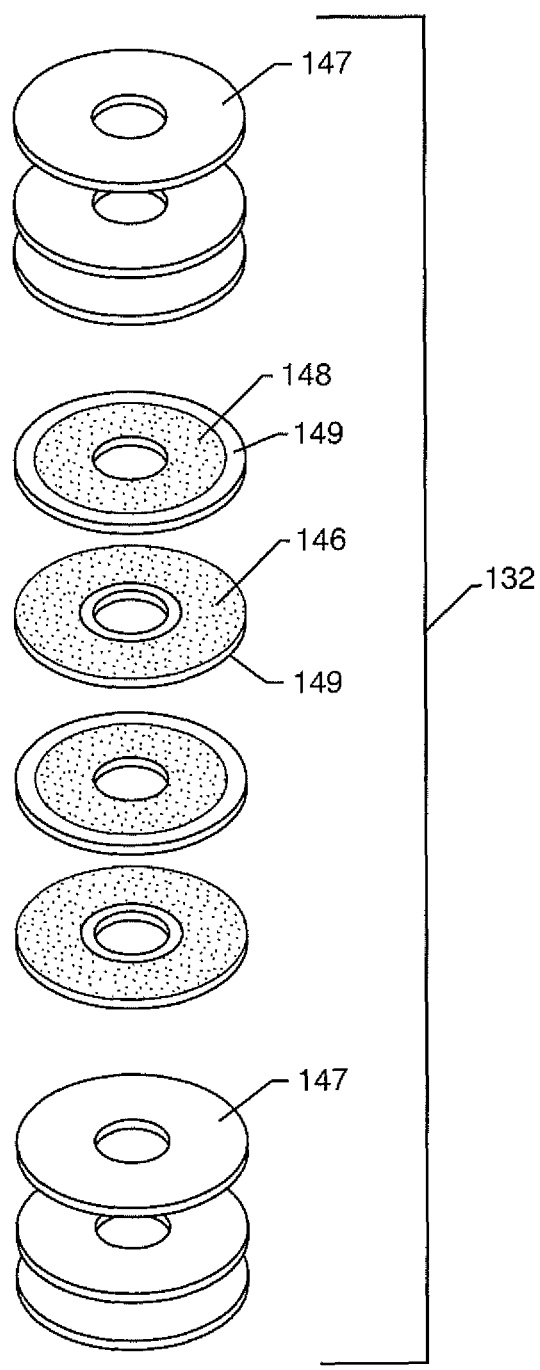
FIG. 5 is an exploded view of the cover sheets and internal electrodes of the unipolar capacitor previously described in FIGS. 2 and 3.

FIG. 5 is an exploded view of the cover sheets 147 and internal electrodes of the unipolar capacitor 132 previously described in FIGS. 2 and 3. One can see that there are active electrode plates 148 screened onto dielectric layers 149 and interleaved with ground electrode plates 146. A number of blank cover sheets 147 are placed on top and bottom for insulative and mechanical strength purposes.

Figure 6:
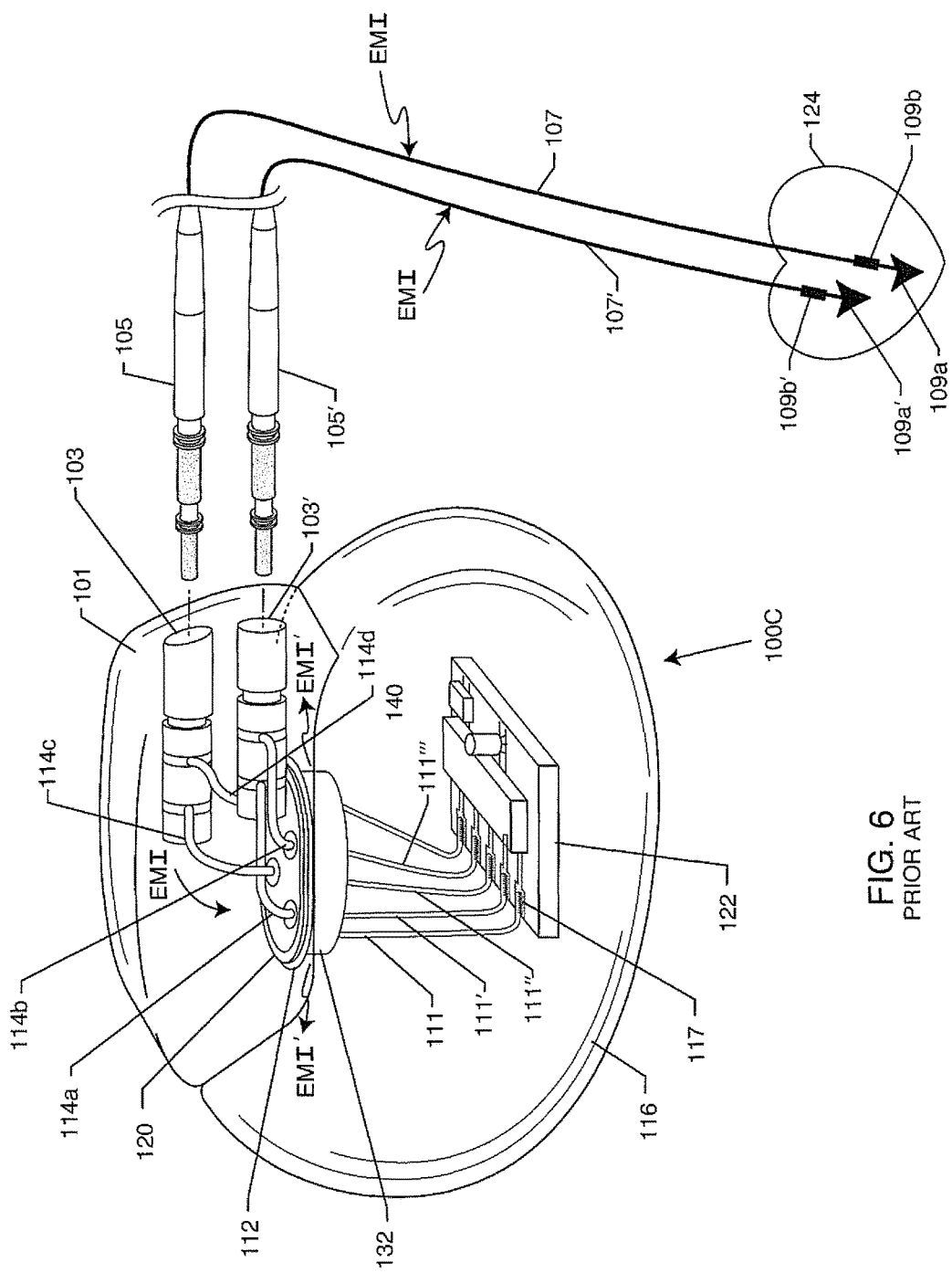
FIG. 6 is a diagrammatic perspective view of a typical AIMD.

FIG. 6 is a diagrammatic explosion of a typical AIMD, such as a cardiac pacemaker 100C. It has an overall electromagnetic shielded titanium housing 116 along with a polymer header block (connector block) 101. Shown, are two implantable leads 107 and 107', which in this case are directed to chambers of the heart 124. There are additional electrodes located at point 109a, 109b in the right ventricle and distal electrode 109a', 109b' located in the right atrium. In the art, this is known as a simple dual chamber bipolar pacemaker. As shown, EMI can be undesirably coupled to leads 107 and 107' where it can be conductive to the leadwires 114 of the hermetic seal assembly 120. The feedthrough capacitor element 132 diverts the EMI conducted on leads 114 into the conductive AIMD housing 116 where it is dissipated as eddy currents or RF energy (EMI) as simply coupled to surrounding body tissues. In any event, the EMI is prevented from reaching the delicate AIMD circuit boards 122. The leads 107, 107' have male connectors 105, 105' which are inserted into female connectors 103, 103' of the header block 101.

Figure 7:
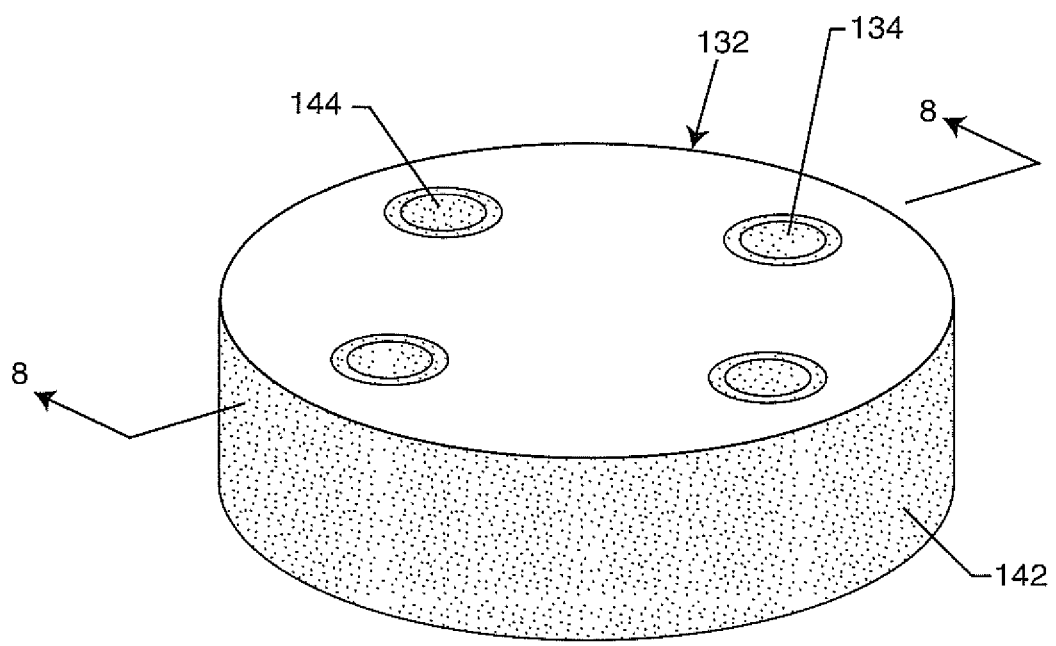
FIG. 7 is an isometric view of the quad polar feedthrough capacitor previously described in the prior art pacemaker of FIG. 6.

FIG. 7 is an isometric view of the quad polar feedthrough capacitor 132 previously described in the prior art pacemaker of FIG. 6. The quad polar feedthrough capacitor has an outside diameter metallization 142 and four feedthrough holes all of which have inside diameter metallization 144.

Figure 8:
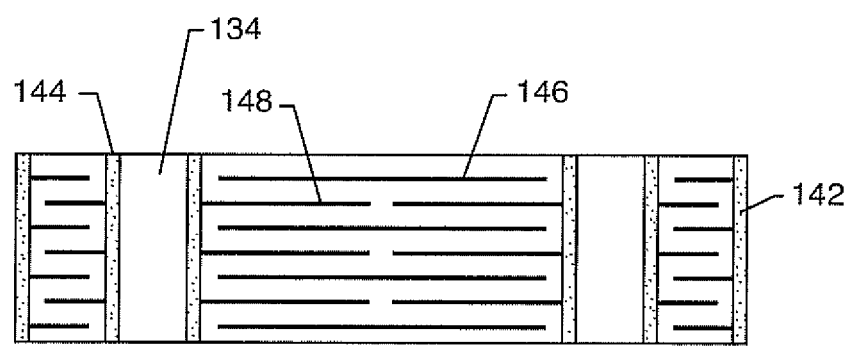
FIG. 8 is a sectional view taken from section 8-8 of FIG. 7 and illustrates the quad polar feedthrough capacitor interior electrode plates.

FIG. 8 is a sectional view taken from section 8-8 of FIG. 7 and illustrates the quad polar feedthrough capacitor interior electrode plates. There is a ground electrode plate set 146 which is coupled to the outside diameter metallization 142. There are four different sets of active electrode plates 148 which are each coupled to their own individual feedthrough hole 134.

Figure 9:
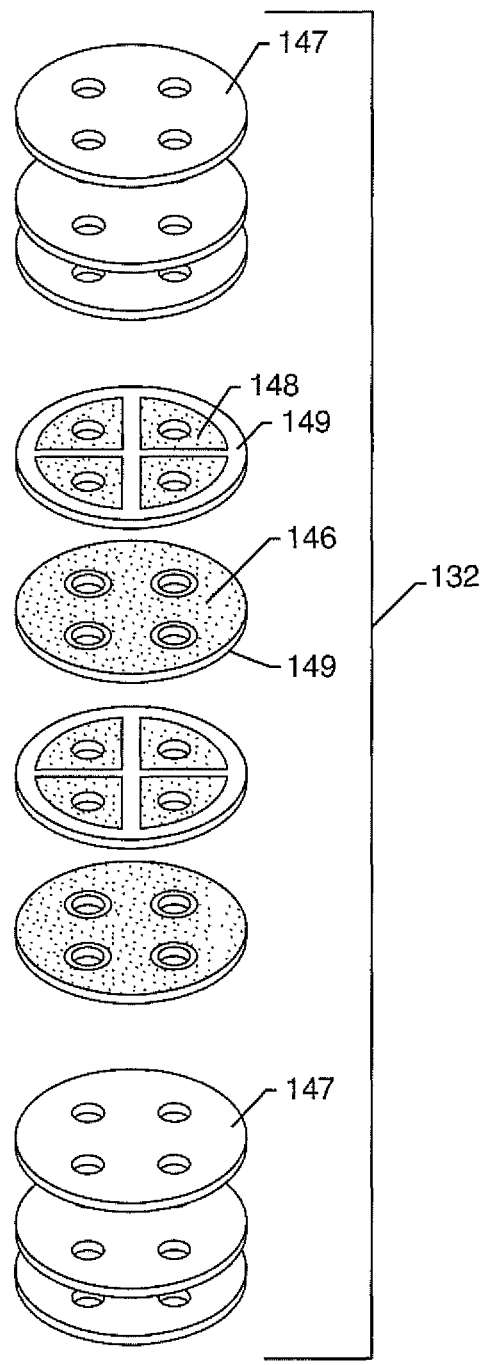
FIG. 9 is an exploded view of the quad polar feedthrough capacitor of FIG. 7.

FIG. 9 is an exploded view of the quad polar feedthrough capacitor of FIG. 7. Shown, are the four active electrode plate areas 148 and the ground electrode plates 146. As previously described, these active and ground electrode plates are in interleaved relationship. There are also a number of blank ceramic cover sheets 147 added on top and bottom for mechanical strength and electrical insulation. Those skilled in the capacitor art will understand that a higher voltage capacitor could be built by interleaving additional blank electrodes between the active and ground electrode plates thereby building up the dielectric thickness. Typically, the dielectric material could be of barium titanate ceramic and could vary in dielectric constant k anywhere from 50 all the way up to several thousand.

Figure 10:
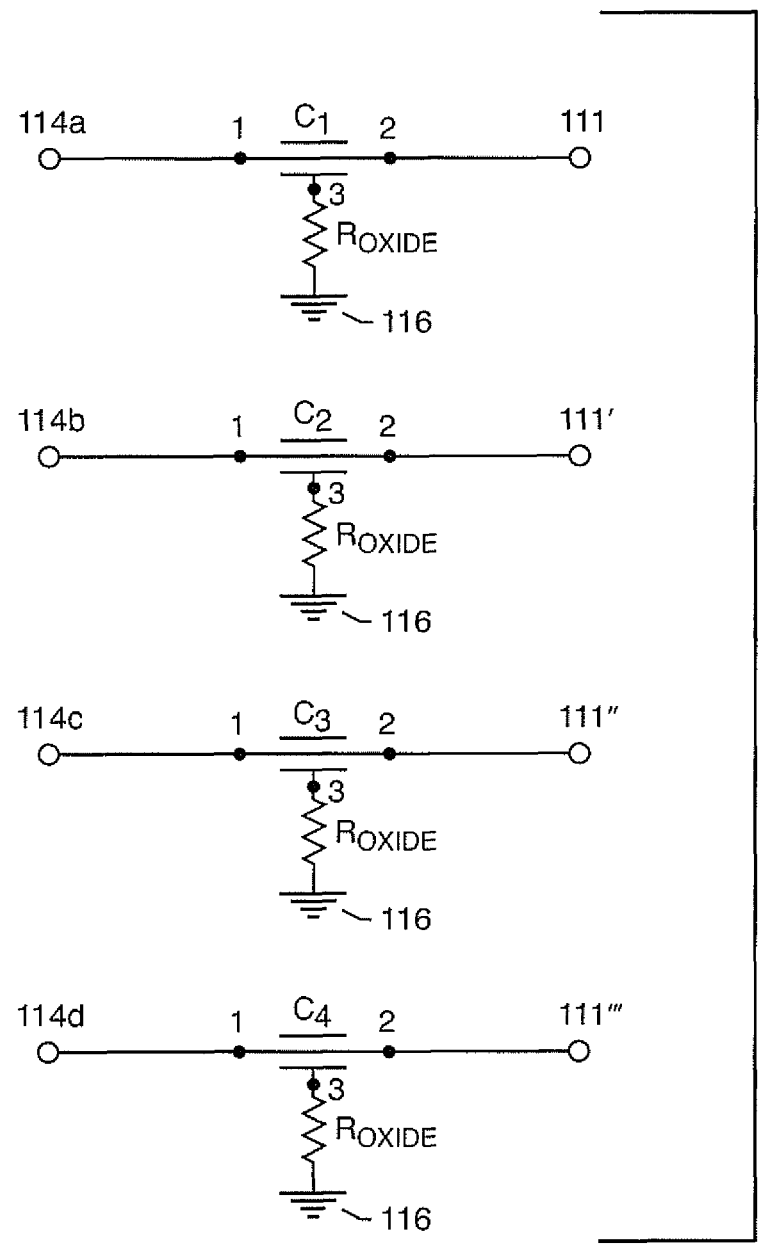
FIG. 10 is the schematic diagram of the quad polar feedthrough capacitor of FIG. 7.

FIG. 10 is the schematic diagram of the quad polar feedthrough capacitor of FIG. 6. Again, as previously described for the unipolar capacitor of FIG. 2 and FIG. 4, there is an undesirable resistance $R_{OXIDE}$ as shown. Ideally, feedthrough capacitors are three-terminal devices that have no series inductance or series resistance in their ground connection. This is why they make such effective broadband electromagnetic interference filters. In general, a feedthrough capacitor can provide attenuation over a very broad frequency range extending even to 18 to 20 GHz. However, this oxide is highly undesirable as it can seriously degrade filter performance. In general, filter performance is described by the terms insertion loss or by attenuation. Both of these are generally measured in a balanced 50 ohm system with the measurement units in decibels.

Figure 11:
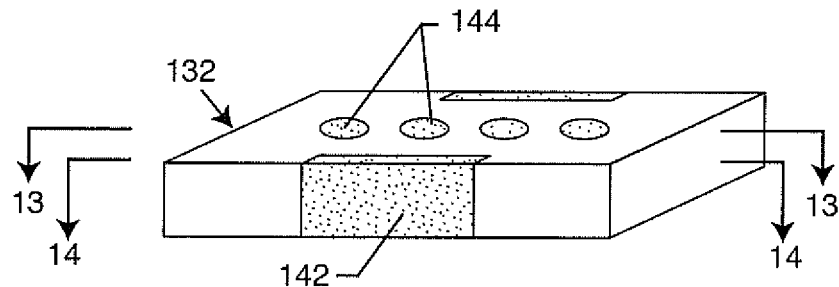
FIG. 11 illustrates a prior art quad polar feedthrough capacitor that is rectangular instead of round.
Figure 12:
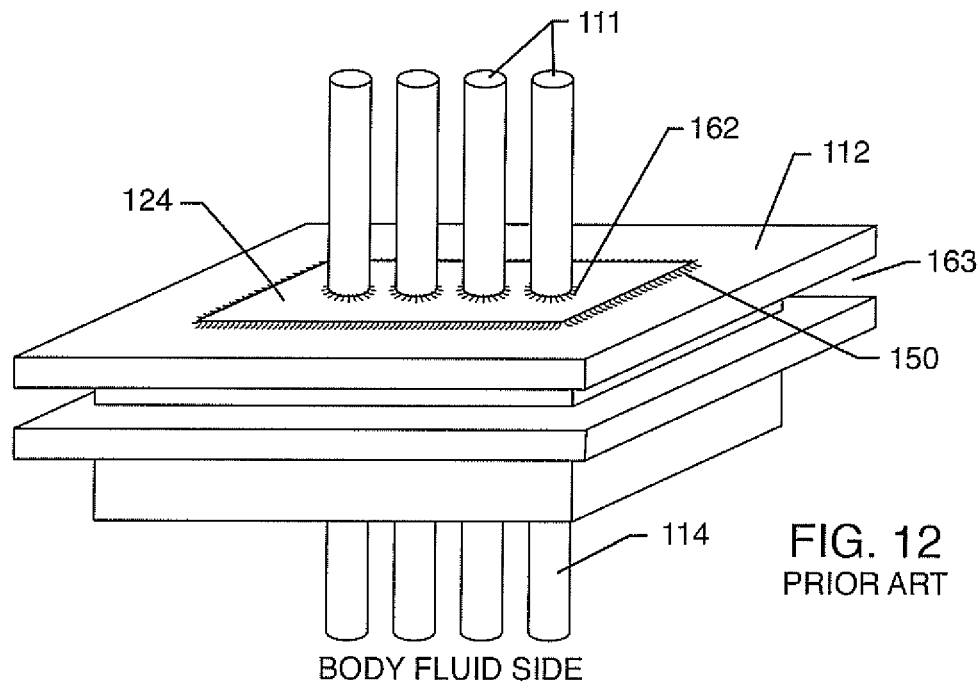
FIG. 12 is an isometric view of the feedthrough assembly before the feedthrough capacitor is placed on top.

FIG. 11 illustrates a prior art quad polar feedthrough capacitor that, in this case, is rectangular instead of round. It still has an outside metallization 142, but in this embodiment, instead of being all around a perimeter or outside diameter, it is shown only over a portion of the rectangular edge of the capacitor. In another embodiment (not shown) the outside metallization 142 could extend around the entire perimeter of the capacitor. Feedthrough metallization 144 is provided for each of the four feedthrough holes. FIG. 11 in combination with FIG. 12 illustrates an exploded assembly view wherein the capacitor of FIG. 11 is designed to be mounted atop a prior art quad polar hermetic terminal of FIG. 12. The hermetic terminal of FIG. 12 has four leadwires 111, 114, a hermetic insulator 124 and a ferrule 112, generally of titanium. There is a gold braze 150 which forms a hermetic joint between the ferrule 112 and the generally alumina ceramic insulator 124. There are four more gold brazes 162 which join leadwire 111 to the inside diameter holes of the hermetic insulator 124.

Figure 13:
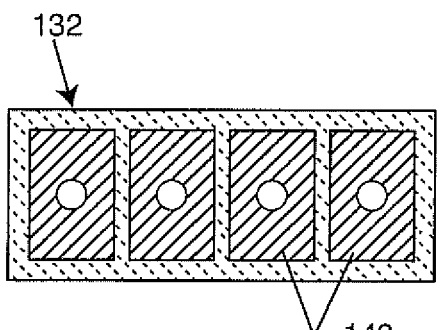
FIG. 13 is taken from section 13-13 from FIG. 11 showing the four active electrode plates.

FIG. 13 is taken from section 13-13 from FIG. 11. Shown are the four active electrode plates 148 of the feedthrough capacitor.

Figure 14:
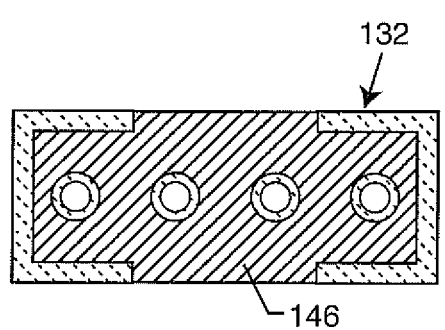
FIG. 14 is taken from section 14-14 from FIG. 11 and illustrates the ground electrode plate.

FIG. 14 is taken from section 14-14 from FIG. 11 and illustrates the ground electrode plate 146 of the feedthrough capacitor.

Figure 15:
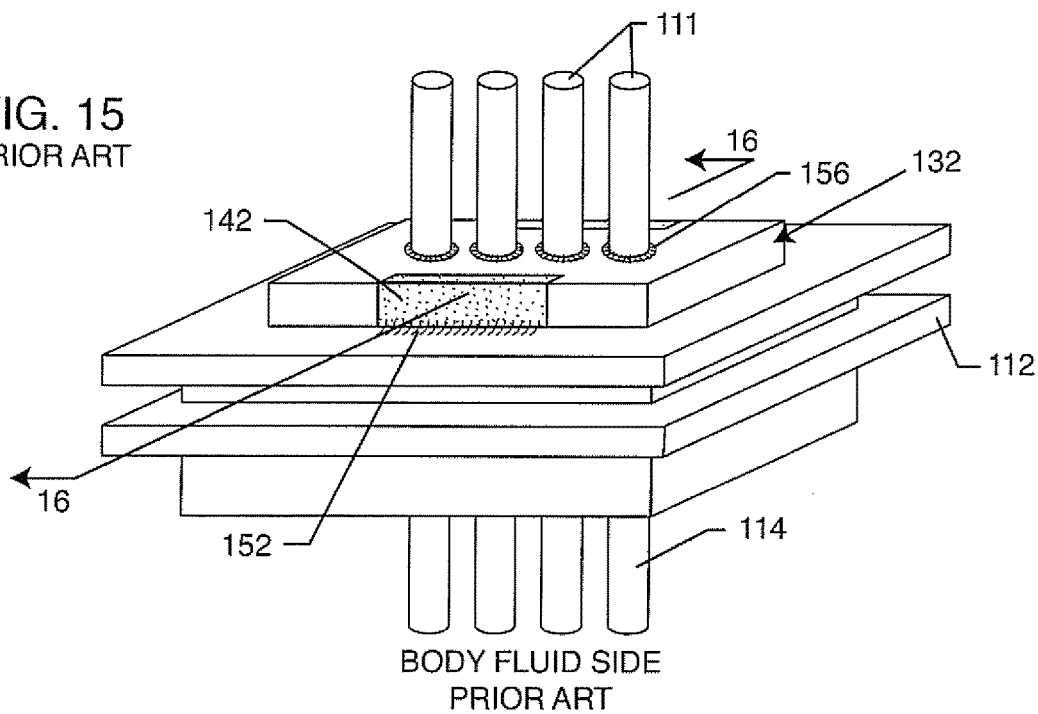
FIG. 15 is an assembly view taken from FIGS. 11-14 showing the quad polar rectangular feedthrough capacitor mounted onto the hermetic seal housing and the ferrule.

FIG. 15 is an assembly view taken from FIGS. 11 and 12 showing the quad polar rectangular feedthrough capacitor mounted onto the hermetic seal housing and the ferrule 112. An electrical connection 152 is generally made with a thermal-setting conductive adhesive between the capacitor metallization 142 directly to the ferrule 112.

Figure 16:
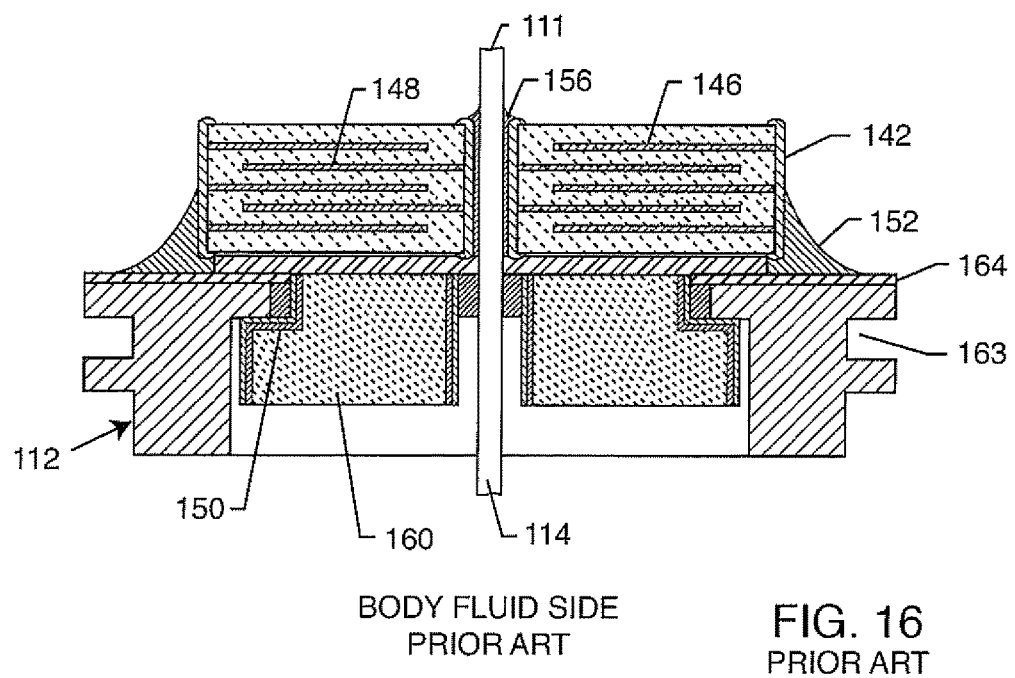
FIG. 16 is a sectional view taken from section 16-16 from FIG. 15 cutting through one of the leadwires.

FIG. 16 is a sectional view taken from section 16-16 from FIG. 15. This sectional view goes through one of the leadwires 111 and shows the interior ground electrode plate set 146 and the active electrode plate set 148. The ground electrode plates 146 make electrical and mechanical contact to the capacitor ground metallization 142. There is an electrical connection 152 shown directly to the top surface of the titanium ferrule 112. There is a cross-hatched area 164 which shows the formation of a very undesirable layer of titanium oxides. For simplicity, this layer is shown only on the top surface, but in reality, it would coat all of the surfaces of the titanium cross-section. As previously mentioned, the formation of this oxide can happen during initial gold brazing, during subsequent storage and handling of the overall filter feedthrough subassembly, or during laser welding of the ferrule 112 into the AIMD housing 116. One particular problem is that the thermal-setting conductive adhesive 152 always contains a certain amount of available oxygen. When a laser weld is formed to the AIMD housing, which is positioned to be placed in slot 163, this significantly raises the temperature of thermal-setting conductive adhesive 152. This is why a thermal-setting conductive polyimide is the connection material of choice, as a conductive polyimide is stable at temperatures well above 300 degrees C. This is in comparison to most epoxies which are only rated to about 230 degrees C. When this assembly is raised through laser welding to high temperature, oxygen can be released from a thermal-setting conductive material 152 and then be formed as a titanium dioxide or trioxide 164 on the ferrule 112 of the hermetic seal.

Figure 17:
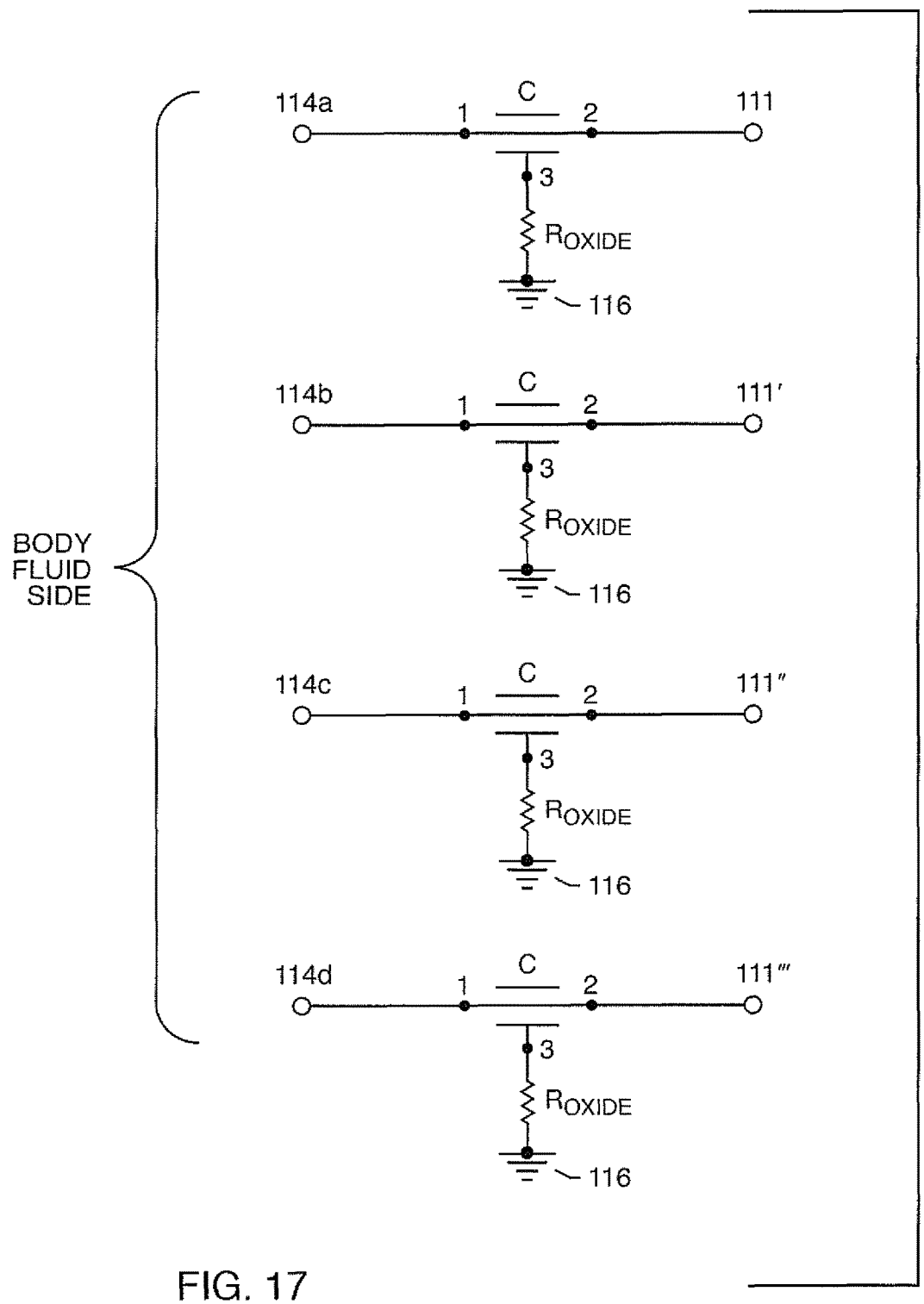
FIG. 17 is the electrical schematic diagram of the quad polar feedthrough capacitors previously illustrated in FIGS. 14 and 15.

FIG. 17 is the schematic diagram of the quad polar feedthrough capacitors previously illustrated in FIGS. 11, 15 and 16. Shown, is the undesirable $R_{OXIDE}$ which is shown in series between the ideal feedthrough capacitor and ground, which is the same electrical potential as the AIMD housing 116. As will be shown, the presence of this resistive oxide seriously degrades the filter performance.

Figure 18:
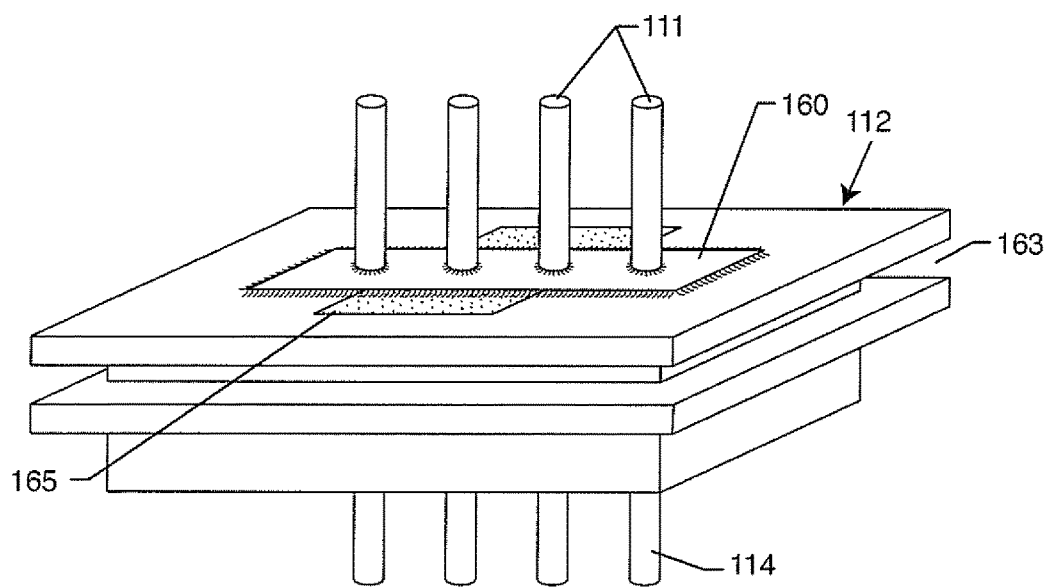
FIG. 18 is a perspective view showing gold bond pads used to eliminate the problem of attachment to oxides of titanium between the feedthrough capacitor outside diameter and its ground electrode plate sets.
Figure 20:
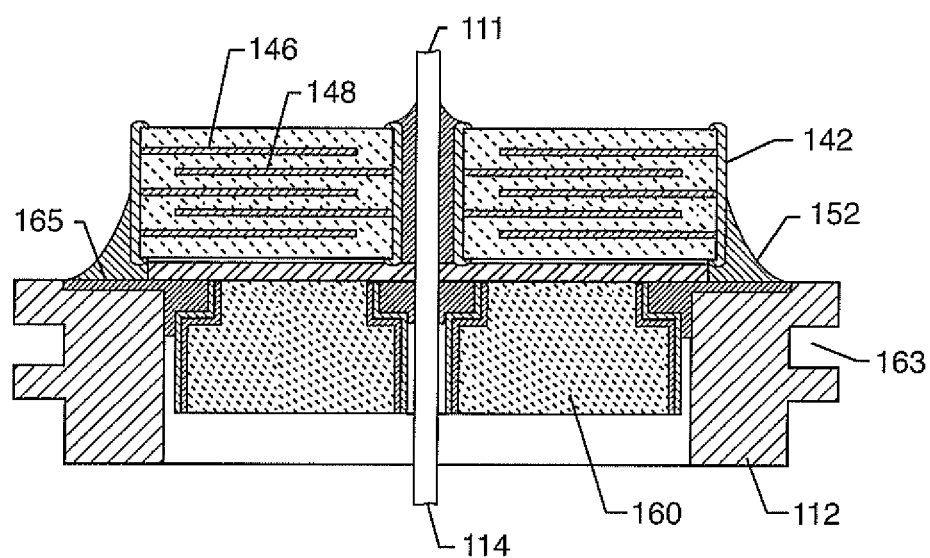
FIG. 20 is a sectional view of the structure of FIG. 19 taken through lines 20-20.

FIG. 18 is taken from FIG. 20 of U.S. Pat. No. 6,765,779 which describes gold bond pads to eliminate the problem of attachment to oxides of titanium between the feedthrough capacitor outside diameter and its ground electrode plate sets. Referring to FIG. 18, one can see that there are novel gold braze pads 165 that have been added. Referring to FIG. 12, one can see that these gold braze pads 165 are not present.

Figure 19:
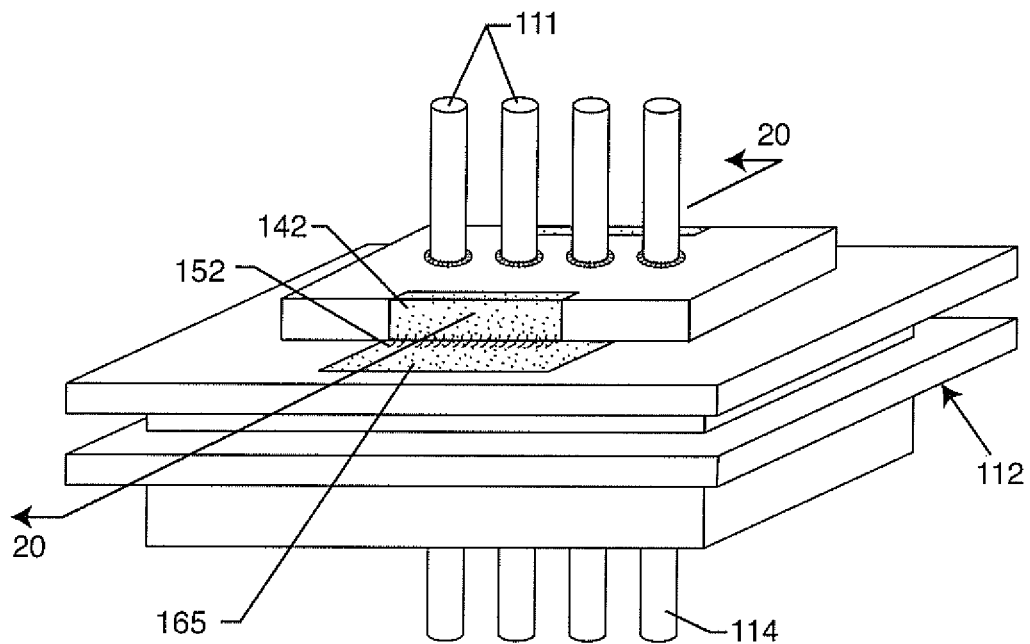
FIG. 19 shows that the electrical connections between the capacitor's ground metallization is now directly connected to the oxide resistant noble pad.

FIG. 19 shows that the electrical connections 152 between the capacitor's ground metallization 142 is now directly made to this non-oxidizable noble pad 165. U.S. Pat. No. 6,765,779 is incorporated herein by reference. As is shown in the '779 patent, one possible material for the oxide resistant pad 165 is gold. This gold pad 165 is continuous and is co-formed at the same time the hermetic seal (gold braze) is made to the alumina ceramic insulator 160. In fact, this is a limitation of U.S. Pat. No. 6,765,779 in that the gold bond pad 165 is always formed as part of the co-braze to the alumina ceramic insulator 160.

FIG. 20 is generally taken from section 20-20 from FIG. 19. It is very similar to FIG. 16 except that the gold braze area 165 has been enlarged to include the gold bond pad area 165. Pure gold has a high melting point (1064° C.) which is above the allotropic transformation temperature of titanium (883° C.). Titanium is soluble in gold, particularly more so at elevated temperature. Elevated temperature maximizes titanium dissolution into gold. As previously noted, titanium is highly reactive to air readily forming surface oxides. Brazing to titanium, therefore, is generally performed at high vacuum. At high vacuum brazing temperatures, when a gold brazed joint 164 is formed between, for example, a gold braze preform and a titanium ferrule, the titanium reacts with the gold to form a direct metallurgical bond to the titanium ferrule 112. As this direct metallurgical bond is gold-rich, it essentially retains the high conductivity of the gold and its oxide resistant properties. In this regard, the enlarged gold braze area surface, that is, the bonding pad that is formed is part of the oxide-resistant metallurgical bond (oxide-resistant also means oxide-free for the most part as any oxides that are formed are very minimal). This enlarged gold braze area serves as the electrical connection material that is connectable to the capacitor ground metallization 142. To summarize, a continuous electrical connection that is consistent in its conductivity over the service life of the device is made. The electrical connection is between the titanium ferrule 112 and the filter capacitor ground metallization 142 via the electrical connection material 152 directly to the non-oxidizable pad 165.

Figure 21:
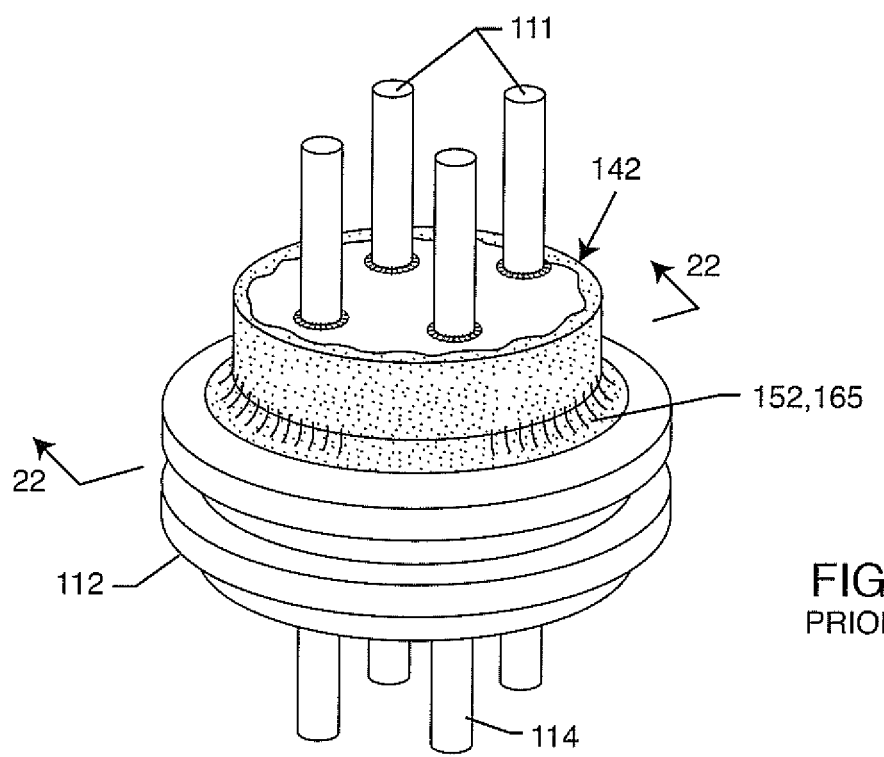
FIG. 21 is very similar to FIG. 19, except that the quad polar capacitor is round which is consistent with the feedthrough capacitor previously illustrated in the cardiac pacemaker of FIG. 6.

FIG. 21 is very similar to FIG. 19, except in this case, the quad polar capacitor is round which is consistent with the feedthrough capacitor 132 previously illustrated in the cardiac pacemaker of FIG. 6.

Figure 22:
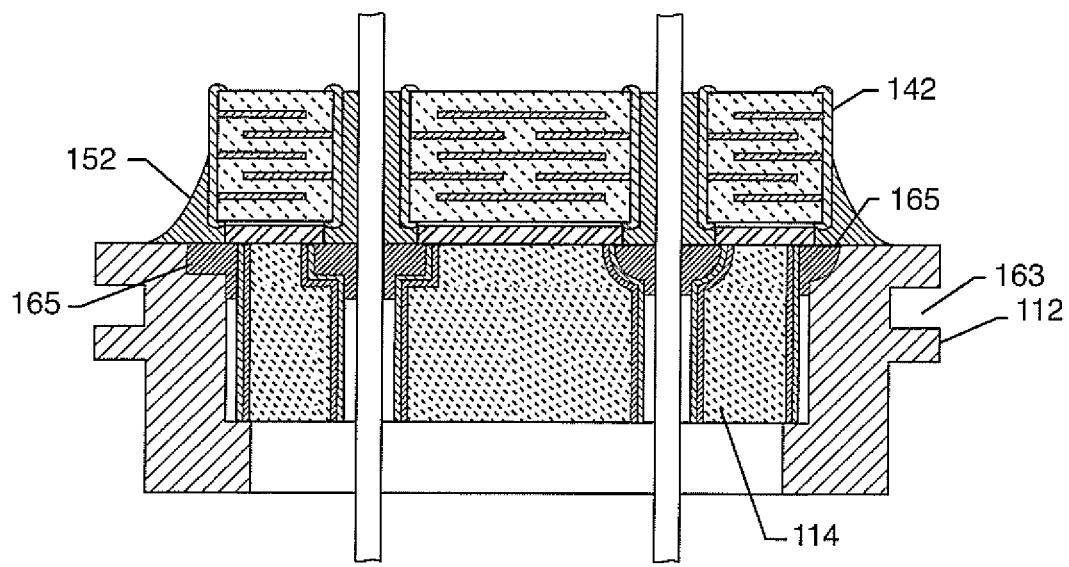
FIG. 22 is generally taken from section 22-22 from FIG. 21 cutting through two leadwires and illustrates the capacitor's internal structure including its ground and active electrode plates.

FIG. 22 is generally taken from section 22-22 from FIG. 21 and illustrates the capacitor's internal structure including its ground and active electrode plates. Importantly, outside diameter electrical connection material 152, which connects the outside diameter metallization 142 to the ferrule 112, is directly attached to the gold braze material 165. The fact that some of this overlaps onto the titanium surface is not important. What is critical is that a suitable amount of the electrical connection material 152 is directly attached to an oxide resistant noble surface, so that an undesirable resistance can never develop.

Figure 23:
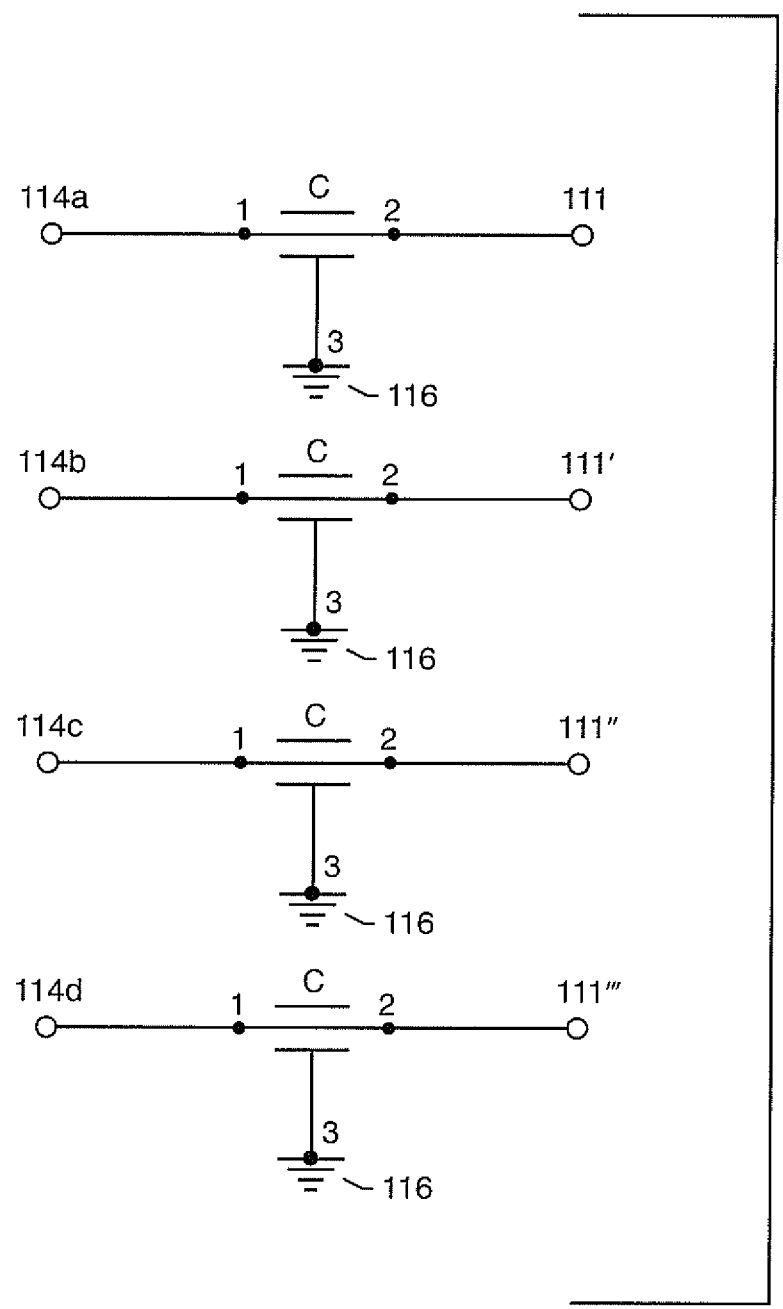
FIG. 23 illustrates the electrical schematic diagram of the improved rectangular quad polar feedthrough capacitor of FIG. 19 and the round quad polar capacitor of FIG. 21.

FIG. 23 illustrates the schematic diagram of the improved rectangular quad polar feedthrough capacitor of FIG. 19 and the round quad polar capacitor of FIG. 21. One can see that we now have insignificant resistance in the connection from the feedthrough capacitor to ground 116, which is the overall shielded equipotential surface of the electromagnetically shielded housing 116.

Figure 24:
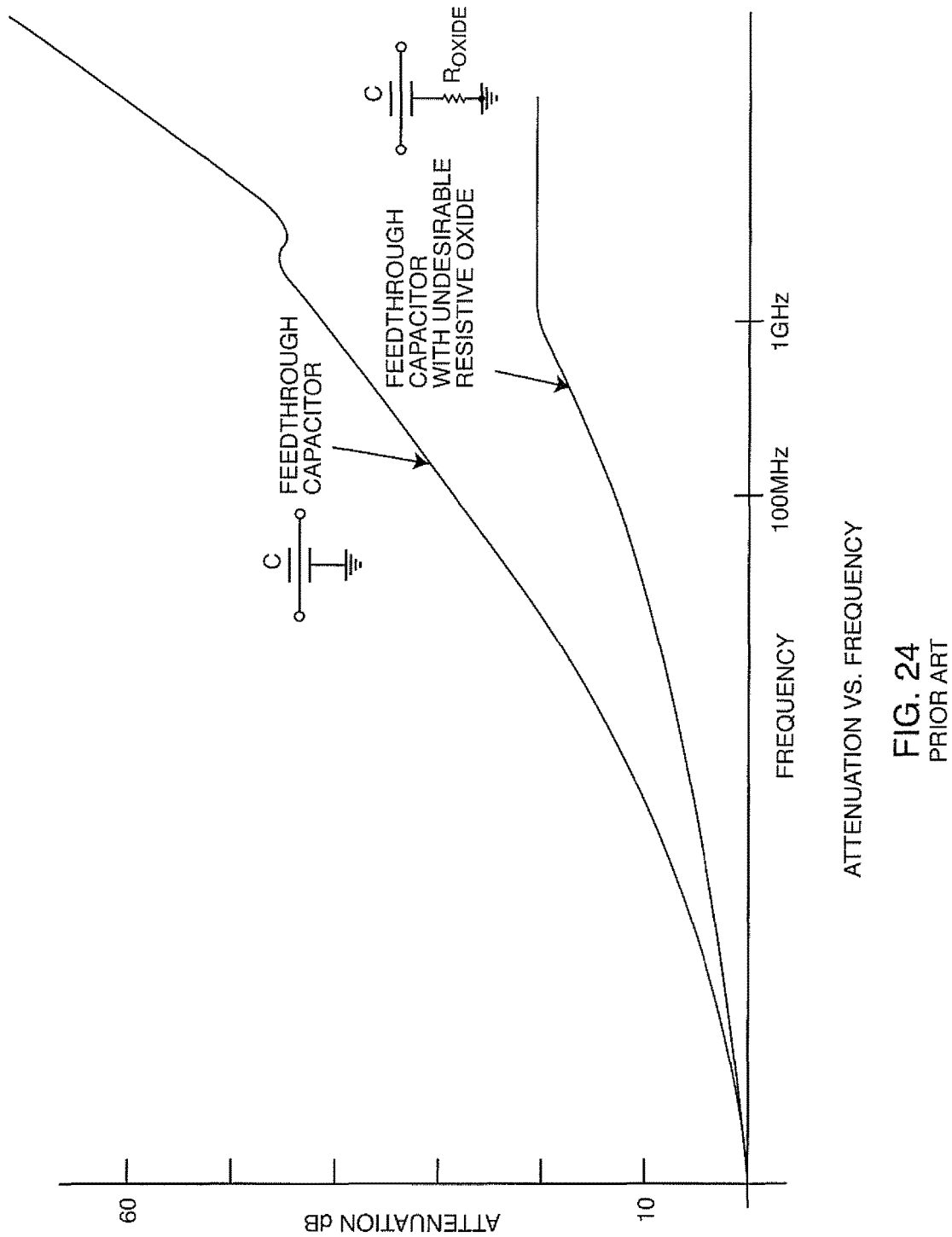
FIG. 24 illustrates attenuation versus frequency comparing the ideal feedthrough capacitor to one that has undesirable ground electrode plate connection to an oxidized surface.

FIG. 24 is attenuation versus frequency curves which compares the ideal feedthrough capacitor to one that has undesirable ground electrode plate connection to an oxidized surface. One can see that the feedthrough capacitor with the resistive oxide $R_{OXIDE}$ has greatly reduced attenuation all across the frequency band as compared to the ideal feedthrough capacitor.

Figure 25:
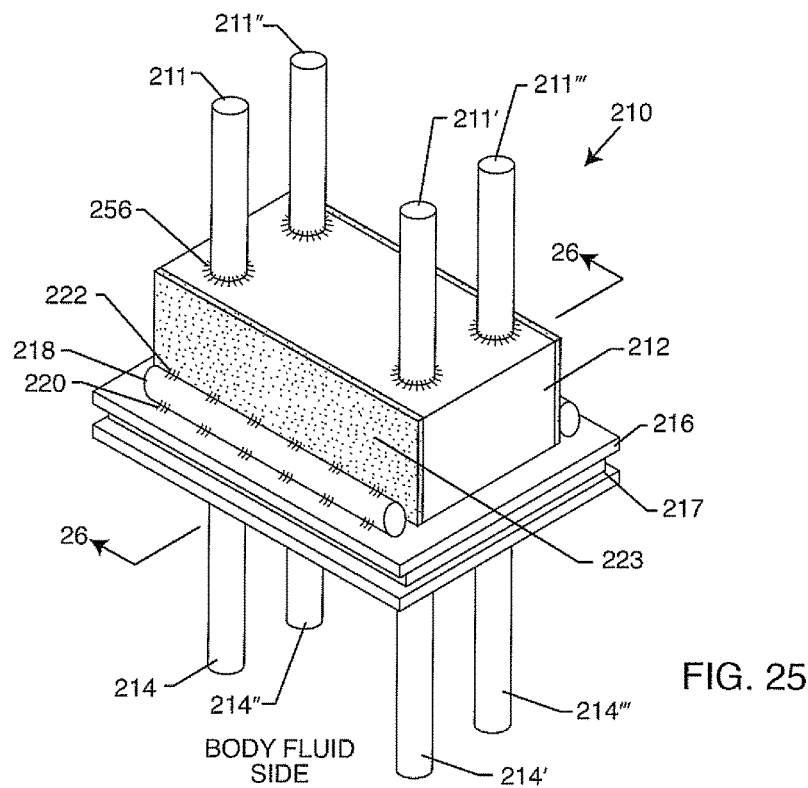
FIG. 25 is a perspective view of an exemplary feedthrough capacitor embodying the present invention.

FIG. 25 illustrates an embodiment of a filtered feedthrough assembly of the present invention 210. Illustrated is a ferrule 216 of the hermetic seal. The ferrule 216 is generally of titanium. In this case, it has a continuous slot 217, which can receive the can halves of an active implantable medical device, such as a cardiac pacemaker. These titanium can halves are then laser welded to the titanium ferrule 216. In general, a feedthrough capacitor 212 would be oriented towards the inside of the can to protect it from body fluids. In this case, there are novel round platinum iridium wires 218, which have been laser welded 220 directly to the ferrule 216. Laser weld 220 could also be replaced by a resistance weld or a secondary braze operation at a lower temperature using for example, but not limited to, copper based brazing materials such as Cu-Sil or Ti—Cu-Sil, silver based brazing materials such as Silvaloy (Ag—Cu—Zn) or Gapasil (Ag—Pd—Ga), gold based brazing materials such as Au—Cu, Au—Cu—Ag, or Au—Cu—Ni, or palladium based braze materials such as Pd—Ni—Si. A capacitor ground metallization 223 is attached using solder or thermal-setting conductive adhesives 222 to the platinum iridium wire 218. The platinum iridium wire can actually be of any noble material including platinum, gold, palladium, silver, ruthenium, rhodium, osmium, iridium, alloys based on each of these noble metals and combinations thereof. Leadwires 211 through 211''' pass through the feedthrough capacitor and through the hermetic seal. This is best understood by referring to FIG. 26, which is taken from section 26-26 from the structure of FIG. 25.

Figure 26:
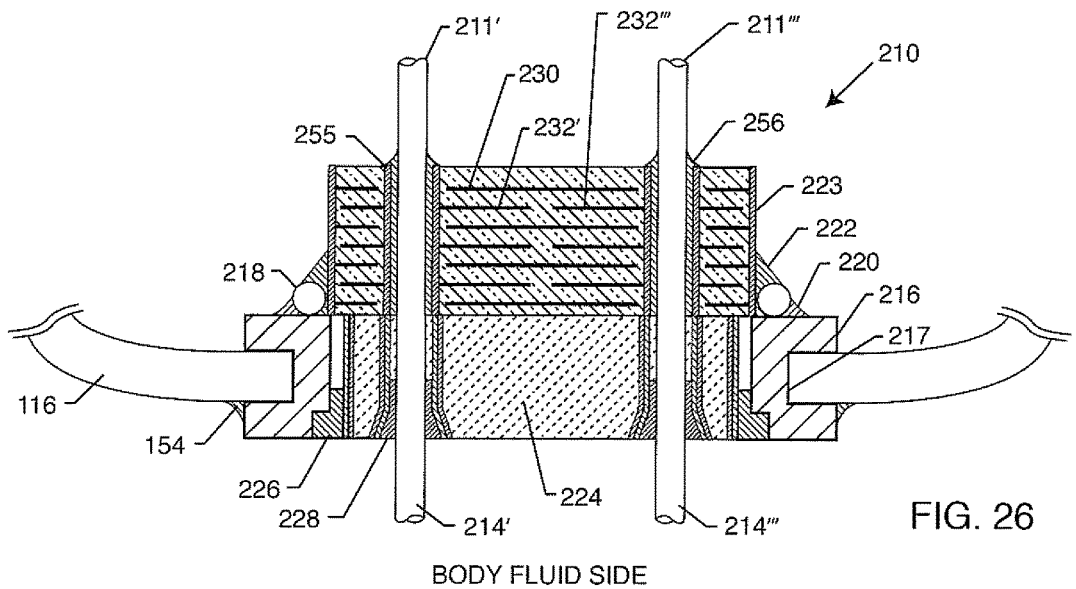
FIG. 26 is a sectional view taken along line 26-26 of the structure of FIG. 25.

FIG. 26 illustrates the laser weld 220, the noble wire 218 and the solder or thermal-setting conductive adhesive 222. In FIG. 26, one can see the capacitor interior electrode plate stacks. A ground electrode plate stack 230 and an active electrode plate stack are designated by 232' and 232' which are connected respectively to terminal pins 211' and 211'. It is understood by one skilled in the art that various structures and techniques are used to connect the active electrode plates to the leadwires. On the body fluid side of the capacitor, one can see gold brazes 226 and 228. Gold braze 226 connects the ferrule 216 to the alumina insulator 224 providing a robust mechanical and hermetically sealed joint. Gold braze 228 forms a robust mechanical and hermetic seal between the alumina ceramic 224 and the leads 211. An electrical connection 256 connects the capacitor inside diameter metallization 255 to the leadwire 211.

Referring once again to FIGS. 25 and 26, one can see that the leadwire 218 provides a very novel feature, that is, electrical connection material 222 does not directly attach to the ferrule 216. The reason for this is that the ferrule is typically of titanium, which commonly forms titanium oxides. Titanium oxides are very resistive and can also act as semi-conductors. This means that a direct connection to titanium would degrade the effectiveness of the capacitor ground electrode plate stack. The noble wire 218 acts as an intermediate surface. By laser welding 220 the wire 218 to the titanium ferrule 216, one forms a very strong oxide resistant metallurgical bond. Now, the surface on wire 218 is relatively oxide free. For example, it could be gold, platinum, palladium, silver, ruthenium, rhodium, osmium, iridium, alloys based on each of these noble metals and combinations thereof which are oxide resistant at room temperatures. In fact, the wire 218 could be pure platinum and not platinum iridium. The reason for this is that the iridium can form undesirable oxides.

Referring once again to FIG. 26, shown is that the gold brazes forming the hermetic seals 226 and 228 are on the body fluid side. There are a number of AIMD manufacturers that prefer having the gold braze on the body fluid side. By having the gold braze in this location, however, making a connection to the capacitor's outside perimeter or diameter metallization 223 to the same gold braze surface becomes impossible. In other words, as previously described in FIG. 18, there is no possibility to provide the gold bond pad 165, which is a contiguous part of the hermetic seal braze 226. This is a major driving feature of the present invention in that a methodology is provided so that the feedthrough capacitor can be properly grounded to an oxide resistant surface even when the gold brazes are disposed on the opposite side (opposite the body fluid side).

Referring back to FIG. 26, one can see that there is an electrical pathway described as the electrical path from the capacitor internal ground electrode plate set 230, then through the capacitor peripheral or exterior metallization 223, and then through the electrical connection material which would have an a total resistance of less than 5-milliohms and a total inductance of less than 10 nanohenries. In another embodiment, total resistance of this grounding path would be less than 1-milliohm and the total inductance would be less than 1 nanohenry. As used herein, the definition of the term "grounding pathway" is the aforementioned grounding pathway extending from the capacitor internal electrode plates all the way to the AIMD conductive housing 116.

Figure 27:
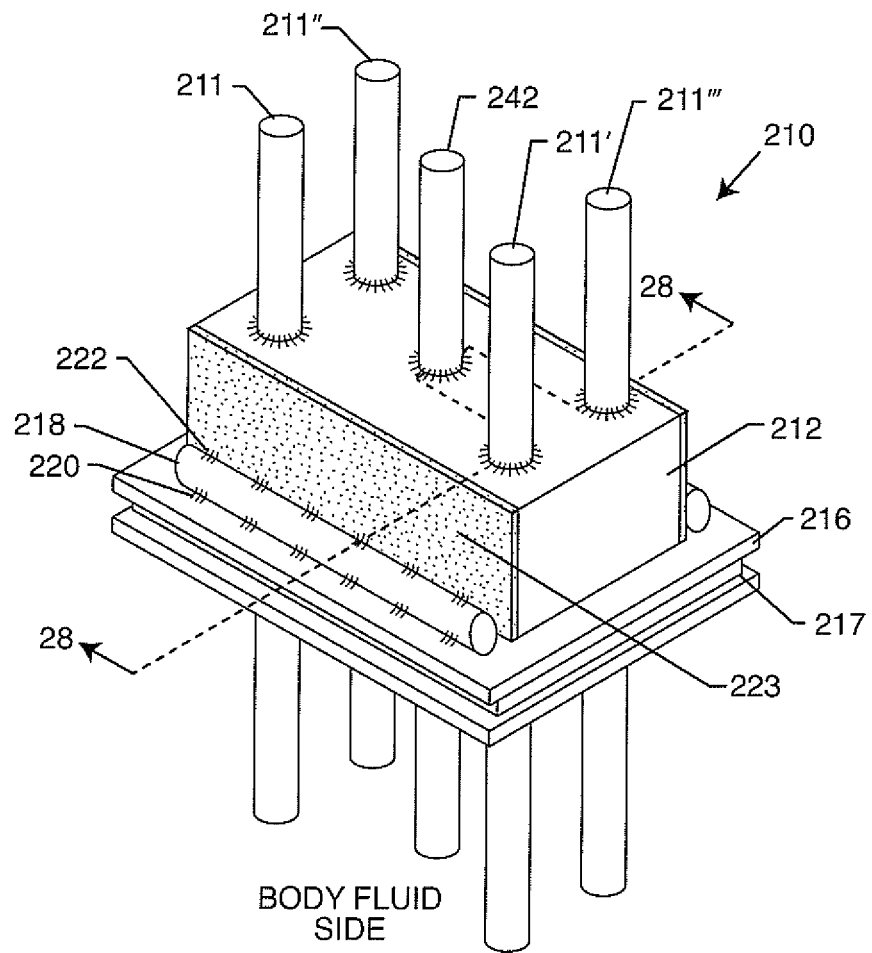
FIG. 27 is a perspective view of another exemplary feedthrough capacitor embodying the present invention.
Figure 28:
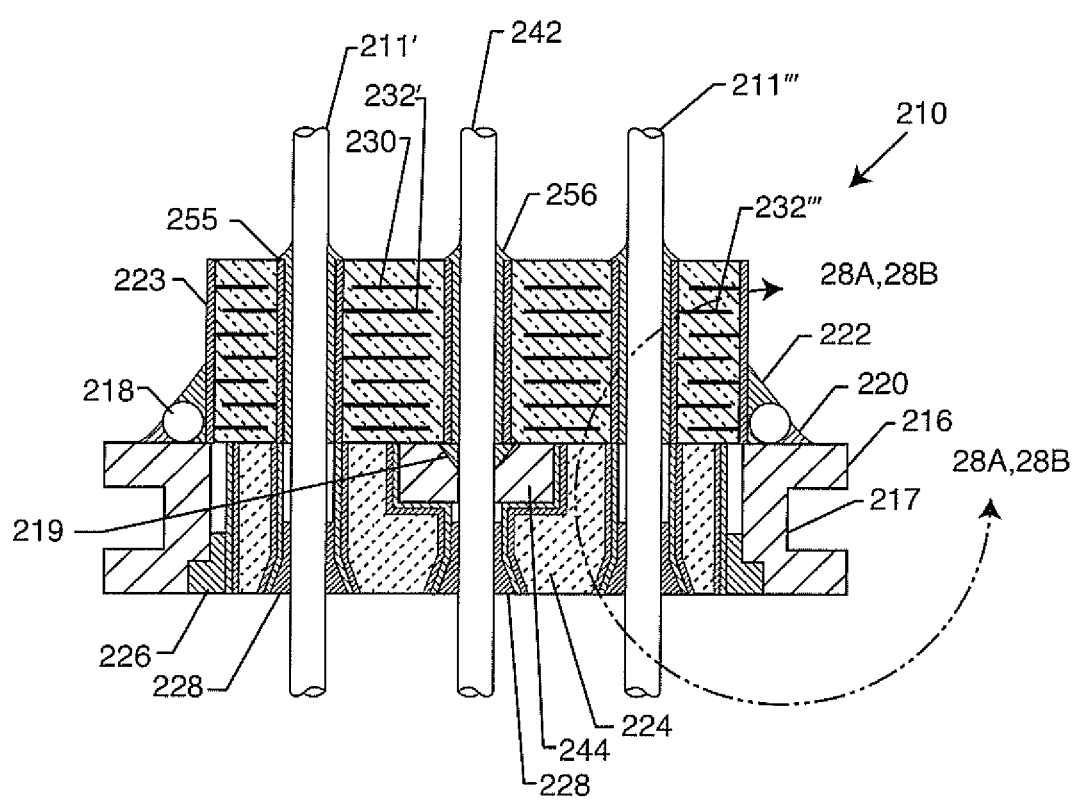
FIG. 28 is a sectional view taken along line 28-28 of the structure of FIG. 27.

FIGS. 27-28 are similar to FIGS. 25-26 but now show a peninsula structure 244 formed as part of the ferrule 216. A ground wire 242 is attached to the peninsula 244. As can be seen best in the cross-section of FIG. 28, the ground wire 242 is not connected to the ground electrode plates 230. The ground electrode plates are still electrically coupled to the metallization 223 which is then electrically coupled to the ferrule 216 through the weld 220, the wire 218 and the thermosetting conductive adhesive 222 or solder.

Referring once again to FIG. 27A, one can see that the grounded peninsula 244, which is a continuous part of the machined ferrule 216, is electrically attached via material 219 to the grounded pin 242. The ground material could be a laser weld, a gold braze, a solder, a thermal-setting conductive adhesive or the like. In general, pin 242 is provided as a convenience to the AIMD manufacturer to either ground the internal circuit board, or to provide an addition pacing vector to a conductor of an implanted lead (not shown) or both. The electrical ground attachment from the peninsula 244 to lead 242 is very low in resistivity, meaning that it would also be applicable for high voltage implantable cardioverter defibrillator applications. In such an application, a very high shock current would flow through this ground joint to an external electrode (not shown).

Figure 28A:
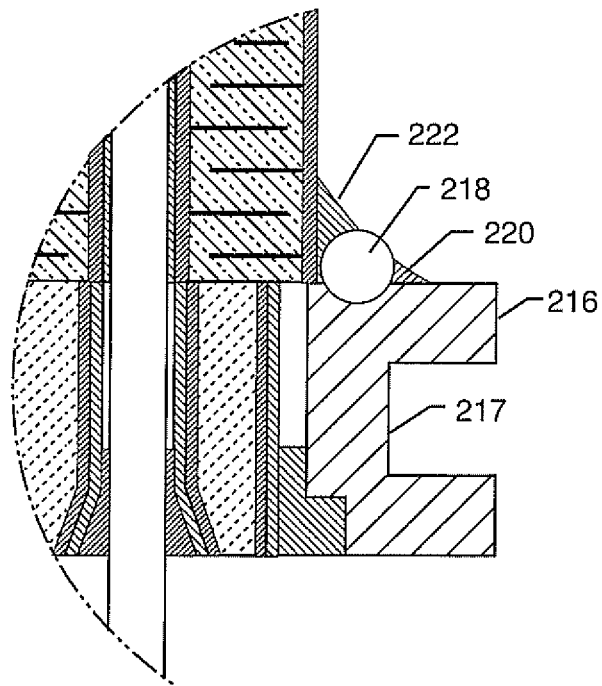
FIG. 28A is an enlarged view of a novel embodiment of a similar structure to FIG. 28 taken along lines 28A-28A.

FIG. 28A is an enlarged view of a new embodiment of the structure from FIG. 28 taken from lines 28A-28A now showing the wire 218 recessed into the ferrule 216. In this way the wire 218 may be positioned and affixed in a more efficient manner.

Figure 28B:
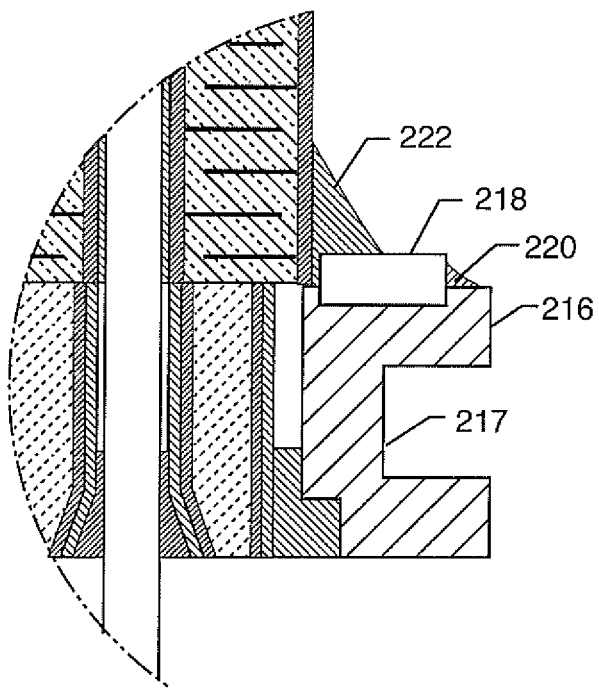
FIG. 28B is another embodiment similar to the structure of FIG. 28A now showing a rectangular shaped structure attached to the ferrule.

FIG. 28B is an enlarged view of another embodiment of the structure from FIG. 28 taken from lines 28B-28B now showing the rectangular wire 218 recessed into the ferrule 216. In this way the rectangular wire 218 may be positioned and affixed in a more efficient manner.

The round wire illustrated in FIG. 28A and the rectangular wire illustrated in FIG. 28B are just two embodiments. An infinite number of drawn wire shapes are available to the designer in the present application. This can include a square wire, a triangular wire, an elliptical wire or any cross-sectional shape that one can imagine. Accordingly, the present invention is not limited to any particular geometry wire and is in fact, inclusive of all possible geometries. As will be further illustrated, the oxide-resistant wire addition or metal additions of the present invention may also be comprised of cladded wire. An example of a cladded wire would be one with platinum cladding over an inexpensive copper core. The purpose of cladding is to provide an oxide resistant surface, but also reduce the cost by minimizing the use of precious metals.

Figure 27A:
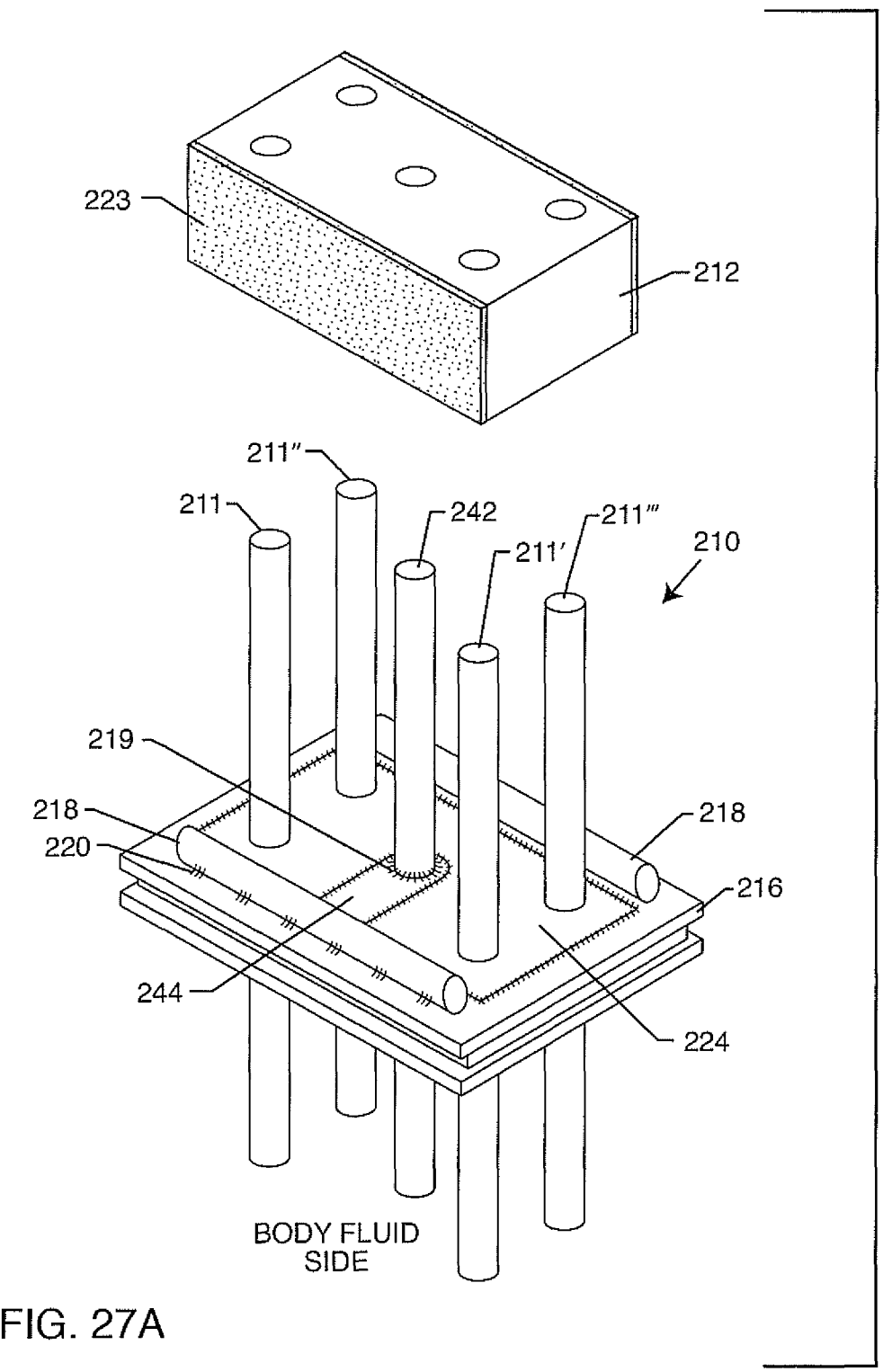
FIG. 27A is an exploded view of the structure of FIG. 27 showing the peninsula portion of the ferrule.
Figure 28C:
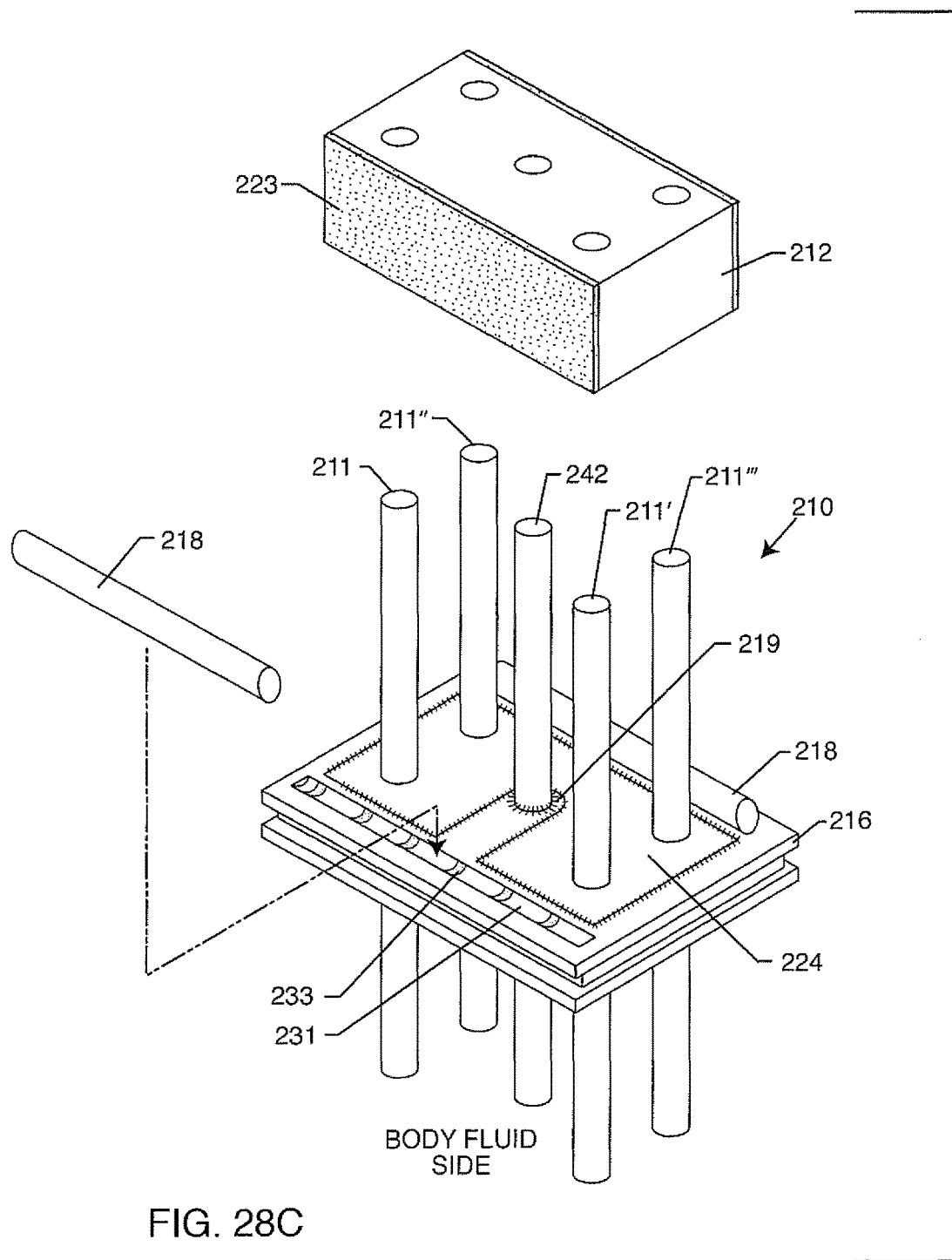
FIG. 28C is a view similar to 27A except now showing a recess on the ferrule for the wire to fit within.

FIG. 28C shows a perspective view similar to FIG. 27A now with the recess 231 and inserts 233 clearly shown. The inserts 233 are placed in the recess 231 before the wire 218 is placed and may be gold metal, gold brazed or any of the material variations and connection methods already described herein.

FIG. 29 is similar to FIG. 25 and illustrates that the two wires 218 could be replaced by a number of pads 234 as shown. In general, the pads could be formed as a continuous part (not shown) of the machining of the ferrule 216 or they could be added as a subsequent assembly by gold brazing or laser welding 220 as shown. The pads 234 would be of the same noble materials previously described as for the wire 218. This means that a convenient oxide resistant electrical connection 222 could be made using solder or thermal-setting conductive adhesives.

Throughout the invention, the intermediate biostable and oxide resistant intermediate structure, such as lead 218 shown in FIG. 27 with pad 234 as illustrated in FIG. 29, must have the following properties: 1) they must be weldable or brazable to the titanium ferrule 216; 2) this weld or braze joint 220 must break through any oxides of titanium and form a metallurgical bond between the structure 218 or 234 and the ferrule 216; and 3) the intermediate biostable wire 218 or pad 234 must be connectable to the capacitor's external metallization 223. The number of connection methods to the capacitor's external metallization is limited. This includes solders, solder paste and all types of thermal-setting conductive adhesives. In general, although possible, it is not reliably possible to braze or weld directly to the capacitor's external metallization 223, hence this option is not a preferred embodiment. In summary, the biostable wire 218 or pad 234 need not be platinum, but it can consist of a long list of metals, alloys based on these metals and combinations thereof that would meet the above criteria. Choices would be gold, palladium, tantalum, and niobium, alloys based on these metals and combinations thereof. Additional non-limiting considerations include: tungsten, iridium, ruthenium, rhodium, silver, osmium, alloys based on these metals and combinations thereof. Other nonlimiting examples include platinum based materials such as platinum-rhodium, platinum-iridium, platinum-palladium, platinum-tungsten, platinum-ruthenium, platinum-gold, gold-palladium, gold-silver, silver-palladium, gold-platinum and naturally occurring alloys like platiniridium (platinum-iridium), iridiosmium and osmiridium (iridium-osmium).

It will be appreciated that the pad 234 could also be clad as previously described, to the various wires 218 of FIG. 25 and on.

FIG. 30 is a sectional view taken from section 30-30 from FIG. 29 illustrating that the pads 234 and 234' are disposed on both sides of the capacitor. It will be understood to those skilled in the art that they could also be disposed at the ends of the capacitor (not shown). It will be appreciated to one skilled in the art that the pads could be connected. For example, referring once again to FIG. 27, pads 234 and 234a could be filled in between so that there was one large continuous pad. These pads could also have holes in them to further facilitate the electrical attachment between the pad and the capacitor external ground metallization 223.

FIG. 31 is a perspective view of another embodiment similar to FIGS. 25-30 now showing a different configuration of pad 234. Here, pad 234 is shown in an L-shape. There is a hole in the bottom of the pad facilitating the laser weld or braze 220 to the ferrule 216. FIG. 32 is a sectional view taken along line 32-32 from the structure of FIG. 31.

Figure 33:
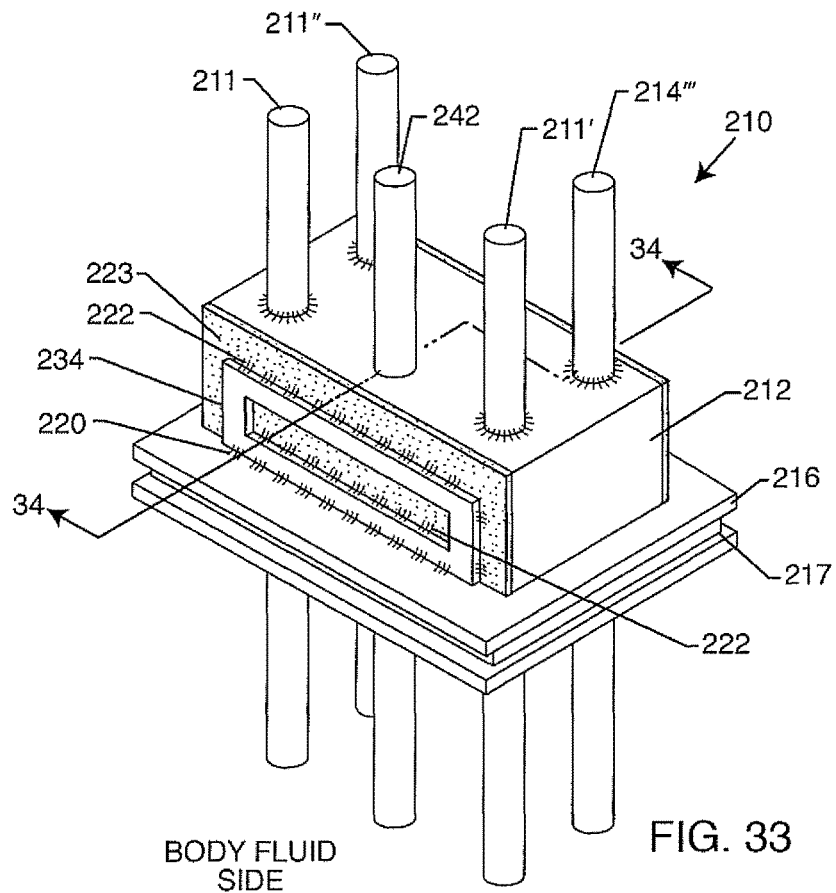
FIG. 33 is a perspective view of another exemplary feedthrough capacitor embodying the present invention.

FIG. 33 is a perspective view of yet another embodiment of a feedthrough capacitor assembly 210 similar to FIGS. 25-32. Here the pad 234 is a long pad that spans the length of the long side of the capacitor 212. The pad 234 has a large hole to facilitate the placement and bonding of the conductive adhesive 222.

Figure 34:
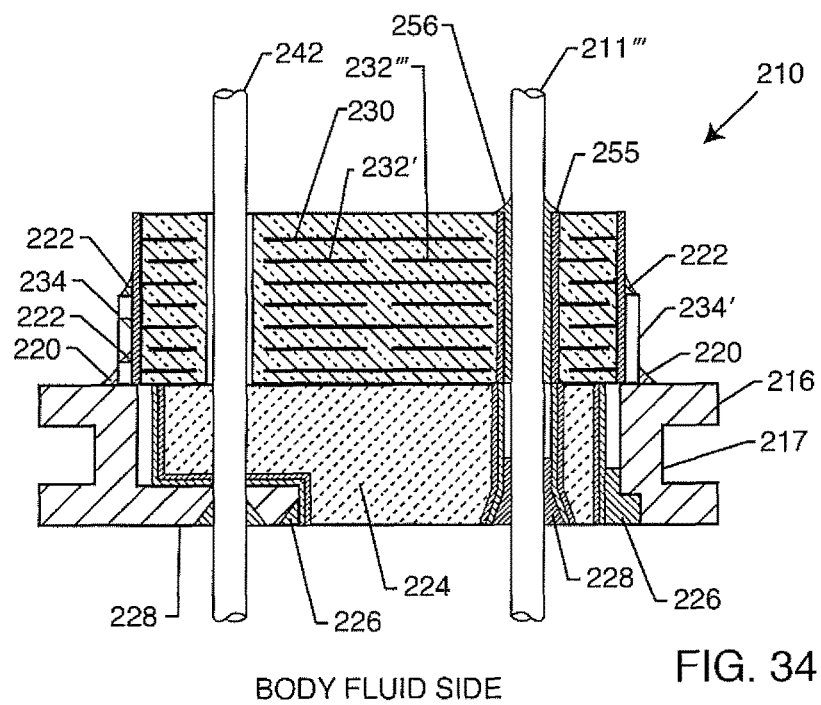
FIG. 34 is a sectional view taken along the non-linear line 34-34 of the structure of FIG. 33.

FIG. 34 is a sectional view taken from section 34-34 from FIG. 33. It shows the long bracket 234 cross-section along with laser weld or braze 220.

Figure 35:
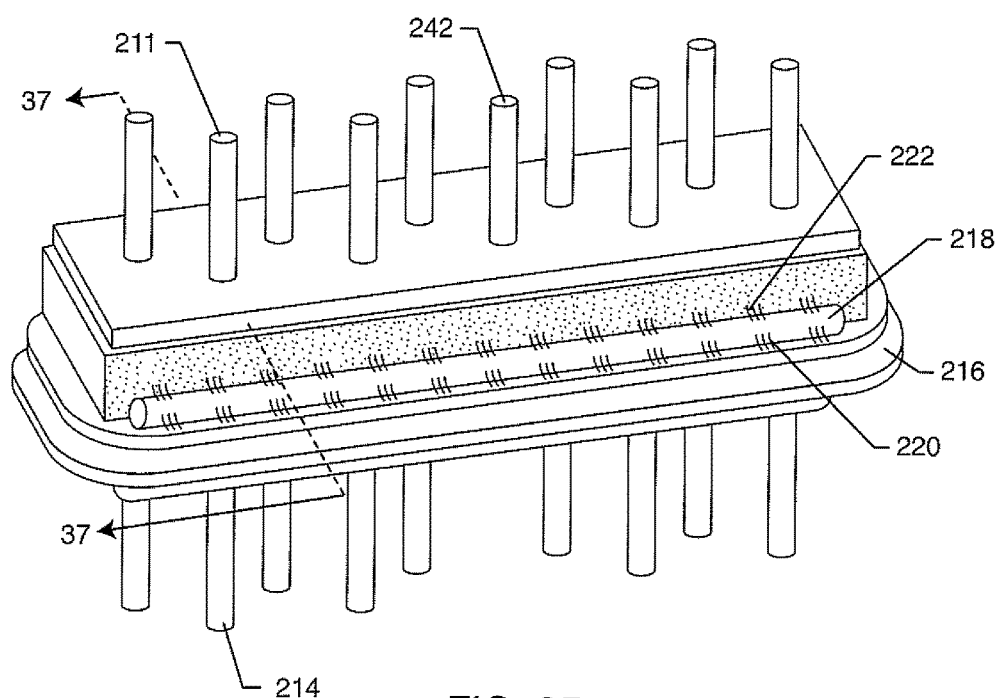
FIG. 35 is a perspective view of another exemplary feedthrough capacitor embodying the present invention.
Figure 36:
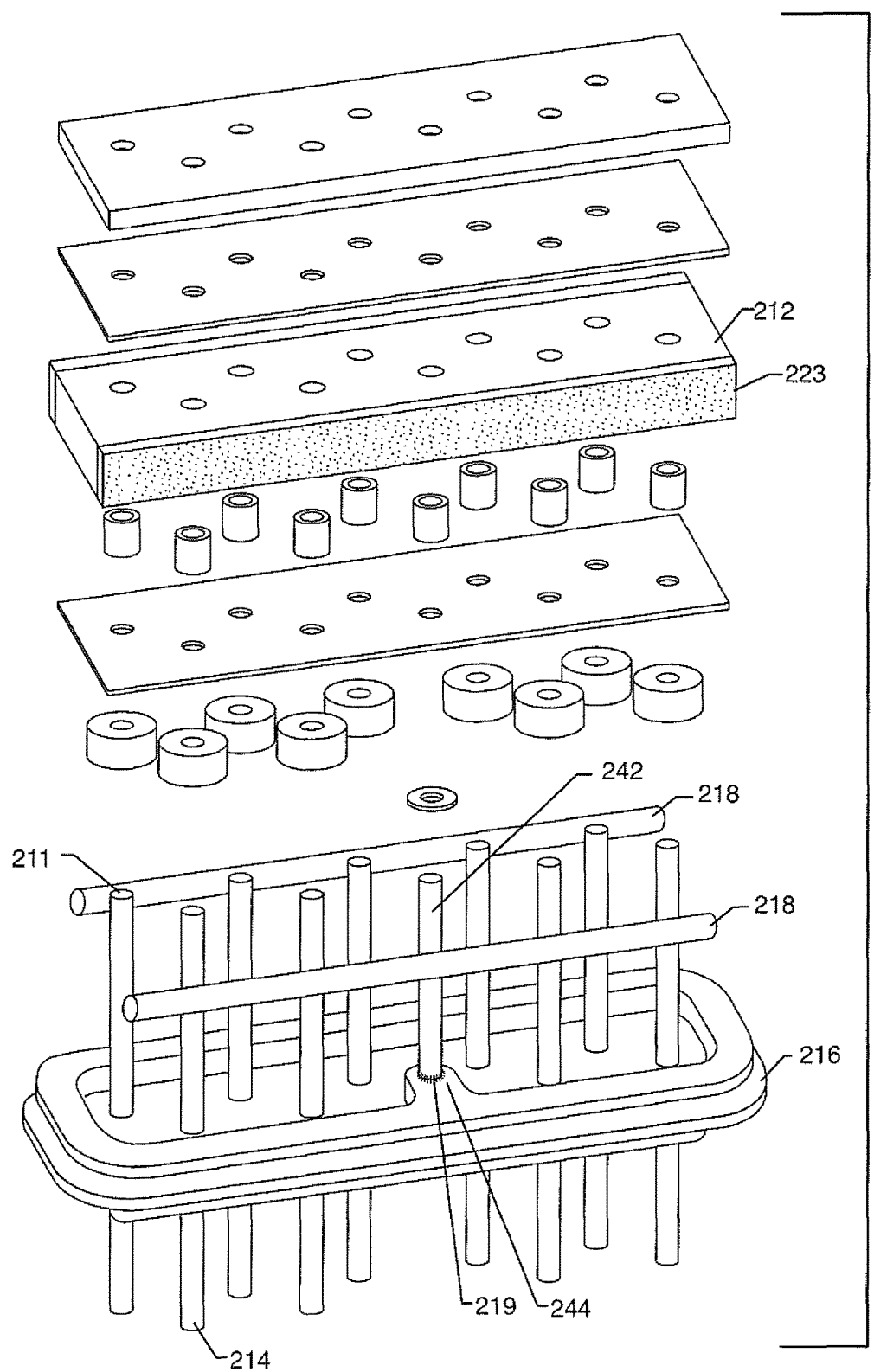
FIG. 36 is an exploded view of the structure of FIG. 35 showing the peninsula portion of the ferrule.

FIG. 35 is similar to FIG. 25 except in this case there are more terminal pins 211. Accordingly, it is necessary that the oxide-resistant biostable wire 218 be longer and have more laser welds 220. This is because it would be undesirable to have a long distance between a filtered terminal pin and its associated ground. This is because inductance and resistance can build up across an internal ground plane, thereby degrading the RF filtered performance of a distal filtered pin. FIG. 36 is an exploded view of the structure of FIG. 35. In FIG. 36, the ground pin 242 is shown laser welded 219 or gold brazed 219 into the ferrule 216 in the peninsula area 244. In this case, the capacitor is a conventional capacitor wherein the ground electrode plates are terminated with metallization 223 disposed along the two long outside ends of the capacitor 212. In this case, there is no connection between terminal pin 242 and the capacitor's ground electrode plate stack 230. In a different embodiment (not shown), a capacitor's ground electrode plates could be connected to this grounded pin as completely described in U.S. Pat. No. 5,905,627, the contents of which are incorporated herein by reference. Referring once again to FIGS. 35-37, an alternative is given wherein a direct connection to terminal pin 242 and the grounding of the capacitor's electrode stacks 230 is nonexistent. That is, the electrical connection is between the capacitor metallization 223 and the noble wires 218.

Figure 37:
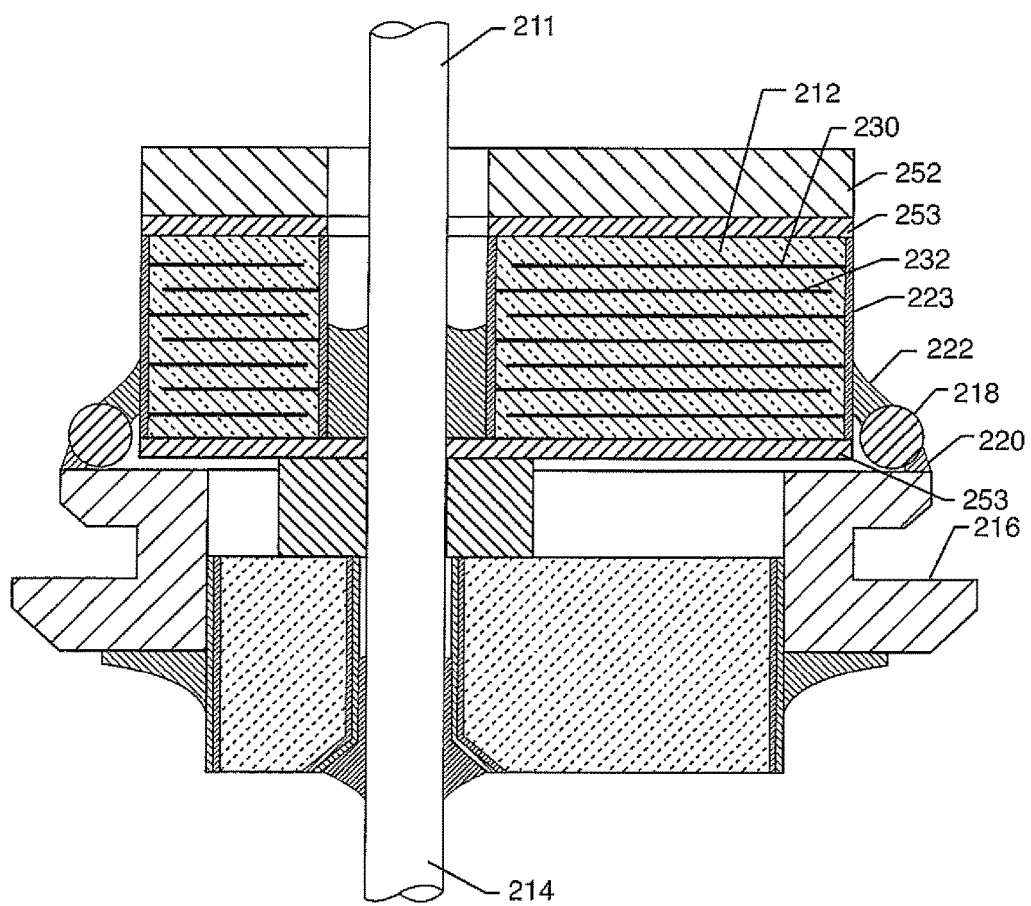
FIG. 37 is a sectional view taken along line 37-37 of the structure of FIG. 35.

FIG. 37 is a sectional view taken from section 37-37 from FIG. 35 illustrating that any one of the active pins 211 passes through feedthrough holes near the center of the capacitor 212 in a staggered pattern where the pin 211 makes contact with its own individual set of active electrode plates or many active electrode plates 232. The ground electrode plates 230 contact the capacitor's long-side perimeter metallization 223. The electrical attachment material 222 attaches the capacitor ground metallization 223 to the noble wire 218. The electrical attachment material 222 can be a solder or a thermal-setting conductive adhesive. The wire 218 can then be brazed or welded 220 to the ferrule 216.

Figure 38:
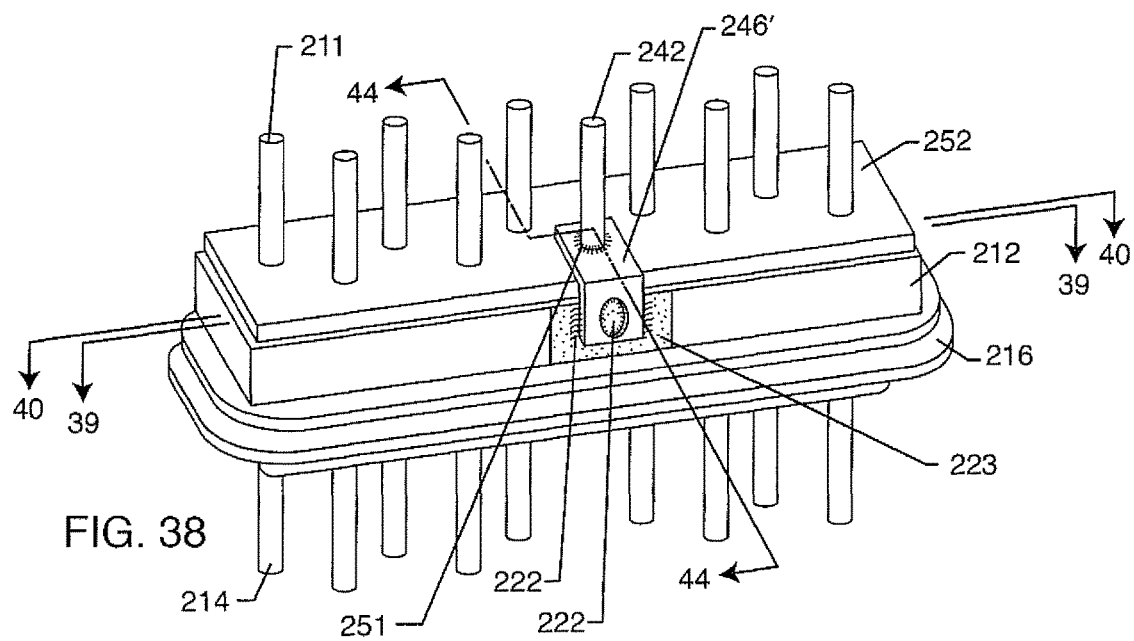
FIG. 38 is a perspective view of another exemplary feedthrough capacitor embodying the present invention.

FIG. 38 is similar to FIG. 35, which illustrates an alternative method of grounding the capacitor's ground electrode stack 230. Referring back to FIG. 36, one can see the novel ferrule peninsula 244 to which ground pin 242 is electrically and mechanically attached. In FIG. 28, ground pin 242 is electrically attached to the ferrule 216 and is thereby grounded in a similar manner as shown in FIG. 36. A novel L-shaped clip 246' is electrically attached to ground pin 242 and engages a portion of the capacitor's external ground metallization 223. This is best illustrated in FIG. 28, where the ground clip 246' being electrically connected 222 to the capacitor's ground metallization 223 is shown. Then, the ground pin 242 is electrically connected at 251 to the ground clip 246'.

Referring back to FIG. 38, illustrated is clip 246' disposed on the top surface of the capacitor 212. There is an insulating structure 252 that is disposed on top of capacitor 212. This can be a conformal coating of insulation, an insulation sheet with adhesive layer, or even an alumina ceramic thin sheet of insulation. For the case where this insulation sheet 252 is alumina ceramic, it may have a cut-out pocket so that the clip 246' drops down into it and fits flush with the top of the insulating layer 252. This would help to hold the clip 246' in place and to index it.

Figure 39:
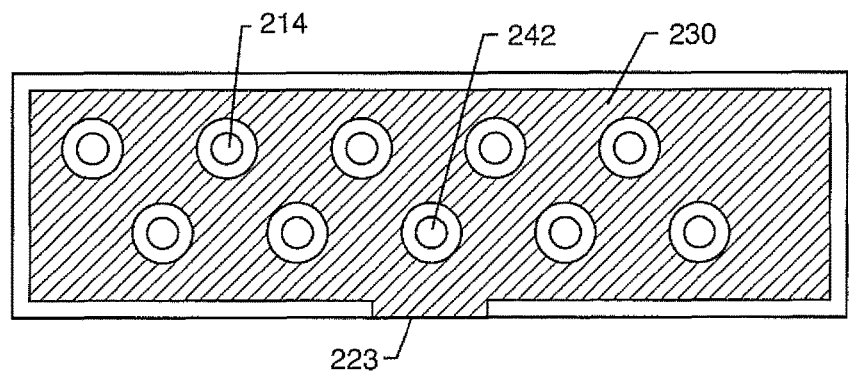
FIG. 39 is a sectional view taken along line 39-39 of the structure of FIG. 38 now showing a ground electrode plate.

FIG. 39 shows the ground electrode plate 230 which does not make contact with the leadwires 211 or the grounded wire 242. The ground electrode plate 230 makes contact with metallization 223 which is then in electrical contact with novel pad 246'.

Figure 40:
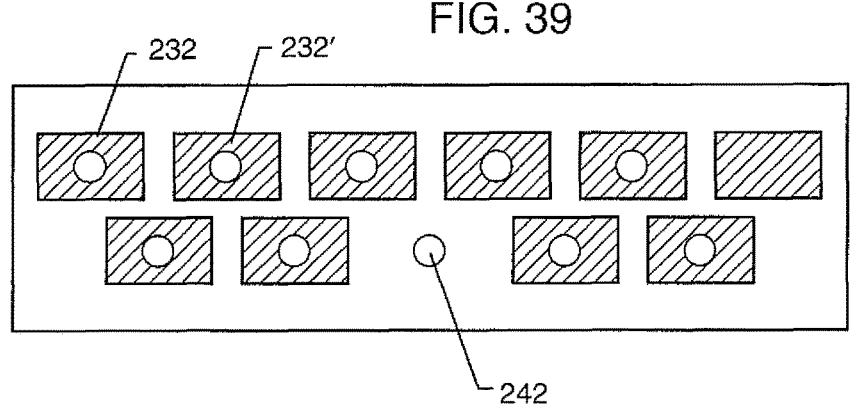
FIG. 40 is an sectional view taken along line 40-40 of the structure of FIG. 38 now showing an active electrode plate.

FIG. 40 shows a multitude of active electrode plates 232 electrically coupled to the leadwires 211. Note that the grounded pin 242 lacks an active electrode plate 232.

Figure 41:
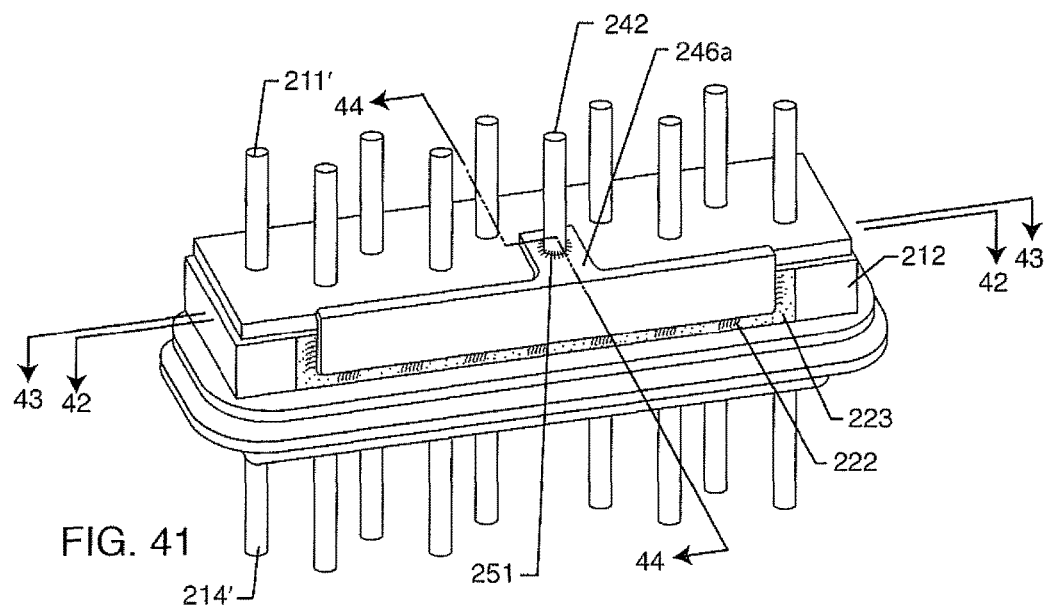
FIG. 41 is a perspective view of another exemplary feedthrough capacitor embodying the present invention.
Figure 42:
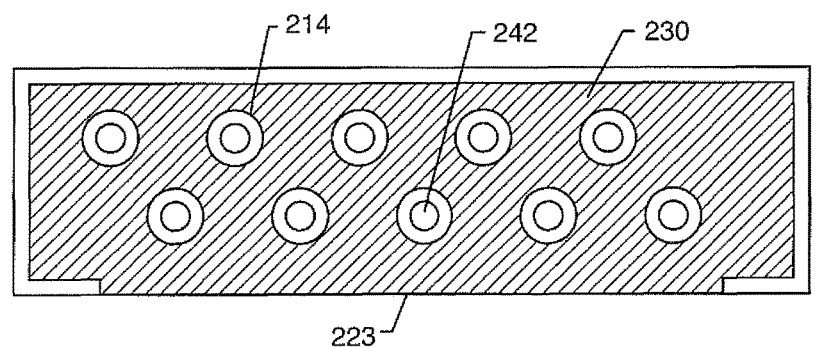
FIG. 42 is an sectional view taken along line 42-42 of the structure of FIG. 41 now showing a ground electrode plate.
Figure 43:
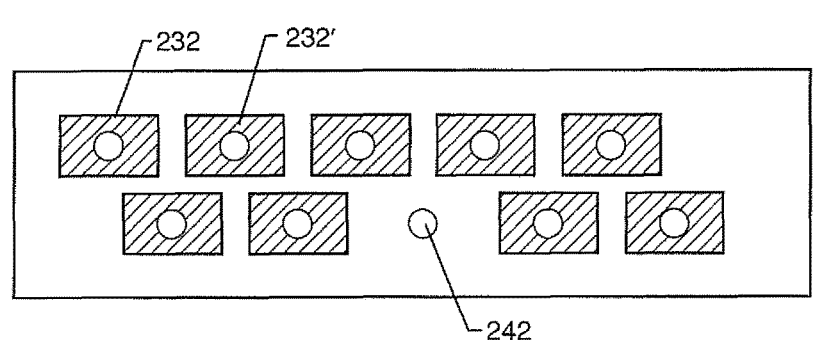
FIG. 43 is an sectional view taken along line 43-43 of the structure of FIG. 41 now showing an active electrode plate.

FIGS. 41-43 are very similar to FIGS. 38-40. FIGS. 41-43 show a different embodiment of the novel pad 246a. Pad 246a is longer along the length of increased metallization 223. This design would increase filter performance due to the shortened electrical pathways. In this way, the inductance across the ground planes of the capacitor is greatly reduced. This means that outer pins 211 will have improved attenuation and greater insertion loss than the structure previously illustrated in FIG. 38.

Figure 44:
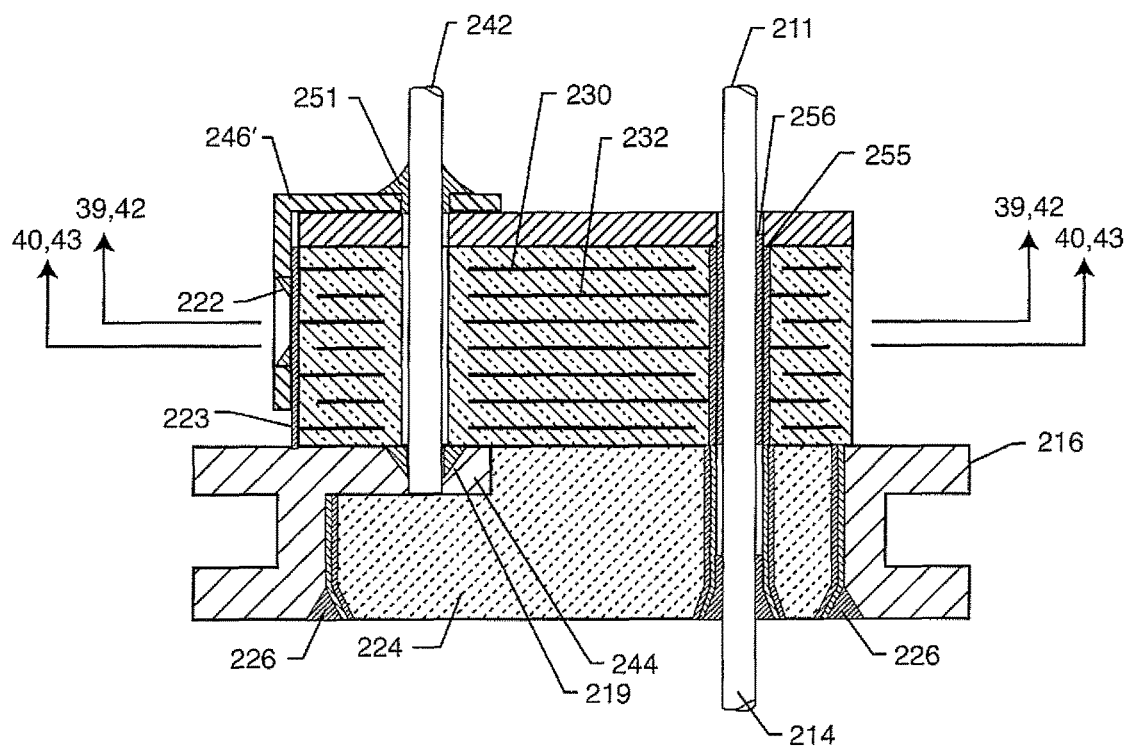
FIG. 44 is a sectional view taken along the non-linear lines 44-44 of the structures of both FIGS. 38 and 41.

FIG. 44 is a sectional view for both FIGS. 38 and 41. One can see better the peninsula or extension 244 that attaches to the ground wire 242. Referring once again to FIG. 44, one can see that the peninsula structure 244 can alternatively be placed on the right side as opposed to the left side. In addition, peninsula 244 could be placed on both sides, which would mean that there would be two ground pins 242. In this way, metallization 223 could also be added to the right side of the capacitor so that the right side became a mirror image of the core structure 246' and grounded lead 242. An advantage of having two grounded pins 242 would be even lower inductance and resistance in the grounding path from the capacitor ground electrodes 230 through to the ferrule 216.

Figure 45A:
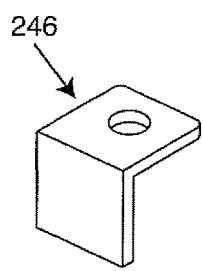
FIGS. 45A, 45B and 45C are perspective views of various embodiments of the novel ground attachments shown in FIGS. 38, 41 and 44.
Figure 45B:
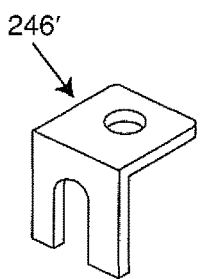
Figure 45C:
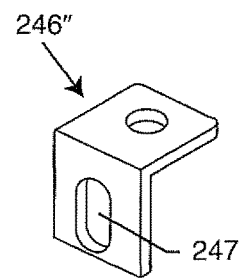

FIGS. 45A, 45B and 45C illustrate various types of L-shaped clips 246. In FIG. 45C, one can see the advantage of having a clip with an elliptical hole 247 because this allows electrical connection material 222, which can be a solder or a thermal-setting conductive adhesive, to be placed on the outside of the clip and also inside the elliptical hole. This increases the electrical contact area and thereby reduces the resistance as well as improves mechanical strength.

Figure 46:
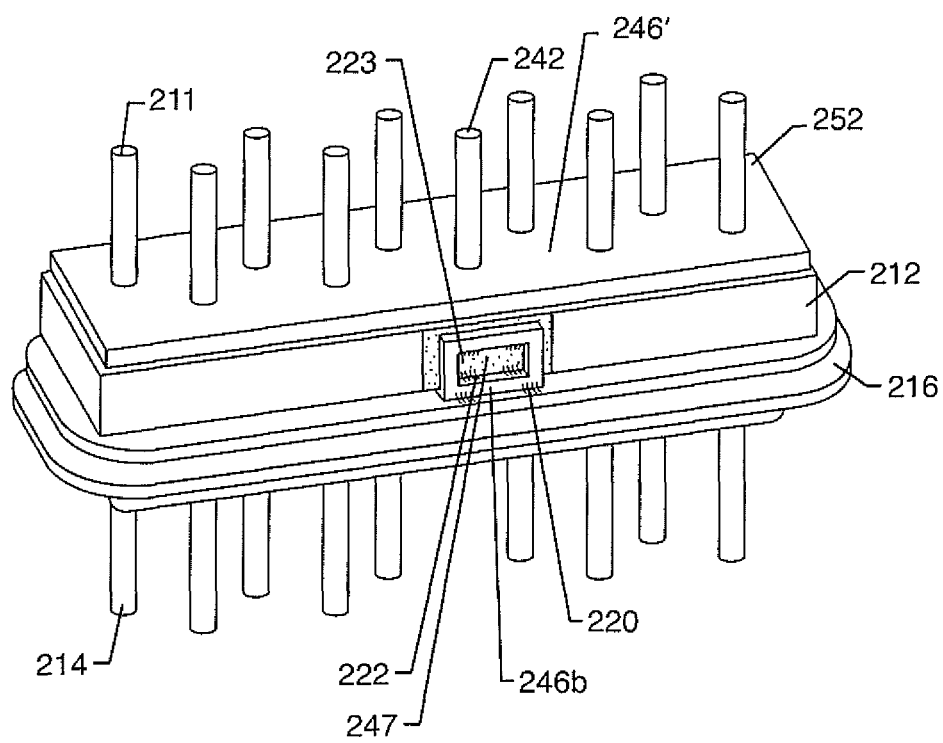
FIG. 46 is a perspective view of another exemplary feedthrough capacitor embodying the present invention.
Figure 47:
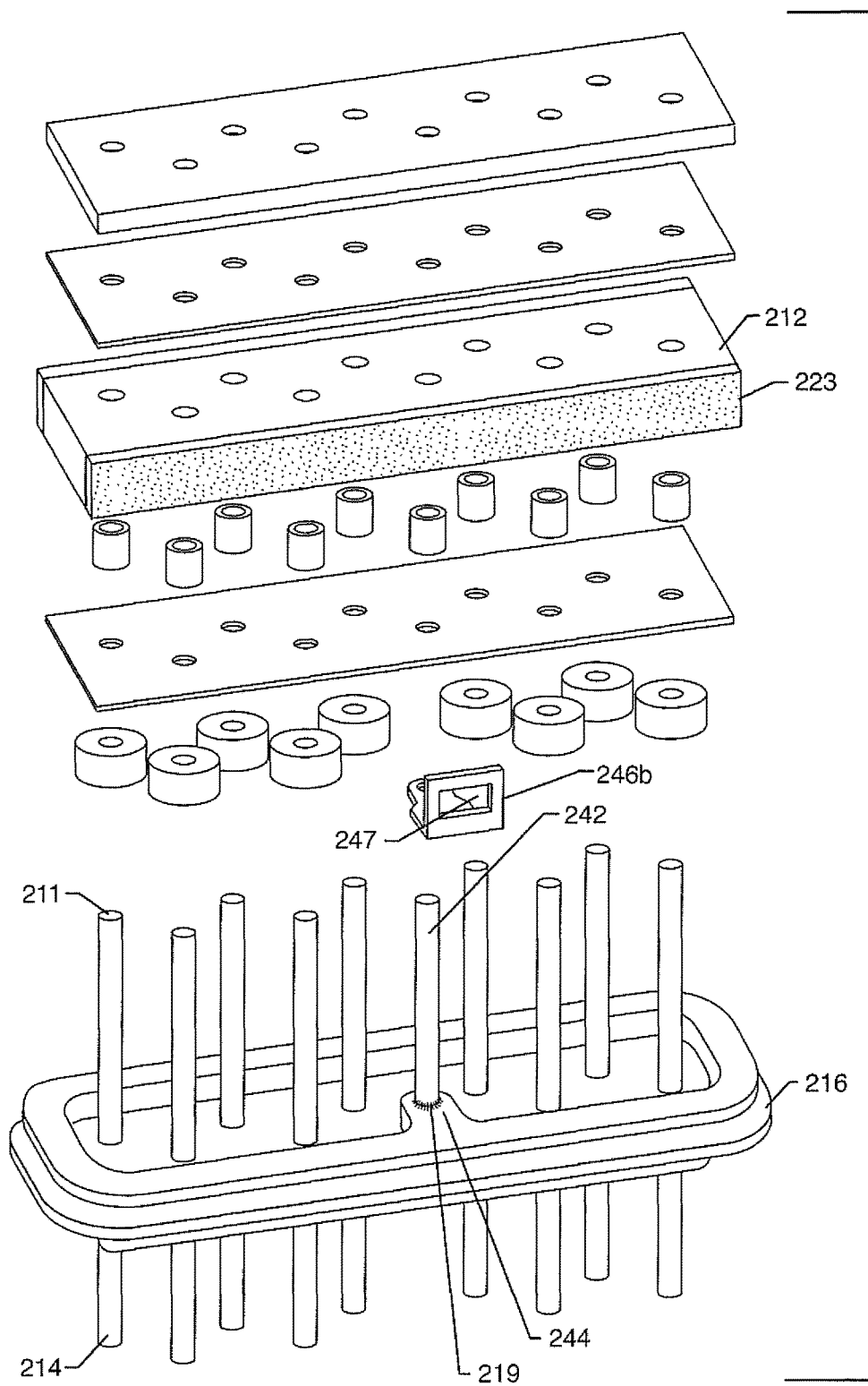
FIG. 47 is an exploded view of the structure of FIG. 46 showing the novel ground attachment below the capacitor.

FIGS. 46 and 47 are an alternative embodiment of clip 246b previously illustrated in FIGS. 38 and 41. The novel clip 246b is under the capacitor 212 sandwiched between the ferrule 216 and the capacitor 212. A hole 247 is also in the clip 246b to facilitate placement of conductive adhesive 222. FIG. 47 is an exploded view that best shows the shape of novel clip 246b.

In the alternative embodiment shown in FIG. 46, the clip 246b is disposed underneath the capacitor 212 and electrically and mechanically attached directly to the peninsula structure 244. Having the clip 246b disposed underneath the capacitor 212, and then coming up on the side as is illustrated, would improve the RF performance of the capacitor. Effectively, this would shorten the ground pin 242 to almost zero thereby reducing the impedance and inductance of the ground clip 246b. A notch (not shown) could be put in the ferrule 216 of the hermetic terminal to facilitate the clip coming out through the bottom so that the capacitor 212 still would sit flush on top of the ferrule structure 216.

Figure 51:
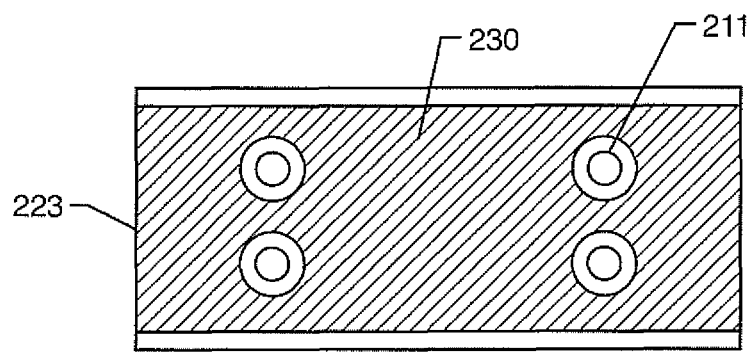
FIG. 51 is a sectional view taken along line 51-51 of the structure of FIG. 50 now showing a ground electrode plate.
Figure 52:
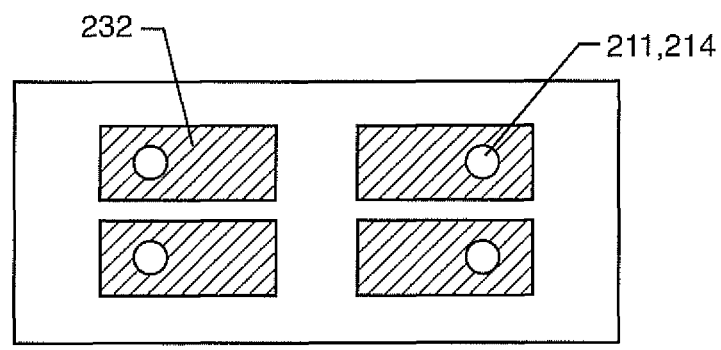
FIG. 52 is a sectional view taken along line 52-52 of the structure of FIG. 50 now showing an active electrode plate.
Figure 53:
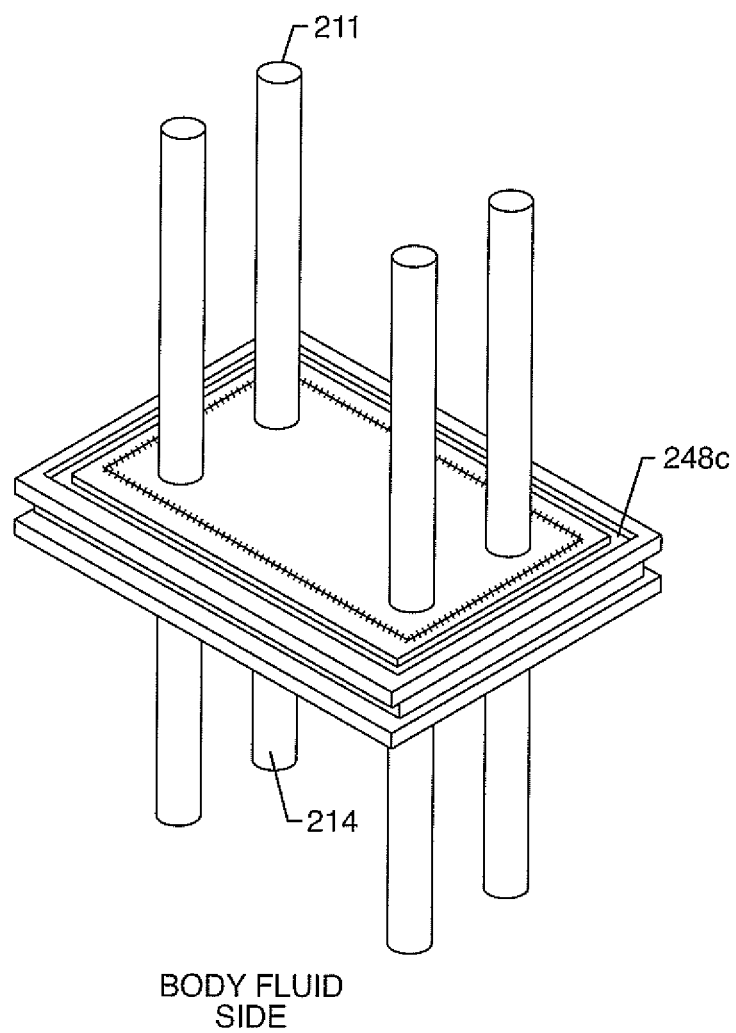
FIG. 53 is a perspective view of another exemplary feedthrough embodying the present invention now showing novel ground attachments around the continuous perimeter of the ferrule.

FIGS. 48-53 are similar to FIGS. 25-34 except that in this case pockets 248 and noble metal inserts 250 have been formed so that an oxide resistant electrical attachment 222 can be made between the capacitor ground metallization 223 and the ferrule 216. An alternative embodiment 250' is shown where first, a brazing perform, such as a gold braze perform 250a, is placed and then a platinum cap 250b is placed over it. Alternative metals may be used as noted earlier. In addition, instead of a braze 250a, one could use a resistance weld or lower temperature brazes such as those listed previously with the Cu-Sil or Ti—Cu-Sil examples. Platinum pad 250b would be slightly longer in the length direction and slightly longer in the width direction than the underlying pre-form 250a. This overlaying would prevent it from reflowing and leaking out during a gold braze operation. In addition, the pad 250b would protrude above the surface of the ferrule. This turns out to be very convenient during electrical attachment of the feedthrough capacitor (not shown) outside perimeter metallization 223. In other words, the protruding pad 250b would provide a convenient stop for a solder paste, a solder pre-form or a thermal-setting conductive adhesive (dispensed by robot). This is best understood by referring to FIGS. 48 and 49, which shows that a pocket 248 and 248a are first formed at the time of manufacturing the ferrule 216 of the hermetic seal subassembly 210. These pockets can be rectangular (as shown), can be rectangular with rounded ends or it can be round holes as illustrated as 248a or even a continuous groove or slot as illustrated in FIG. 53 as 248c. Into these pockets or grooves 248 can be placed a noble wire 218 as previously described in FIG. 25, or a material 250, such as CuSil or TiCuSil or any other material as disclosed earlier that can form a metallurgically sound bond to titanium while at the same time, providing an oxide resistant surface to which electrical attachment 222 can form a solid bond.

Referring once again to FIG. 49, one can see that there is an alternative arrangement similar to that previously described in FIG. 48. In this case, a circular gold braze pre-form 250Ab could first be placed into the counter-bore hole 248a and then a platinum or equivalent cap 250Aa could be placed over it. These could all be reflowed into place leaving a convenient area to make electrical attachment between the capacitor external ground metallization 223, through the oxide resistant pad 250Aa, through the braze material 250Ab and, in turn, to the ferrule 216.

Figure 50:
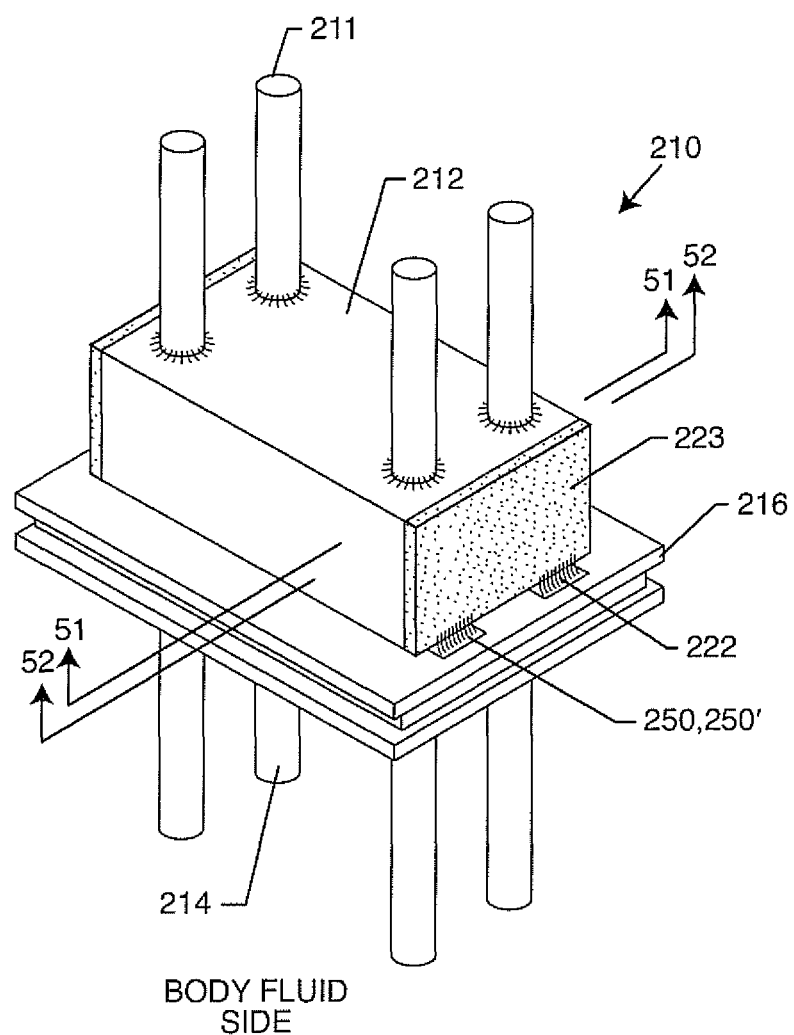
FIG. 50 is similar to either FIG. 48 or 49 now showing the capacitor grounded to the ferrule.

FIG. 50 is an isometric view of the quad polar feedthrough capacitor 212 shown mounted to the hermetically sealed ferrule assembly previously illustrated in FIG. 48. Shown is an electrical attachment material 222 between the capacitor ground metallization 223 that connects to the oxide resistant connection pads 250, 250'. Referring once again to FIG. 50, one can see that there is metallization 223 on both short ends of the capacitor 212. This metallization 223 could extend along the long sides or, alternatively, along all perimeter sides of the capacitor. In the case where the length of the perimeter metallization 223 is made longer, then additional pockets and oxide resistant pads 250 would be required.

FIGS. 51 and 52 illustrate the ground and active electrode plate sets of the capacitor 212 previously illustrated in FIG. 50. In FIG. 51, shown is that the ground electrode plate 230 does not make contact with any of the terminal pins 211. The metallization 223 contacts the ground electrode plate set 230 on its left and right ends. FIG. 52 illustrates the active electrode plates 232. In this case, the active electrode plates 232 are connected to each one of the feedthrough terminal pins 211.

FIG. 53 is the same ferrule as previously described in FIGS. 49 and 50 except that instead of a discrete number of machined pads 248, there is a continuous groove 248c formed around the entire perimeter of the capacitor. This would be filled with Cu-Sil or Ti—Cu-Sil or any other material previously listed to form an oxide resistant connection area for the feedthrough capacitor (not shown). A feedthrough capacitor 212, in this case, would have perimeter metallization 223 along all four of its perimeter sides and either a continuous or a multiplicity of short electrical connections 222 would be made between the capacitor metallization 223 and the gold braze or equivalent material that has been flowed in the trough 248c (not shown).

Figure 54:
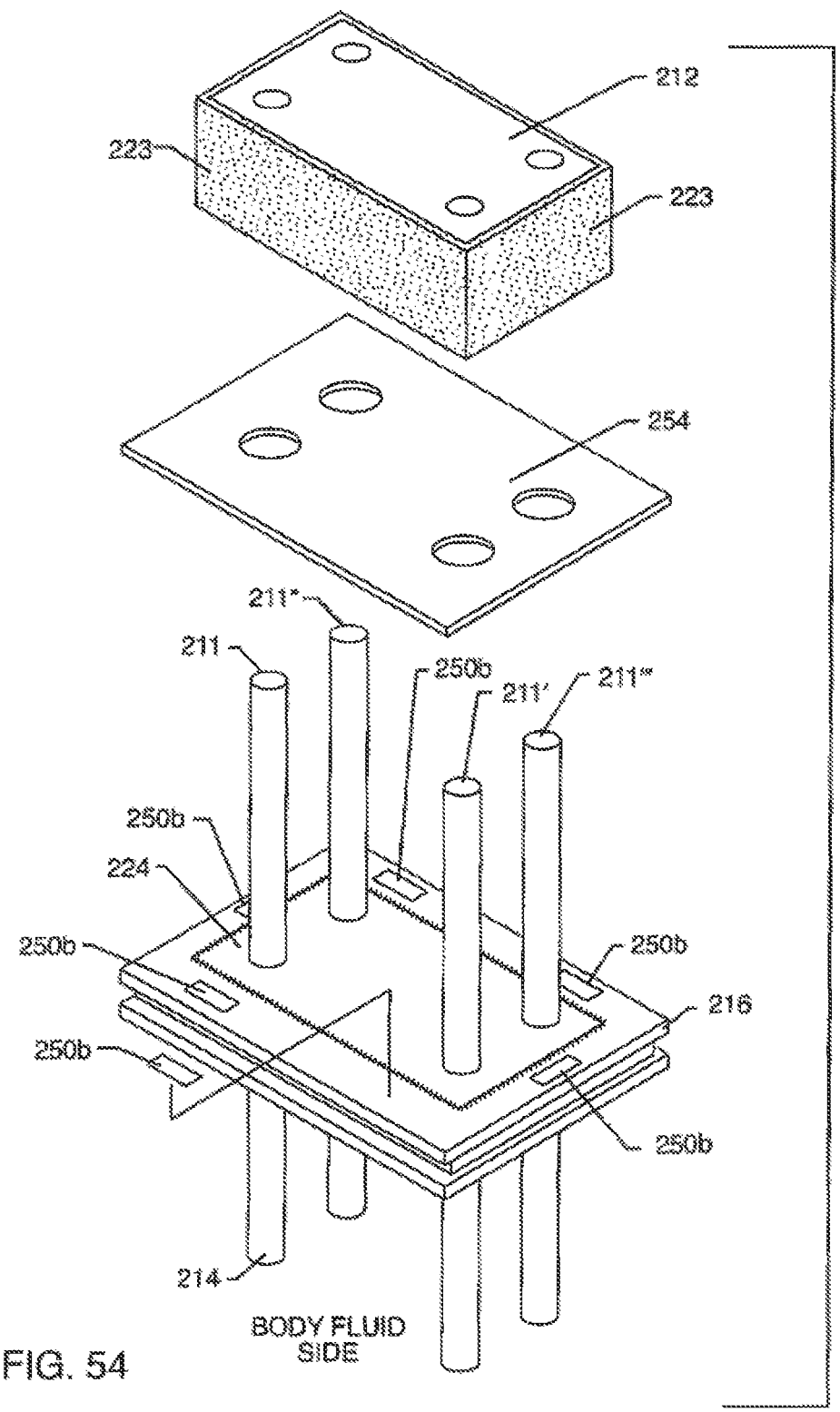
FIG. 54 is an exploded view of another exemplary feedthrough capacitor embodying the present invention now showing novel ground attachment plate.
Figure 55:
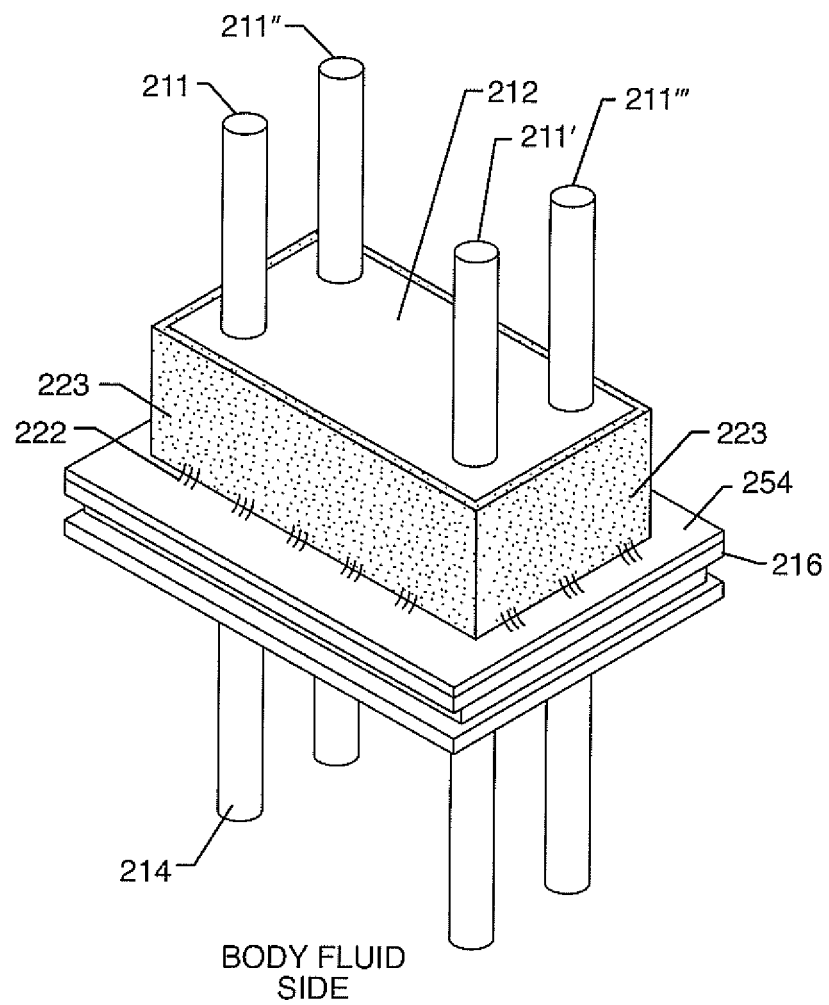
FIG. 55 is the perspective assembled view of the structure of FIG. 54 showing the capacitor metallization grounded to the novel plate.

FIGS. 54 and 55 are yet another embodiment of the present invention. As shown in FIG. 54, gold films 250b may be placed on top of the ferrule 216. Then a conductive sheet 254 is laid overtop the gold films 250b. In a brazing procedure the gold films or plates bond between the conductive sheet 254 and the ferrule 216. The capacitor 212 can be placed overtop the conductive sheet 254 and then an electrical connection using conductive adhesives 222 can be made between the external metallization 223 and the conductive sheet 254. As shown in FIGS. 54 and 55, the metallization is around the entirety of the capacitor 212. This design would also reduce both the inductance and equivalent series resistance of the capacitor 212. The conductive sheet 254 is of a different material as compared to the ferrule 216 and the gold films 250b, and therefore forms an oxide-resistant metal addition.

Figure 56:
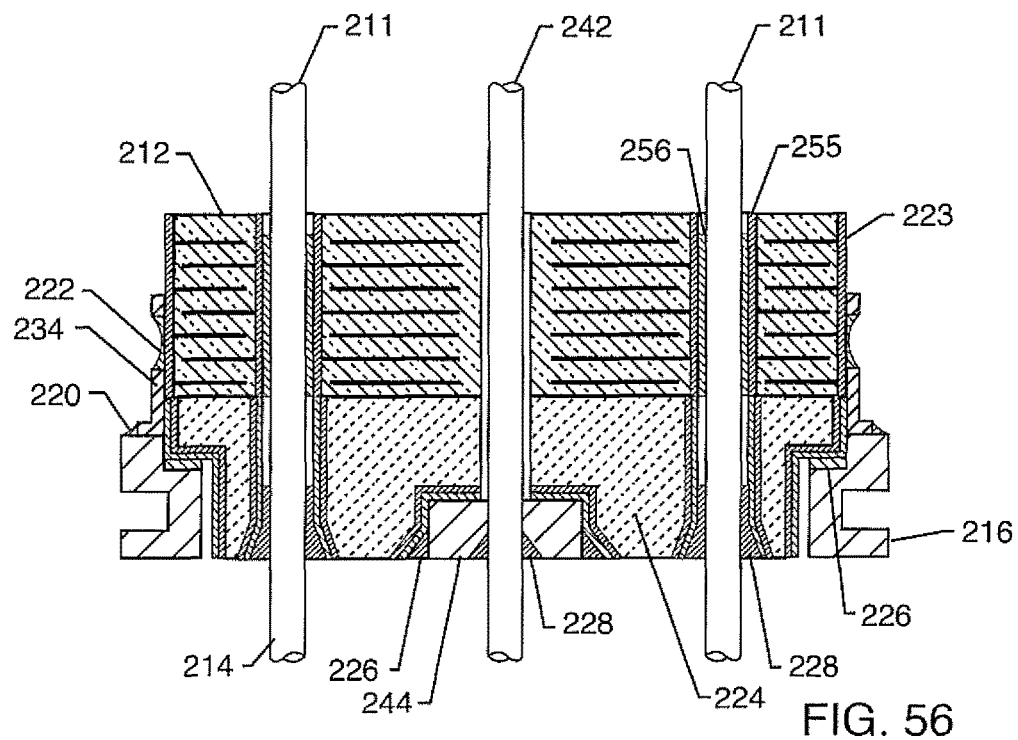
FIG. 56 is a sectional view similar to FIG. 28 showing an alternative hermetic seal between the ferrule and the insulator.

FIG. 56 is similar to FIG. 28 wherein, the gold brazes 228 for the leadwires are directed to the body fluid side. In FIG. 28, the alumina insulator 224 is hermetically sealed with gold braze 226 to the ferrule 216 which is shown with the gold braze 226 between a ferrule interwall and the outside wall of the alumina ceramic insulator 224. FIG. 56 is different in that the gold braze 226 is between the top of the ferrule or a step towards the top of the ferrule 216 and is not between a ferrule or insulator side wall. Referring once again to FIG. 56, one can see that there is a clip structure 234, which is similar to the clip structure 234 previously illustrated in FIG. 33. The clip 234 has an opening to receive a solder or thermal setting conductive adhesive 222 as shown. In general, this clip structure 234 will be an oxide-resistant metal addition in accordance with the present invention, which may be welded or brazed 220 to the ferrule 216.

Figure 57:
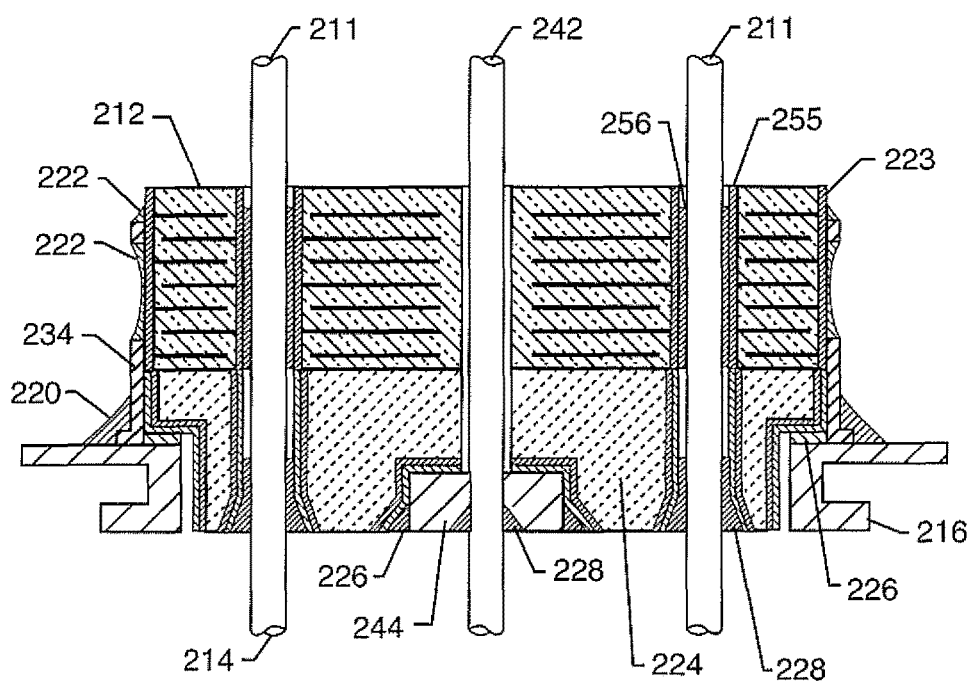
FIG. 57 is a sectional view similar to FIG. 28 showing another alternative hermetic seal between the ferrule and the insulator.

FIG. 57 is very similar to FIG. 56 except that in this case, the ferrule 216 does not has a step in it, wherein now the gold braze 226 is formed between the top face of the ferrule 216 and the bottom of the step on the alumina ceramic insulator 224.

Figure 58:
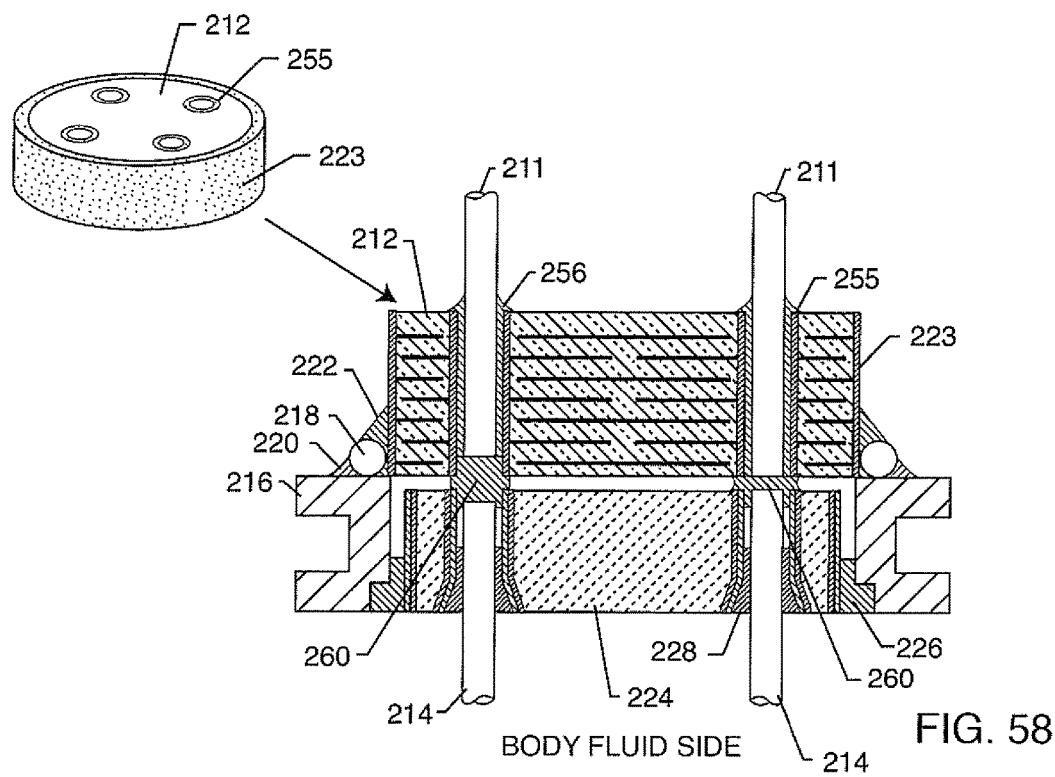
FIG. 58 is a sectional view similar to FIG. 26 showing discontinuous leadwires.

FIG. 58 is very similar to FIG. 26 except that the wires 211, 214 are discontinuous. There are actually two different subassemblies in FIG. 58. The lower subassembly is the hermetic seal subassembly, which is formed in a single process in a gold brazing furnace, thereby connecting a hermetic seal gold braze 226 between the ferrule 216 and the alumina insulator 224 and another gold braze 228 between the leadwire portions 214 and the alumina insulator 224. As part of this pre-assembly, the oxide-resistant metal addition wire 218 is gold brazed or laser welded 220 to the ferrule 216. In a separate manufacturing operation, the capacitor structure is fabricated, including its monolithic structure of alternating ground and active electrode plates, application of the outside perimeter or diameter metallization 223 and the metallization 255 on the inside of the feedthrough holes. Also pre-assembled are leadwires 211. There is a major advantage to this structure in that, the leadwires 211 can be of non-biocompatible and of toxic material since they are completely enclosed within the hermetically sealed and biocompatible AIMD housing. In other words, leadwires 211 never come into contact with bodily fluids or tissue. Therefore, leadwires 211 could be insulated copper wires or the like. In general, they are soldered or installed by a thermal-setting conductive adhesive 256 into the capacitor subassembly. The capacitor subassembly is then joined to the hermetic seal subassembly by a means of a ball grid array (solder), a thermal-setting conductive adhesive, or the like 260. The left side of the cross-section in FIG. 58 shows that the space between the leadwire segments 211 and 214 is greater, thereby requiring a higher volume of connecting material 260 as opposed to the shorter distance illustrated in the right side of the drawing. In order to minimize the resistance and optimize the current carrying capabilities, the reduced amount of conductive material 260, as shown on the right, may have less resistance and more current carrying capabilities.

Figure 59:
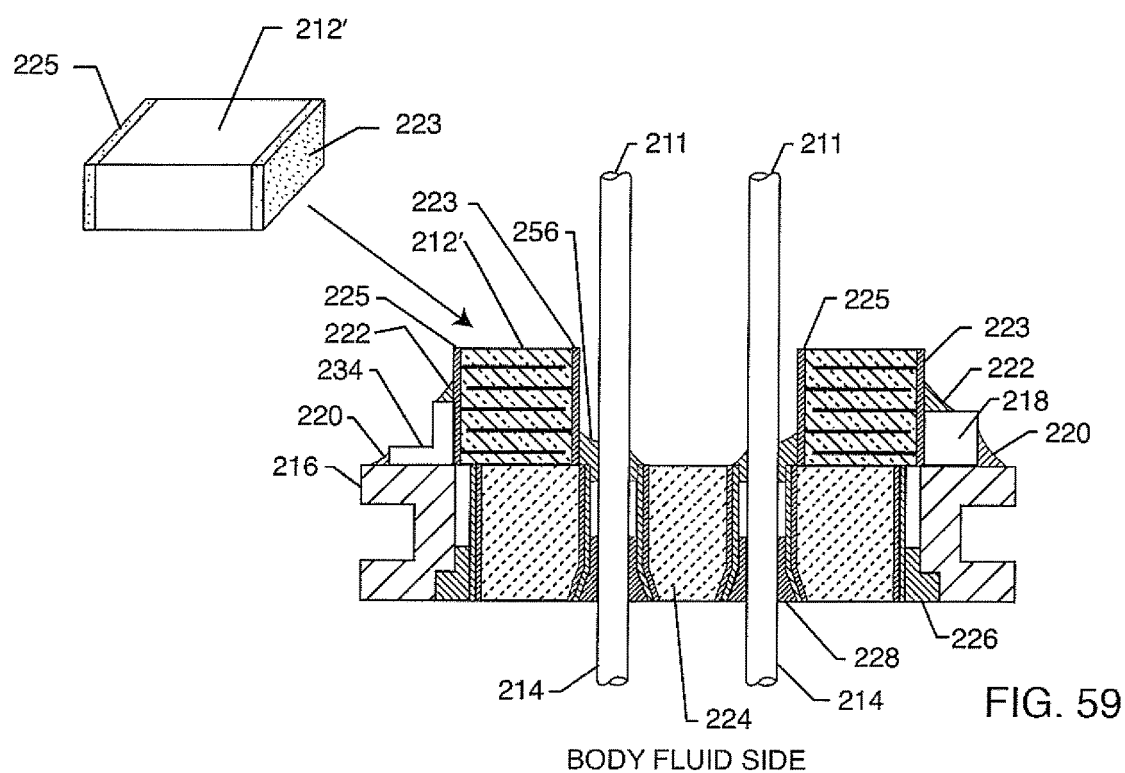
FIG. 59 is a sectional view similar to FIG. 58 now showing MLCC chip capacitors instead of feedthrough capacitors.

Referring once again to FIG. 58, capacitor 212 is a three-terminal feedthrough capacitor, also known as a planar array. FIG. 59 is similar to FIG. 58 except that instead of a multipole feedthrough capacitor, there are individual MLCC chip capacitors 212' employed. Chip caps mounted directly to a hermetic seal or to a substrate that is attached to a hermetic seal are described in U.S. Pat. Nos. 5,650,759 and 5,896,627, the contents of which are incorporated herein by reference. These two patents don't provide any way of connecting to the ferrule (ground) in an oxide-resistant manner. Referring once again to FIG. 59, one can see that the ground wire metal addition 218 of FIG. 58 has been replaced on the left side by an L-shaped wire 234 and on the right, by a square shaped wire 218. As previously stated, wires can be drawn into a multitude of cross-sections in the present invention and is not limited to any one shape. Referring to FIG. 59, chip capacitor 212' is a two-terminal MLCC.

FIG. 60 is very similar to FIG. 58 except that there are no gold brazes between the alumina insulator 224 and the corresponding leads 214. In this case, the leads 214 are co-fired with the alumina ceramic 224 to form a homogeneous structure. One can see that there are layers and conductive circuit traces 262 embedded. The purpose of this is to further improve the hermeticity of the structure. On the left hand side of FIG. 60, there is a lead 211 which is continuous and is co-fired into the alumina ceramic structure 224. On the right side, there is a short pin 211b that is co-fired into the alumina ceramic 224. This lead is then joined by electrical connection material 256 to the lead segment 211a, which extends towards AIMD internal electronic circuits. The advantage to the structure showing on the right hand side of FIG. 60 is that lead 211a can be a standard tin copper lead (or other inexpensive non-biocompatible lead material. The circuit traces or layers 262, as shown in FIG. 60, are laid down in the green state (prior to sintering) of the alumina substrate 224. In other words, the alumina substrate is initially a monolithic structure that has internal circuit traces 262 which are staggered back and forth to form a continuous conductive path through the hermetic seal insulator 224. The purpose of the staggering is to greatly improve the hermeticity and pull strength of the completed structure.

FIG. 61 is very similar to FIG. 59 except that in this case, there is a substrate or circuit board 264, which is placed adjacent the top side of the hermetic seal subassembly. On the left side, the circuit board has circuit traces 263 and 263' to which the monolithic ceramic capacitor (MLCC) 212' is electrically and physically attached. The left side of the MLCC capacitor has an electrical attachment material 222, which can be a solder, a thermal-setting conductive adhesive or the like. It attaches the left hand capacitor metallization 225 to the circuit trace 263. There is an additional electrical connection material 266. The right hand side of FIG. 61 also shows an MLCC capacitor. It is known to those skilled in the art that the rectangular MLCC could be flipped around in its orientation.

Figure 62:
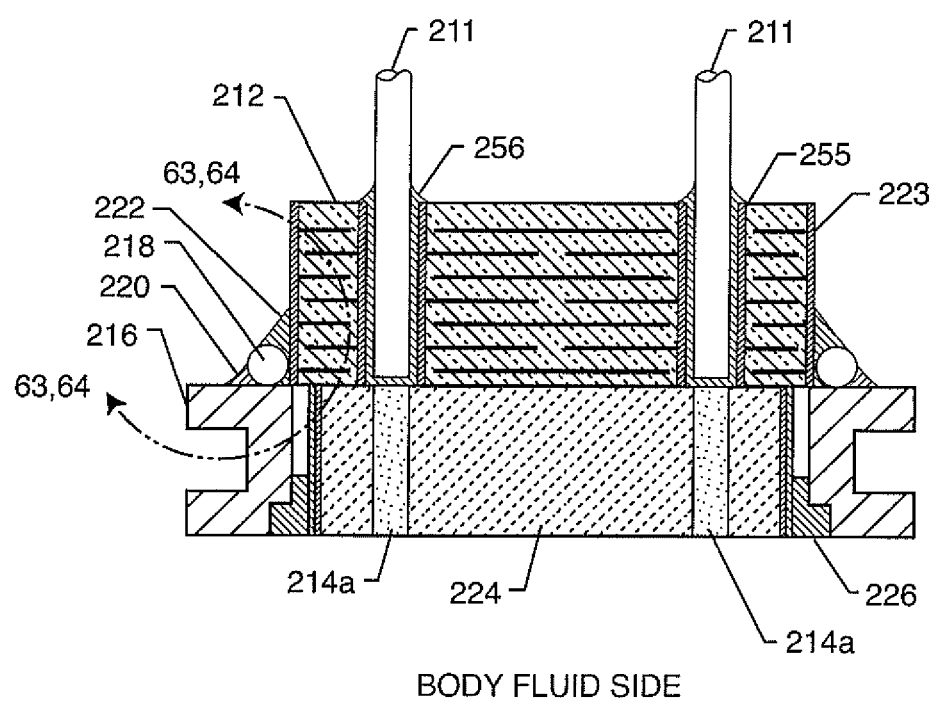
FIG. 62 is a sectional view similar to FIG. 58 now showing a co-fired alumina ceramic insulator with solid filled vias.

FIG. 62 shows a co-fired alumina ceramic insulator 224 with solid filled vias 214a, as shown. Typically these are co-fired into a single monolithic structure. For example, the structure of FIG. 62 is taught in U.S. patent publication 2014-0036409 (application Ser. No. 13/743,276), which is incorporated in full herein with this reference. The ceramic capacitor, which sits on top of the alumina ceramic insulator has leads 211, which can either be pre-installed or installed by soldering or thermal-setting conductive adhesive 256, which also makes an electrical and mechanical attachment to the solid filled vias 214a. In accordance with the present invention, the outside diameter metallization 223 of the capacitor 212 is electrically connected with a solder or a thermal-setting conductive adhesive 222 to the oxide-resistant metal addition 218. The oxide-resistant metal addition 218 can be brazed or welded 220 to the ferrule 216 in accordance with the present invention.

Figure 63:
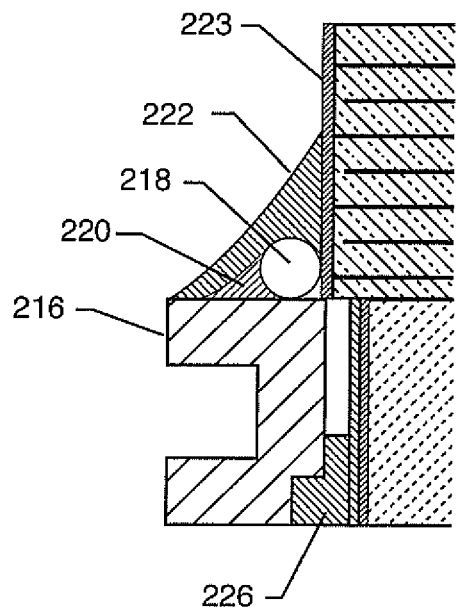
FIG. 63 is an enlarged sectional view taken from section 63-63 from FIG. 62 showing human or robotic manufacturing.

FIG. 63 is taken from section 63-63 from FIG. 62 showing what can happen during practical manufacturing using human or robotic dispensers. For example, if electrical connection material 222 is a solder or thermal-setting conductive adhesive, it can flow over the metal addition 218 and down across its weld or gold braze 220 to the ferrule 216. As shown in FIG. 63, this material 222 could also flow all the way down to the ferrule (which is subject to oxidation). The purpose of this is to illustrate that when materials are flowing, they can flow over the top of previously placed materials. However, the primary electrical path of the present invention is still between electrical connective material 222, the metal addition 218 and its metallurgical attachment 220 to the ferrule 216.

Figure 64:
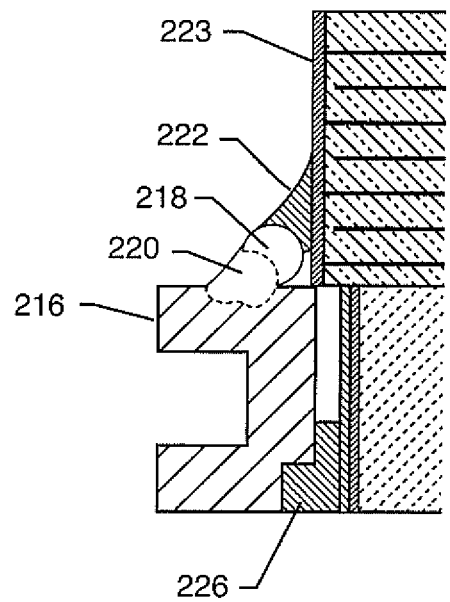
FIG. 64 is an enlarged sectional view taken from section 64-64 from FIG. 62 showing a laser-welded metallurgical bond.

FIG. 64 is taken from section 64-64 from FIG. 62 and shows what the assembly of FIG. 62 would really look like after a laser welding or brazing 220 of the metal addition 218. We can see that part of it has reflowed or become molten and it has flowed in and metallurgically bonded with the titanium of the ferrule 216. This metallurgical bond is illustrated by 220, but as can be seen in FIG. 64, it would be more normal that it would have an irregular shape, as illustrated.

Figure 65:
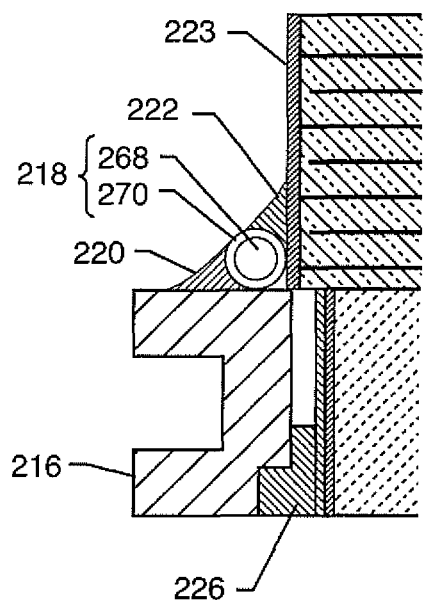
FIG. 65 is an enlarged sectional view similar to section 63-63 now showing a circular clad wire 218 as an oxide-resistant metal addition.

FIG. 65 is very similar to section 63-63 taken from FIG. 62 except that in this case, the oxide-resistant metal addition 218 is a clad wire, which has an core 268 supporting an outer cladding 270. There are many types of clad wire readily available, including laser cladded wire wherein cladding is achieved using a powdered or wire feedstock metal that is melted and consolidated by use of a laser to clad the core metal. Additionally, this enables mixed geometry cladding options, and particular ones that pose manufacturability challenges from traditional cladding methods. As one example, a platinum clad silver or copper wire would be much cheaper than a solid platinum wire and would still provide an oxide-resistant metal addition. Other types of cladded wires include gold clad stainless steels, palladium clad MP35N, palladium clad Ni—Co—Cr—Mo alloys, platinum clad molybdenum, platinum iridium clad niobium, platinum clad tantalum, silver clad nitinol, silver clad nickel titanium alloys, gold clad nickel titanium alloys, platinum alloy clad molybdenum, gold alloy clad stainless steels, gold clad tantalum and other similar noble metal and noble metal alloy cladding of lower cost core metal option combinations. Such cladding/core options may be customer specified combinations as appropriate for the application performance demands and any combination of the cladding and core metal as given above are options. Additionally, more than one cladding layer may be used to achieve specific application performance needs.

Figure 66:
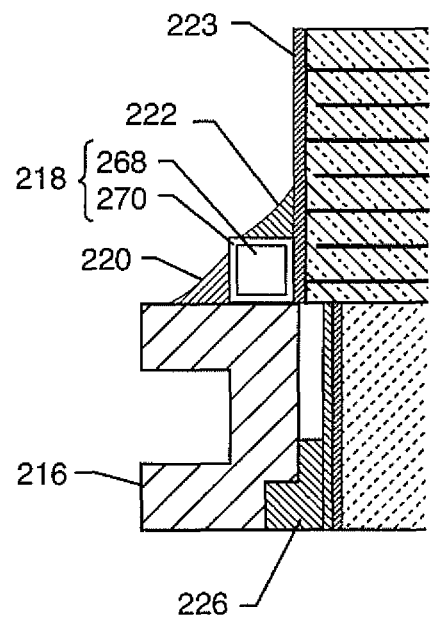
FIG. 66 is an enlarged sectional view similar to section 63-63 now showing a square clad wire 218 as an oxide-resistant metal addition.

FIG. 66 is very similar to FIG. 65, except in this case the cladded wire as an oxide-resistant metal addition 218 has a square cross-section instead of a round cross-section. Again, any geometry wire can be clad and the present invention is not limited to any one particular shape of wire.

FIG. 67 is very similar to FIG. 25, except that the oxide-resistant metal addition 218 is cladded, which is also shown in cross-section in FIG. 65 herein. Metal-clad wire may provide for a complete metallurgical bond between layers. It is typically manufactured using various heat, pressure and reduction techniques. Some non-limiting examples include gold cladding/stainless steel core, palladium cladding/MP35N core, or platinum cladding/niobium core. It will be understood by those skilled in the art that other cladding/core material options are possible. Herein the term "cladding" is a reference to many types of manufacturing processes including but not limited to plating, electroplating, drawn filled tube wires, vapor or chemical deposited coatings and other such metal overcoated options. Further, the term "core" as used herein may include a solid material, one or more fibers, twisted, braided or woven wires or hollow tubing with one or more lumens. Additionally, in an embodiment not shown, a core/cladding wire may be replaced with multiple fibers or wires comprising multiple and/or different materials.

FIG. 67 illustrates that the laser welding, brazing or other type of metallurgical attachment 220 (metal-joining process options) may be at or adjacent to the ends of the oxide-resistant metal addition 218, or distributed along the length thereof. The attachment 220 may be continuous or discontinuous along the length of the oxide-resistant metal addition 218. For example, the metallurgical attachment 220 may be at the ends of the first metal addition 218 and along the length, continuously or discontinuously, along the second metal addition 218. Depending on the method of metallurgical attachment chosen, the outer cladding 220 may selectively be raised to a temperature so that it melts preferentially with respect to the core 268 of the clad wire 218. In this case, the oxide-resistant metal addition 218 may comprise a cladding 270 having a lower melting temperature than that of the core metal 268. A metal-joining process then is used to melt and flow the cladding 270 of the wire 218 into contact with the ferrule 216. Variations regarding the degree of melt will be understood by those skilled in the art. For example, a gold or platinum-clad copper wire 218 can be laser welded 220 to the ferrule 216 with the result that the cladding 270 in addition to some of the core material 268 is melted onto the ferrule 216 to form the attachment 220. In this specific, but non-limiting case, the cladded wire 218 offers benefits when cost is an issue. Platinum or gold cladding 270 of a copper core 268 is more cost effective than a solid platinum or gold wire. Correspondingly, an oxide resistant plated wire may be used in place of a clad wire. It is noted that some areas of the clad wire 218 which do not form the metallurgical attachment 220 remain undisturbed, offering oxide-resistant electrical connection 222 for making contact between a capacitor ground metallization 223 and a secondary metal addition, and then, in turn, to the ferrule 216. Generally, a ferrule 216 is intended to be laser welded into the housing of an AIMD (not shown).

Figure 69:
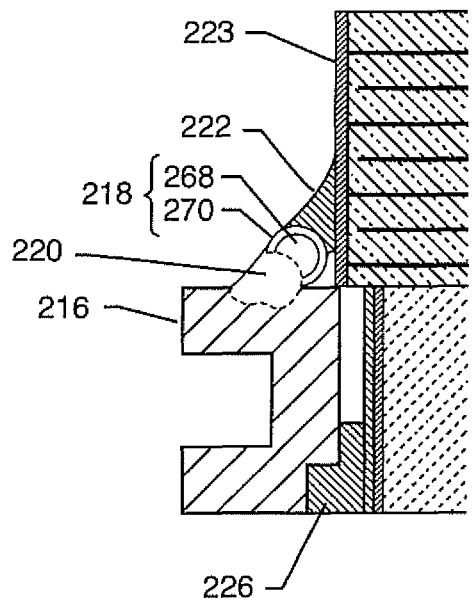
FIG. 69 is an enlarged sectional view taken along lines 69-69 from FIG. 67, but now showing the metal-joining process 220 with the cladding from the cladded wire metal addition 218.

FIG. 68 is very similar to FIG. 69, however now the cladded wires serving as the oxide-resistant metal additions 218 are discontinuous segments, placed along the sides or the ends (not shown) or around the circumference of a rectangular or round feedthrough capacitor (not shown). Referring once again to FIG. 68, each end of the cladded oxide-resistant metal additions 218 and 218' are shown to have been metallurgically attached to the ferrule 216 via a metallurgical attachment 220, 220'. In this case, the outer circumferential area near the ends of the cladded wires 218 and 218' are melted/welded to the ferrule 216. This leaves an undisturbed portion remaining in the center of each wire 218 and 218' where a thermal-setting conductive adhesive or solder 222 is provided to make an oxide-resistant connection to the capacitor outside perimeter ground metallization 223. Referring back again to FIG. 68, there are two wire segments 218 and 218', however, it is understood by those skilled in the art that there can be any number of segments 218, 218' . . . 218n.

FIG. 69 is a sectional view taken along section 69-69 of FIG. 67, showing that the metallurgical attachment 220 near the ends of the cladded oxide-resistant metal addition 218 has penetrated any oxide present on the ferrule material 216. It will be understood that metallurgical attachment then 220 can be formed during a laser weld process between ferrule 216 and cladded wire 218. Alternatively, metallurgical attachment 220 can be created by adding an additional material to the ferrule/wire combination and subjecting it to a metal joining process. FIG. 69 also illustrates that the metallurgical attachment 220 may include a portion of the cladding 270 and, optionally, a melted portion of the core 268.

Figure 70:
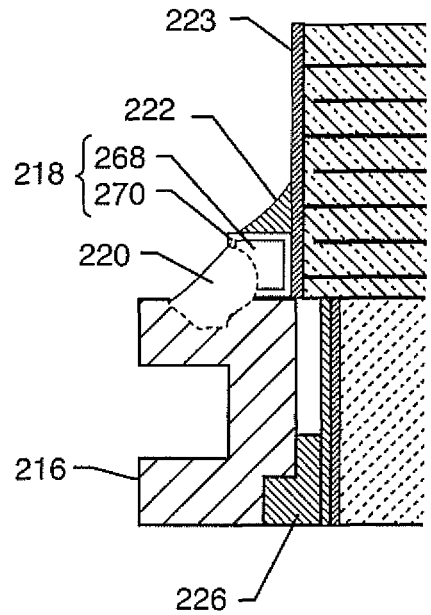
FIG. 70 is an enlarged sectional view similar to FIG. 69, but now showing a square and/or rectangular metal addition 218.

FIG. 70 is very similar to FIG. 69; however, the round wire of the metal addition 218 is square. Other shapes appropriate for a specific joint design will be understood by those skilled in the art, including oval, rectangular, triangular, and the like. The details provided for FIG. 69 apply entirely and equally to FIG. 70. In the case where more than one oxide-resistant metal addition 218 is used, each metal addition can be of the same shape or alternatively at least one of the multiple metal additions may be of a different shape.

Figure 71:
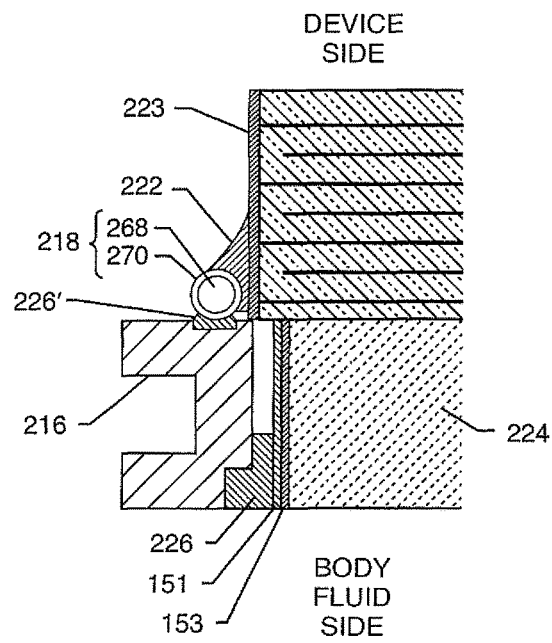
FIG. 71 is an enlarged sectional view similar to FIG. 69, but now showing a cladded wire metal addition 218 brazed to the ferrule in a secondary braze operation.

FIG. 71 is similar to FIG. 70 in that gold braze 226 is shown. The hermetic braze 226 seals the ferrule 216 to the adhesion 153 and wetting layers 151 supported on the insulator 224. In this embodiment, oxide-resistant metal addition 218 is metallurgically attached in an oxide resistant fashion to ferrule 216 using a low temperature brazing material 226'. The secondary brazing operation to attach the oxide-resistant metal addition 218 is performed prior to the capacitor 212 attachment process. Capacitor ground metallization 223 is then electrically attached to the cladding 270 of the oxide-resistant metal addition 218 using thermal-setting conductive adhesive or solder 222.

The low temperature brazing material 226' may comprise, but is not limited to, low temperature gold alloys, nano-gold preforms, fine gold wire with small grain size. Two non-limiting examples for lower temperature, biocompatible brazes (<850° C.) include: 82Au-18In (530° C.) and 88Au-12Ge (356° C.). Braze material 226' is within the device (AIMD) housing, so it need not be biocompatible. Among the alloys that could be considered are: copper/silver (28/72)—melting point (MP) 780° C., indium/copper/silver (10/27/63)—MP 685-730° C., gold/nickel (82/18)—MP 950° C., nickel/gold/copper (3/35/62)—MP 1000-1030° C., gold/nickel/titanium compositions including those disclosed in U.S. Pat. No. 4,938,922 (the contents of which are incorporated herein by reference), Johnson Matthey® silver-copper eutectic and pure metal brazes, Pallabraze® alloys and Orobraze® alloys. Active metal braze materials may also be considered. These materials have the primary braze material combined by forging or cladding to a small amount of another metal, usually titanium. It is known that the addition of titanium to various braze alloy compositions results in increased reactivity and considerable improvement in wetting behavior with a ceramic material. The ceramic is wet by the formation of an intermetallic interfacial reaction product which can then form a joint with the braze alloy. In active metal brazing, the metal facilitates the bonding mechanism to an un-metallized ceramic surface.

Figure 72:
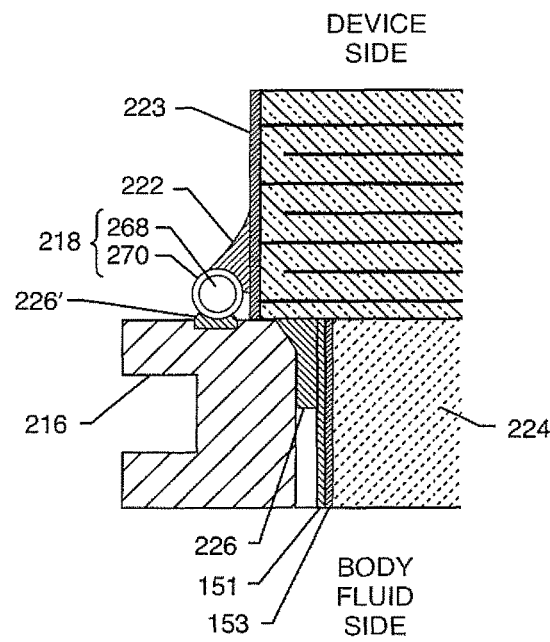
FIG. 72 is an enlarged sectional view similar to FIG. 71 wherein now the braze to the cladded wire metal addition 218 is made at the same time as the braze between the ferrule 216 and the metallization 223 of the insulator.

FIG. 72 is similar to FIG. 71 except in this case the hermetic seal gold braze 226 is disposed on the device side instead of the body fluid side. Since both brazes (226 and 226') are positioned for the melted gold to gravimetrically flow in the same direction, this design option offers single operation brazing to form the hermetic seal 226 and the attachment of the oxide-resistant metal addition 218 to the ferrule 216 by braze 226'.

Figure 73:
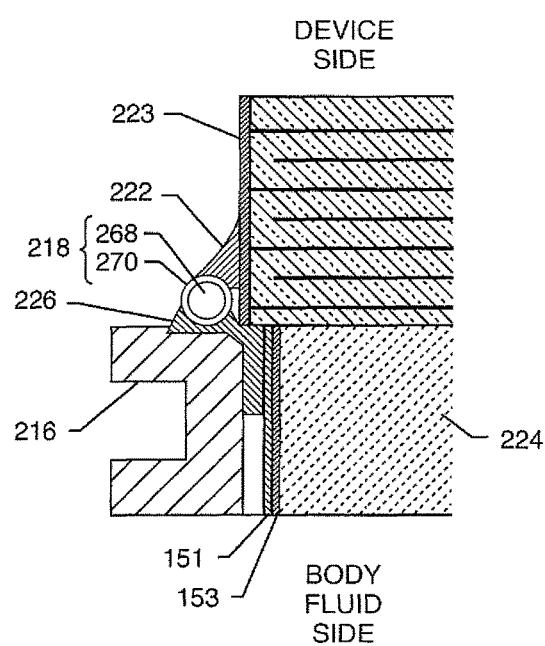
FIG. 73 is an enlarged sectional view similar to FIG. 72, but now showing that a common and continuous braze can connect the ferrule to the cladded wire metal addition 218 while also forming a hermetic seal between the ferrule and the metallization of the insulator.

FIG. 73 is very similar to FIG. 72, however, now a single gold braze 226 can simultaneously form the hermetic seal between ferrule 216 and the wetting 151 and adhesion layers 153 supported on the insulator 224 while at the same time electrically and mechanically joining the oxide-resistant metal addition 218 to the ferrule 216.

Although several embodiments have been described in detail for purposes of illustration, various modifications may be made to each without departing from the scope and spirit of the invention. Various features of one embodiment may be incorporated into another embodiment, as each embodiment is not exclusive of the other features taught and shown herein. Accordingly, the invention is not to be limited, except as by the appended claims.

What is claimed is:

1. A hermetically sealed filtered feedthrough assembly for an active implantable medical device, the filtered feedthrough assembly comprising:
   a) a ferrule of an electrically conductive material, the ferrule comprising a ferrule opening extending to a ferrule first end and a ferrule second end;
   b) an insulator of an electrically non-conductive material, the insulator comprising an insulator outer surface extending to an insulator first end and an insulator second end, wherein the insulator is disposed at least partially within the ferrule opening where a first gold braze hermetically seals the insulator to the ferrule, and wherein an insulator passageway extends through the insulator;
   c) an insulator metallization disposed at least partially on the insulator outer surface;
   d) a conductor residing in the insulator passageway where a second gold braze hermetically seals the conductor to the insulator, the conductor extending to a conductor first segment and a conductor second segment, wherein at least the conductor first segment extends outwardly beyond the insulator first end;
   e) a filter capacitor disposed near and/or on the insulator first end, the filter capacitor comprising:
      i) a capacitor dielectric comprising a dielectric outer surface extending to a first dielectric end and a second dielectric end;
      ii) at least one active electrode plate and at least one ground electrode plate disposed within and supported by the capacitor dielectric in an interleaved, partially overlapping relationship;
      iii) a dielectric passageway disposed through the capacitor dielectric to the dielectric first end and the dielectric second end;
      iv) a capacitor internal metallization disposed within the dielectric passageway and being conductively connected to the at least one active electrode plate and in non-conductive relation with the at least one ground electrode plate, wherein the conductor first segment extending outwardly beyond the insulator first end resides in the dielectric passageway where the conductor is conductively connected to the capacitor internal metallization and the at least one active electrode plate;
      v) a capacitor external metallization disposed at least partially on the dielectric outer surface, the capacitor external metallization being conductively connected to the at least one ground electrode plate and in non-conductive relation with the at least one active electrode plate;
   f) an oxide-resistant metal addition, comprising:
      i) a conductive core;
      ii) a conductive cladding disposed on the conductive core, wherein the conductive core and the conductive cladding are different materials;
   g) a first conductive connection between the oxide-resistant metal addition and the capacitor external metallization; and
   h) a second conductive connection between the oxide-resistant metal addition and the ferrule.

2. The feedthrough filter assembly of claim 1, wherein the first conductive connection is selected from the group consisting of a solder, a solder BGA, a solder paste, an epoxy, and a polyimide.

3. The feedthrough filter assembly of claim 2, wherein the second conductive connection comprises a laser weld.

4. The feedthrough filter assembly of claim 2, wherein the second conductive connection comprises a third braze.

5. The feedthrough filter assembly of claim 4, wherein the third braze comprising a lower temperature braze material than the first and second gold brazes.

6. The feedthrough filter assembly of claim 5, wherein the third braze is selected from the group consisting of a low temperature gold alloy, a nano-gold preform, and a fine gold wire with small grain size.

7. The feedthrough filter assembly of claim 5, wherein the first gold braze is disposed at or near the ferrule first end.

8. The feedthrough filter assembly of claim 7, wherein the first gold braze is disposed at or near the ferrule second end.

9. The feedthrough filter assembly of claim 8, wherein the first gold braze hermetically sealing the insulator to the ferrule also forms the second conductive connection between the oxide-resistant metal addition and the ferrule.

10. The feedthrough filter assembly of claim 1, wherein the conductive core of the oxide-resistant metal addition is selected from the group consisting of stainless steel, MP35N, and niobium.

11. The feedthrough filter assembly of claim 10, wherein the conductive core of the oxide-resistant metal addition is selected from the group consisting of a solid material, a hollow tube, a plurality of twisted fibers, a plurality of braided fibers, and a plurality of woven fibers.

12. The feedthrough filter assembly of claim 10, wherein the conductive cladding of the oxide-resistant metal addition is selected from the group consisting of gold, palladium and platinum.

13. The feedthrough filter assembly of claim 12, wherein the conductive cladding of the oxide-resistant metal addition is characterized as having been contacted to the conductive core by a process selected from the group consisting of plating, electroplating, as a drawn filled tubing, as a vapor deposition, as a chemical deposition, and as an overcoating.

14. The feedthrough filter assembly of claim 1, wherein the oxide-resistant metal addition comprises a plurality of oxide-resistant metal additions.

15. The feedthrough filter assembly of claim 1, wherein the first conductive connection comprises a plurality of first conductive connections.

16. The feedthrough filter assembly of claim 1, wherein the second conductive connection comprises a plurality of second conductive connections.

17. The feedthrough filter assembly of claim 1, wherein the first conductive connection is spaced from the second conductive connection along a length of the oxide-resistant metal addition.

18. The feedthrough filter assembly of claim 1, wherein the capacitor external metallization comprises an adhesion metallization and a wetting metallization, and wherein the adhesion metallization is disposed at least partially on the insulator outer surface and the wetting metallization is disposed on the adhesion metallization.

19. The feedthrough filter assembly of claim 1, wherein an insulative washer is disposed between the insulator and the filter capacitor.

20. The feedthrough filter assembly of claim 1, wherein the ferrule is configured to be attachable to an opening in a housing of an active implantable medical device by a laser weld or braze.

21. The feedthrough filter assembly of claim 1, wherein the ferrule is a continuous part of an active implantable medical device housing.

22. The feedthrough filter assembly of claim 1, wherein the ferrule first end and the insulator first end are associated with a device side and the ferrule second end and the insulator second end are associated with a body fluid side of the assembly.

23. The feedthrough filter assembly of claim 1, wherein the second conductive connection comprises a portion of the cladding and the core of the oxide-resistant metal addition.

24. A hermetically sealed filtered feedthrough assembly for an active implantable medical device, the filtered feedthrough assembly comprising:
a) a ferrule of an electrically conductive material, the ferrule comprising a ferrule opening extending to a ferrule first end and a ferrule second end, wherein the ferrule is configured to be attachable to an opening in a housing of an active implantable medical device;
b) an insulator of an electrically non-conductive material, the insulator comprising an insulator outer surface extending to an insulator first end and an insulator second end, wherein the insulator is disposed at least partially within the ferrule opening where a first gold braze hermetically seals the insulator to the ferrule, and wherein an insulator passageway extends through the insulator;
c) an insulator metallization disposed at least partially on the insulator outer surface;
d) a conductor residing in the insulator passageway where a second gold braze hermetically seals the conductor to the insulator, the conductor extending to a conductor first segment and a conductor second segment, wherein at least the conductor first segment extends outwardly beyond the insulator first end;
e) a filter capacitor disposed near and/or on the insulator first end, the filter capacitor comprising:
  i) a capacitor dielectric comprising a dielectric outer surface extending to a first dielectric end and a second dielectric end;
  ii) at least one active electrode plate and at least one ground electrode plate disposed within and supported by the capacitor dielectric in an interleaved, partially overlapping relationship;
  iii) a dielectric passageway disposed through the capacitor dielectric to the dielectric first end and the dielectric second end;
  iv) a capacitor internal metallization disposed within the dielectric passageway and being conductively connected to the at least one active electrode plate and in non-conductive relation with the at least one ground electrode plate, wherein the conductor first segment extending outwardly beyond the insulator first end resides in the dielectric passageway where the conductor is conductively connected to the capacitor internal metallization and the at least one active electrode plate;
  v) a capacitor external metallization disposed at least partially on the dielectric outer surface, the capacitor external metallization being conductively connected to the at least one ground electrode plate and in non-conductive relation with the at least one active electrode plate;
f) an oxide-resistant metal addition, comprising:
  i) a conductive core;
  ii) a conductive cladding disposed on the conductive core, wherein the conductive core and the conductive cladding are different materials;
g) a first conductive connection between the oxide-resistant metal addition and the capacitor external metallization; and
h) a second conductive connection between the oxide-resistant metal addition and the ferrule, wherein the second conductive connection comprise a portion of the cladding contacting the ferrule.

* * * * *